United States Patent [19]

Reyes et al.

[11] Patent Number: 5,843,636
[45] Date of Patent: Dec. 1, 1998

[54] HEPATITIS C VIRUS EPITOPES

[75] Inventors: Gregory R. Reyes; Jungsuh P. Kim, both of Palo Alto; Randolph Moeckli, Redwood City; Christian C. Simonsen, Saratoga, all of Calif.

[73] Assignee: Genelabs Technologies, Inc., Redwood City, Calif.

[21] Appl. No.: 407,410

[22] Filed: Mar. 17, 1995

Related U.S. Application Data

[60] Division of Ser. No. 681,703, Apr. 5, 1991, Pat. No. 5,443, 965, which is a continuation-in-part of Ser. No. 594,854, Oct. 10, 1990, abandoned, which is a continuation-in-part of Ser. No. 205,611, Apr. 6, 1990, abandoned.

[51] Int. Cl.$^6$ .............................. C12Q 1/70; C12P 21/06; C07H 17/00
[52] U.S. Cl. .............................. 435/5; 435/69.3; 530/350; 536/23.72
[58] Field of Search ...................... 435/69.3, 5; 530/350; 536/23.72

[56] References Cited

U.S. PATENT DOCUMENTS 5,350,671  9/1994  Houghton et al. ............................ 435/5
5,371,017  12/1994  Houghton et al. ................... 536/23.72

*Primary Examiner*—Michael P. Woodward
*Attorney, Agent, or Firm*—Dehlinger & Associates

[57] ABSTRACT

Peptide antigens which are immunoreactive with sera from individuals infected with hepatitis C virus (HCV) are disclosed. Several of the antigens are immunologically reactive with antibodies present in individuals identified as having chronic and acute HCV infection. The antigens are useful in diagnostic methods for detecting HCV infection in humans. Also disclosed are corresponding genomic-fragment clones containing polynucleotides encoding the open reading frame sequences for the antigenic peptides.

12 Claims, 21 Drawing Sheets

```
GAA TTC CTC GTG CAA GCG TGG AAG TCC AAG AAA ACC CCA ATG GGG TTC
TCG TAT GAT ACC CGC TGC TTT GAC TCC ACA GTC ACT GAG AGC GAC ATC
CGT ACG GAG GAG GCA ATC TAC CAA TGT TGT GAC CTC GAC CCC CAA GCC
CGC GTG GCC ATC AAG TCC CTC ACC GAG AGG CTT TAT GTT GGG GGC CCT
CTT ACC AAT TCA AGG GGG GAG AAC TGC GGC TAT CGC AGG TGC CGC GCG
AGC GGC GTA CTG ACA ACT AGC TGT GGT AAC ACC CTC ACT TGC TAC ATC
AAG GCC CGG GCA GCC TGT CGA GCC GCA GGG CTC CAG GAC TGC ACC ATG
CTC GTG TGT GGC GAC GAC TTA GTC GTT ATC TGT GAA AGC GCG GGG GTC
CAG GAG GAC GCG GCG AGC CTG AGA GCC TTC ACG GAG GCT ATG ACC AGG
TAC TCC GCC CCC CCC GGG GAC CCC CCA CAA CCA GAA TAC GAC TTG GAG
CTC ATA ACA TCA TGC TCC TCC AAC GTG TCA GTC GCC CAC GAC GGC GCT
GGA AAG AGG GTC TAC TAC CTC ACC CGG
◄─────────────────────── R9
```

Fig. 3

```
GAA TTC TTC ACA GAA TTG GAC GGG GTG CGC CTA CAT AGG TTT GCG CCC
                                                F7
CCC TGC AAG CCC TTG CTG CGG GAG GAG GTA TCA TTC AGA GTA GGA CTC
CAC GAA TAC CCG GTA GGG TCG CAA TTA CCT TGC GAG CCC GAA CCG GAT
GTG GCC GTG TTG ACG TCC ATG CTC ACT GAT CCC TCC CAT ATA ACA GCA
GAG GCG GCC GGG CGA AGG TTG GCG AGG GGA TCA CCC CCT CTG TGC CC
AGC TCC TCG GCT AGC CAG CTA TCC GCT CCA TCT CTC AAG GCA ACT TGC
ACC GCT AAC CAT GAC TCC CCT GAT GCT GAG CTC ATA GAG GCC AAC CTC
CTA TGG AGG CAG GAG ATG GGC GGC AAC ATC ACC AGG GTT GAG TCA GAA
AAC AAA GTG GTG ATT CTG GAC TCC TTC GAT CCG CTT GTG GCG GAG GAG
GAC GAG CGG GAG ATC TCC GTA CCC GCA GAA ATC CTG CGG AAG TCT CGG
AGA TTC GCC CAG GCC CTG CCC GTT TGG GCG CGG CCG GAC TAT AAC CCC
CCG CTA GTG GAG ACG TGG AAA AAG CCC GAC TAC GAA CCA CCT GTG GTC
CAT GGC TGT CCG CTT CCA CCT CCA AAG TCC CCT CCT GTG CCT CCG CCT
CGG AAG AAG CGG ACG GTG GTC CTC ACT GAA TCA ACC CTA TCT ACT GCC
TTG GCC GAG CTC GCC ACC AGA AGC TTT GGC AGC TCC TCA ACT TCC GGC
ATT ACG GGC GAC AAT ACG ACA ACA TCC TCT GAG CCC GCC CCT TCT GGC
TGC CCC CCC GAC TCC GAC GCT GAG TCC TAT TCC TCC ATG CCC CCC CTG
GAG GGG GAG CCT GGG GAT CCG GAT CTT AGC GAC GGG TCA TGG TCA ACG
GTC AGT AGT GAG GCC AAC GCG GAG GAT GTC GTG TGC TGC TCA ATG TCT
          F8
TAC TCT TGG ACA GGC GCA CTC GTC ACC CCG TGC GCC GCG GAA GAA CAG
AAA CTG CCC ATC AAT GCA CTA AGC AAC TCG TTG CTA CGT CAC CAC AAT
TTG GTG TAT TCC ACC ACC TCA CGC AGT GCT TGC CAA AGG CAG AAG AAA
                                              R8
GTC ACA TTT GAC AGA CTG CAA GTT CTG GAC AGC ATT ACA GAC GTA
CTC AAG GAG GTT AAA GCA GCG GCG TCA AAA GTG AAG CTA ACT TGC TA
TCC GTA GAG GAA GCT TGC AGC CTG ACG CCC CAC TCA GCC AAA TCC
AAG TTT GGT TAT GGG GCA AAA GAC GTC CGT TGC CAT GCC AGA AAG GCC
GTA ACC CAC ATC AAC TCC GTG TGG AAA GAC TTC TGA AGA CAA TGT A
ACA CCA ATA GAC ACT ACC ATC ATG GCT AAG AAC GAG GTT TTC TGC GTT
CAG CCT GAG AAG GGG GGT CGT AAG CCA GCT CGT CTC ATC GTG TTC CCC
GAT CTG GGC GTG CGC GTG TGC GAA AAG ATG GCT TTG TAC GAC GTG GTT
ACC AAG CTC CCC TTG GCC GTG ATG GGA AGC TCC TAC GGA TTC AAA TAC
TCA CCA GGA CAG CGG GTT GAA TTC
```

Fig. 4

```
■S   T   T   G   E   I   P   F   Y   G   K   A   I   P   L   E
CC  ACC ACC GGA GAG ATC CCT TTT TAC GGC AAG GCT ATC CCC CTC GAA
 V   I   K   G   G   R   H   L   I   F   C   H   S   K   K   K
GTA ATC AAG GGG GGG AGA CAT CTC ATC TTC TGT CAT TCA AAG AAG AAG
 C   D   E   L   A   A   K   L   V   A   L   G   I   N   A   V
TGC GAC GAA CTC GCC GCA AAG CTG GTC GCA TTG GGC ATC AAT GCC GTG
 A   Y   Y   R   G   L   D   V   S   V   I   P   T   S   G   D
GCC TAC TAC CGC GGT CTT GAC GTG TCC GTC ATC CCG ACC AGC GGC GAT
 V   V   V   V   A   T   D   A   L   M   T   G   Y   T   G   D
GTT GTC GTC GTG GCA ACC GAT GCC CTC ATG ACC GGC TAT ACC GGC GAC
 F   D   S   V   I   D   C   N   T   C   V   T   Q   T   V   D
TTC GAC TCG GTG ATA GAC TGC AAT ACG TGT GTC ACC CAG ACA GTC GAT
 F   S   L   D   P   T   F   T   I   E   T   I   T   L   P   Q
TTC AGC CTT GAC CCT ACC TTC ACC ATT GAG ACA ATC ACG CTC CCC CAG
 D   A   V   S   R   T   Q   R   R   G   R   T   G ■ R   G   K
GAT GCT GTC TCC CGC ACT CAA CGT CGG GGC AGG ACT GGC AGG GGG AAG
 P   G   I   Y   R   F   V   A   P   G   E   R   P   S   G   M
CCA GGC ATC TAC AGA TTT GTG GCA CCG GGG GAG CGC CCC TCC GGC ATG
 F   D   S   S   V   L   C   E   C   Y   D   A   G   C   A   W
TTC GAC TCG TCC GTC CTC TGT GAG TGC TAT GAC GCA GGC TGT GCT TGG
 Y   E   L ▲ T   P   A   E   T   T   V   R   L   R   A   Y   M
TAT GAG CTC ACG CCC GCC GAG ACT ACA GTT AGG CTA CGA GCG TAC ATG
 N   T   P   G   L   P   V   C   Q   D ✱
AAC ACC CCG GGG CTT CCC GTG TGC CAG GAC
```

```
GAA TTC CGC ACG CCC GCC GAG ACT ACA GTT AGG CTA CGG GCG TAC
 45
Glu Phe Arg Thr Pro Ala Glu Thr Thr Val Arg Leu Arg Ala Tyr
 15
ATG AAC ACT CCG GGG CTT CCC GTG TGC CAG GAC GGA ATT CCG TCC
 90
Met Asn Thr Pro Gly Leu Pro Val Cys Gln Asp Gly Ilu Pro Ser
 30
CCG TCC ACC ACC GGA GAG ATC CCT TTT TAC GGC AAG GCT ATC CCC
135
Pro Ser Thr Thr Gly Glu Ilu Pro Phe Tyr Gly Lys Ala Ilu Pro
 45
CTC GAA GTA ATC AAG GGG GGG AGA CAT CTC ATC TTC TGT CAT TCA
180
Leu Glu Val Ilu Lys Gly Gly Arg His Leu Ilu Phe Cys His Ser
 60
AAG AAG TGC GAC GAA CTC GCC GCA AAG CTG GTC GCA TTG GGC
225
Lys Lys Cys Asp Glu Leu Ala Ala Lys Leu Val Ala Leu Gly
 75
ATC AAT GCC GTG GCC TAC TAC CGC GGT CTT GAC GTG TCC GTC ATC
270
Ilu Asn Ala Val Ala Tyr Tyr Arg Gly Leu Asp Val Ser Val Ilu
 90
```

```
CCG ACC AGC GGC GAT GTT GTC GTC GTG GCA ACC GAT GCC CTC ATG
315
Pro Thr Ser Gly Asp Val Val Val Val Ala Thr Asp Ala Leu Met
105

ACC GGC TAT ACC GGC GAC TTC GAC TCG GTG ATA GAC TGC AAT ACG
360
Thr Gly Tyr Thr Gly Asp Phe Asp Ser Val Ilu Asp Cys Asn Thr
120

TGT GTC ACC CAG ACA GTC GAT TTC AGC CTT GAC CCT ACC TTC ACC
405
Cys Val Thr Gln Thr Val Asp Phe Ser Leu Asp Pro Thr Phe Thr
135

ATT GAG ACA ATC ACG CTC CCC CAG GAT GCT GTC TCC CGC ACT CAA
450
Ilu Glu Thr Ilu Thr Leu Pro Gln Asp Ala Val Ser Arg Thr Gln
150

CGT CGG GGC AGG ACT GGC ACG GAA TTC 477
Arg Arg Gly Arg Thr Gly Thr Glu Phe 159
```

Fig. 6B

```
                                            G   G   G
  1     CC ATG GGC ACG ATT CCC AAA CCT CAA AAA AAA AAC AAA CGT
           M   G   T   I   P   K   P   Q   K   K   N   K   R
 43     AAC ACC AAC CGT CGC CCA CGG GAC GTC AAG TTC CCG GGT GGC
         N   T   N   R   R   P   R   D   V   K   F   P   G   G
 85     GGT CAG ATC GTT GGT GGA GTT TAC TTG TTG CCG CGC AGG GGC
         G   Q   I   V   G   G   V   Y   L   L   P   R   R   G
127     CCT AGA TTG GGT GTG CGC GCG ACG AGA AAG ACT TCC GAG CGG
         P   R   L   G   V   R   A   T   R   K   T   S   E   R
169     TCG CAA CCT CGA GGT AGA CGT CAG CCT ATC CCC AAG GCT CGT
         S   Q   P   R   G   R   R   Q   P   I   P   K   A   R
211     CGG CCC GAG GGC AGG ACC TGG GCT CAG CCC GGG TAC CCT TGG
         R   P   E   G   R   T   W   A   Q   P   G   Y   P   W
253     CCC CTC TAT GGC AAT GAG GGC TGC GGG TGG GCG GGA TGG CTC
         P   L   Y   G   N   E   G   C   G   W   A   G   W   L
295     CTG TCT CCC CGT GGC TCT CGG CCT AGC TGG GGC CCC ACA GAC
         L   S   P   R   G   S   R   P   S   W   G   P   T   D
337     CCC CGG CGT AGG TCG CGC AAT TTG GGT AAG GTC ATC GAT ACC
         P   R   R   R   S   R   N   L   G   K   V   I   D   T
379     CTT ACG TGC GGC TTC GCC GAC CTC ATG GGG TAC ATA CCG CTC
         L   T   C   G   F   A   D   L   M   G   Y   I   P   L
421     GTC GGC GCC CCT CTT GGA GGC GCT GCC AGG GCC CTG GCG CAT
         V   G   A   P   L   G   G   A   A   R   A   L   A   H
463     GGC GTC CGG GTT CTG GAA GAC GGC GTG AAC TAT GCA ACA GGG
         G   V   R   V   L   E   D   G   V   N   Y   A   T   G
505     AAC CTT CCT GGT TGC TCT TTC TCT ATC TTC CTT CTG GCC CTG
         N   L   P   G   C   S   F   S   I   F   L   L   A   L
547     CTC TCT TGC TTG ACT GTG CCC GCT TCG GCC TAC CAA GTG CGC
         L   S   C   L   T   V   P   A   S   A   Y   Q   V   R
589     AAC TCC ACG GGG CTT TAC CAC GTC ACC AAT GAT TGC CCT AAC
         N   S   T   G   L   Y   H   V   T   N   D   C   P   N
631     TCG AGC ATT GTG TAC GAG TAA TAG GGA TCC          659
         S   S   I   V   Y   E   Z   Z   G   S
```

Fig. 8A

```
                   10        20        30        40        50        60
                    |         |         |         |         |         |
                           A   A   A
                          (wild Type)
         ATGGGCACGAATCCTAAACCTCAGAAGAAGAACAAACGTAACACCAACCGTCGCCCACAG
    gatccATGGGCACGAATCCTAAAC->
         Primer C1

METGlyThrAsnProLysProGlnLysLysAsnLysArgAsnThrAsnArgArgProGln 70        80        90       100       110       120
                    |         |         |         |         |         |

GACGTCAAGTTCCCGGGTGGCGGTCAGATCGTTGGTGGAGTTTACTTGTTGCCGCGCAGG
                               gagcccatgggtGGAGTTTACTTGTTGCC->
                                            Primer C100

<- TCAGATCGTTGGTGGAGTTTtaatagggatccgg
                                   Primer NC105

AspValLysPheProGlyGlyGlyGlnIleValGlyGlyValTyrLeuLeuProArgArg 130       140       150       160       170       180
                    |         |         |         |         |         |

GGCCCTAGATTGGGTGTGCGCGCGACGAGAAAGACTTCCGAGCGGTCGCAACCTCGAGGT

GlyProArgLeuGlyValArgAlaThrArgLysThrSerGluArgSerGlnProArgGly 190       200       210       220       230       240
                    |         |         |         |         |         |

AGACGTCAGCCTATCCCCAAGGCTCGTCGGCCCGAGGGCAGGACCTGGGCTCAGCCCGGG

ArgArgGlnProIleProLysAlaArgArgProGluGlyArgThrTrpAlaGlnProGly 250       260       270       280       290       300
                    |         |         |         |         |         |

TACCCTTGGCCCCTCTATGGCAATGAGGGCTGCGGGTGGGCGGGATGGCTCCTGTCTCCC
                              gagcccatGGGCTGCGGGTGGGCGGG
                                 Primer C270->
                  <-- CTCTATGGCAATGAGGGCTaagggatccggcc
                              <-Primer NC270
         TyrProTrpProLeuTyrGlyAsnGluGlyCysGlyTrpAlaGlyTrpLeuLeuSerPro
```

Fig. 8B

```
              310       320       330       340       350       360
               |         |         |         |         |         |
          CGTGGCTCTCGGCCTAGCTGGGGCCCCACAGACCCCCGGCGTAGGTCGCGCAATTTGGGT
                                                      gagcccaTGGGT
                                                       (C360->)

<--GGCGTAGGTCGCGCAATTTGtaa
                                                   <-Primer NC360
ggatccggcc
    ArgGlySerArgProSerTrpGlyProThrAspProArgArgArgSerArgAsnLeuGly 370       380       390       400       410       420
               |         |         |         |         |         |
          AAGGTCATCGATACCCTTACGTGCGGCTTCGCCGACCTCATGGGGTACATACCGCTCGTC
          AAGGTCATCGATACC
          Primer C360->
    LysValIleAspThrLeuThrCysGlyPheAlaAspLeuMETGlyTyrIleProLeuVal 430       440       450       460       470       480
               |         |         |         |         |         |
          GGCGCCCCTCTTGGAGGCGCTGCCAGGGCCCTGGCGCATGGCGTCCGGGTTCTGGAAGAC
                     <--GGAGGCGCTGCCAGGGCCtaaggatccggcc
                     <--   Primer NC450
    GlyAlaProLeuGlyGlyAlaAlaArgAlaLeuAlaHisGlyValArgValLeuGluAsp 490       500       510       520       530       540
               |         |         |         |         |         |
          GGCGTGAACTATGCAACAGGGAACCTTCCTGGTTGCTCTTTCTCTATCTTCCTTCTGGCC
                      <--GCAACAGGGAACCTTCCTGGTTaaggatccggcc
                          <-- Primer NC520
    GlyValAsnTyrAlaThrGlyAsnLeuProGlyCysSerPheSerIlePheLeuLeuAla 550       560       570       580       590       600
               |         |         |         |         |         |
          CTGCTCTCTTGCTTGACTGTGCCCGCTTCGGCCTACCAAGTGCGCAACTCCACGGGGCTT
                       <--CTGTGCCCGCTTCGGCCTAaggatccggcc
                          <-- Primer NC580
    LeuLeuSerCysLeuThrValProAlaSerAlaTyrGlnValArgAsnSerThrGlyLeu 610       620       630       640       650
               |         |         |         |         |
          TACCACGTCACCAATGATTGCCCTAACTCGAGCATTGTGTACGAGTAATAGGGATCC
                                        <--GTACGAGTAATAGGGATCCgaa
                                            <--Primer NC660
                                              (3'primer)
    TyrHisValThrAsnAspCysProAsnSerSerIleValTyrGlu------GlySer
```

Fig. 8C

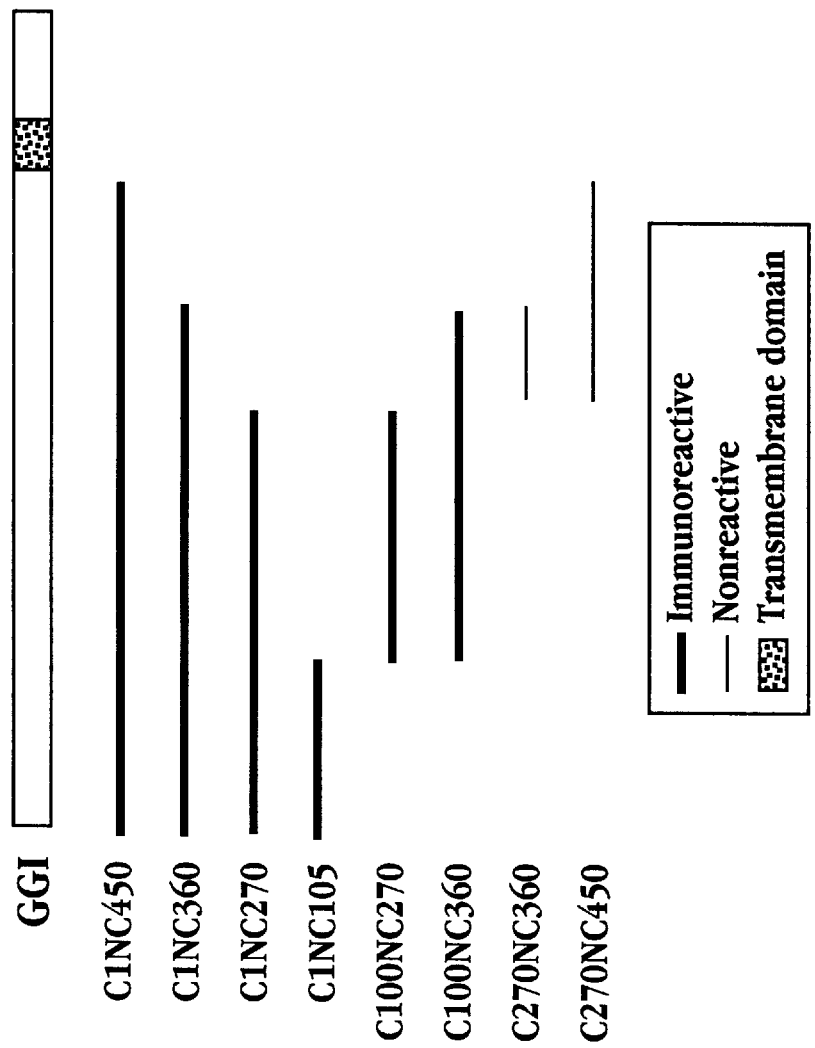

Fig 11A

```
              10        20        30        40        50        60
               |         |         |         |         |         |
    1  CAGGCTGTCCTGAGAGGCTAGCCAGCTGCCGACCCCTTACCGATTTTGACCAGGGCTGGG
       GTCCGACAGGACTCTCCGATCGGTCGACGGCTGGGGAATGGCTAAAACTGGTCCCGACCC

61  GCCCTATCAGTTATGCCAACGGAAGCGGCCCCGACCAGCGCCCCTACTGCTGGCACTACC
       CGGGATAGTCAATACGGTTGCCTTCGCCGGGGCTGGTCGCGGGGATGACGACCGTGATGG

121  CCCCAAAACCTTGCGGTATTGTGCCCGCGAAGAGTGTGTGTGGTCCGGTATATTGCTTCA
       GGGGTTTTGGAACGCCATAACACGGGCGCTTCTCACACACACCAGGCCATATAACGAAGT

181  CTCCCAGCCCCGTGGTGGTGGGAACGACCGACAGGTCGGGCGCGCCCACCTACAGCTGGG
       GAGGGTCGGGGCACCACCACCCTTGCTGGCTGTCCAGCCCGCGCGGGTGGATGTCGACCC

241  GTGAAAATGATACGGACGTCTTCGTCCTTAACAATACCAGGCCACCGCTGGGCAATTGGT
       CACTTTTACTATGCCTGCAGAAGCAGGAATTGTTATGGTCCGGTGGCGACCCGTTAACCA

301  TCGGTTGTACCTGGATGAACTCAACTGGATTCACCAAAGTGTGCGGAGCGCCTCCTTGTG
       AGCCAACATGGACCTACTTGAGTTGACCTAAGTGGTTTCACACGCCTCGCGGAGGAACAC

361  TCATCGGAGGGGCGGGCAACAACACCCTGCACTGCCCCACTGATTGCTTCCGCAAGCATC
       AGTAGCCTCCCCGCCCGTTGTTGTGGGACGTGACGGGGTGACTAACGAAGGCGTTCGTAG

421  CGGACGCCACATACTCTCGGTGCGGCTCCGGTCCCTGGATCACACCCAGGTGCCTGGTCG
       GCCTGCGGTGTATGAGAGCCACGCCGAGGCCAGGGACCTAGTGTGGGTCCACGGACCAGC

481  ACTACCCGTATAGGCTTTGGCTTTGGCATTGTACCATCAACTACACCATATTTAAAATCA
       TGATGGGCATATCCGAAACCGAAACCGTAACATGGTAGTTGATGTGGTATAAATTTTAGT

541  GGATGTACGTGGGAGGGGTCGAACACAGGCTGGAAGCTGCCTGCAACTGGACGCGGGGCG
       CCTACATGCACCCTCCCCAGCTTGTGTCCGACCTTCGACGGACGTTGACCTGCGCCCCGC

601  AACGTTGCGATCTGGAAGACAGGGACAGGTCCGAGCTCAGCCCGTTACTGCTGACCACTA
       TTGCAACGCTAGACCTTCTGTCCCTGTCCAGGCTCGAGTCGGGCAATGACGACTGGTGAT

661  CACAGTGGCAGGTCCTCCCGTGTTCCTTCACAACCCTACCAGCCTTGTCCACCGGCCTCA
       GTGTCACCGTCCAGGAGGGCACAAGGAAGTGTTGGGATGGTCGGAACAGGTGGCCGGAGT

721  TCCACCTCCACCAGAACATTGTGGACGTGCAGTACTTGTACGGGGTGGGGTCAAGCATCG
       AGGTGGAGGTGGTCTTGTAACACCTGCACGTCATGAACATGCCCCACCCCAGTTCGTAGC

781  CGTCCTGGGCCATTAAGTGGGAGTACGTCGTTCTCCTGTTCCTTCTGCTTGCAGACGCGC
       GCAGGACCCGGTAATTCACCCTCATGCAGCAAGAGGACAAGGAAGACGAACGTCTGCGCG

841  GCGTCTGCTCCTGCTTGTGGATGATGCTACTCATATCCCAAGCGGAGGCGGCTTTGGAGA
       CGCAGACGAGGACGAACACCTACTACGATGAGTATAGGGTTCGCCTCCGCCGAAACCTCT

901  ACCTCGTAATACTTAATGCAGCATCCCTGGCCGGGACGCACGGTCTTGTATCCTTCCTCG
       TGGAGCATTATGAATTACGTCGTAGGGACCGGCCCTGCGTGCCAGAACATAGGAAGGAGC
```

Fig 11B

```
 961 TGTTCTTCTGCTTTGCATGGTATTTGAAGGGTAAGTGGGTGCCCGGAGCGGTCTACACCT
     ACAAGAAGACGAAACGTACCATAAACTTCCCATTCACCCACGGGCCTCGCCAGATGTGGA

1021 TCTACGGGATGTGGCCTCTCCTCCTGCTCCTGTTGGCGTTGCCCCAGCGGGCGTACGCGC
     AGATGCCCTACACCGGAGAGGAGGACGAGGACAACCGCAACGGGGTCGCCCGCATGCGCG

1081 TGGACACGGAGGTGGCCGCGTCGTGTGGCGGTGTTGTTCTCGTCGGGTTGATGGCGCTGA
     ACCTGTGCCTCCACCGGCGCAGCACACCGCCACAACAAGAGCAGCCCAACTACCGCGACT

1141 CTCTGTCACCATATTACAAGCGCTATATCAGCTGGTGCTTGTGGTGGCTTCAGTATTTTC
     GAGACAGTGGTATAATGTTCGCGATATAGTCGACCACGAACACCACCGAAGTCATAAAAG

1201 TGACCAGAGTGGAAGCGCAACTGCACGTGTGGATTCCCCCCCTCAACGTCCGAGGGGGGC
     ACTGGTCTCACCTTCGCGTTGACGTGCACACCTAAGGGGGGGAGTTGCAGGCTCCCCCCG

1261 GCGACGCCGTCATCTTACTCATGTGTGCTGTACACCCGACTCTGGTATTTGACATCACCA
     CGCTGCGGCAGTAGAATGAGTACACACGACATGTGGGCTGAGACCATAAACTGTAGTGGT

1321 AATTGCTGCTGGCCGTCTTCGGACCCCTTTGGATTCTTCAAGCCAGTTTGCTTAAAGTAC
     TTAACGACGACCGGCAGAAGCCTGGGGAAACCTAAGAAGTTCGGTCAAACGAATTTCATG

1381 CCTACTTTGTGCGCGTCCAAGGCCTTCTCCGGTTCTGCGCGTTAGCGCGGAAGATGATCG
     GGATGAAACACGCGCAGGTTCCGGAAGAGGCCAAGACGCGCAATCGCGCCTTCTACTAGC

1441 GAGGCCATTACGTGCAAATGGTCATCATTAAGTTAGGGGCGCTTACTGGCACCTATGTTT
     CTCCGGTAATGCACGTTTACCAGTAGTAATTCAATCCCCGCGAATGACCGTGGATACAAA

1501 ATAACCATCTCACTCCTCTTCGGGACTGGGCGCACAACGGCTTGCGAGATCTGGCCGTGG
     TATTGGTAGAGTGAGGAGAAGCCCTGACCCGCGTGTTGCCGAACGCTCTAGACCGGCACC

1561 CTGTAGAGCCAGTCGTCTTCTCCCAAATGGAGACCAAGCTCATCACGTGGGGGGCAGATA
     GACATCTCGGTCAGCAGAAGAGGGTTTACCTCTGGTTCGAGTAGTGCACCCCCCGTCTAT

1621 CCGCCGCGTGCGGTGACATCATCAACGGCTTGCCTGTTTCCGCCCGCAGGGGCCGGGAGA
     GGCGGCGCACGCCACTGTAGTAGTTGCCGAACGGACAAAGGCGGGCGTCCCCGGCCCTCT

1681 TACTGCTCGGGCCAGCCGATGGAATGGTCTCCAAGGGGTGGAGGTTGCTGGCGCCCATCA
     ATGACGAGCCCGGTCGGCTACCTTACCAGAGGTTCCCCACCTCCAACGACCGCGGGTAGT

1741 CGGCGTACGCCCAGCAGACAAGGGGCCTCCTAGGGTGCATAATCACCAGCCTAACTGGCC
     GCCGCATGCGGGTCGTCTGTTCCCCGGAGGATCCCACGTATTAGTGGTCGGATTGACCGG

1801 GGGACAAAAACCAAGTGGAGGGTGAGGTCCAGATTGTGTCAACTGCTGCCCAAACCTTCC
     CCCTGTTTTTGGTTCACCTCCCACTCCAGGTCTAACACAGTTGACGACGGGTTTGGAAGG

1861 TGGCAACGTGCATCAATGGGGTGTGCTGGACTGTCTACCACGGGCCGGAACGAGGACCA
     ACCGTTGCACGTAGTTACCCCACACGACCTGACAGATGGTGCCCCGGCCTTGCTCCTGGT
```

Fig 11C

```
1921 TCGCGTCACCCAAGGGTCCTGTCATCCAGATGTATACCAATGTAGACCAAGACCTTGTGG
     AGCGCAGTGGGTTCCCAGGACAGTAGGTCTACATATGGTTACATCTGGTTCTGGAACACC

1981 GCTGGCCCGCTCCGCAAGGTAGCCGCTCATTGACACCCTGCACTTGCGGCTCCTCGGACC
     CGACCGGGCGAGGCGTTCCATCGGCGAGTAACTGTGGGACGTGAACGCCGAGGAGCCTGG

2041 TTTACCTGGTCACGAGGCACGCCGATGTCATTCCCGTGCGCCGGCGGGGTGATAGCAGGG
     AAATGGACCAGTGCTCCGTGCGGCTACAGTAAGGGCACGCGGCCGCCCCACTATCGTCCC

2101 GCAGCCTGCTGTCGCCCCGGCCCATTTCCTACTTGAAAGGCTCCTCGGGGGGTCCGCTGT
     CGTCGGACGACAGCGGGGCCGGGTAAAGGATGAACTTTCCGAGGAGCCCCCCAGGCGACA

2161 TGTGCCCCGCGGGGCACGCCGTGGGCATATTTAGGGCCGCGGTGTGCACCCGTGGAGTGG
     ACACGGGGCGCCCCGTGCGGCACCCGTATAAATCCCGGCGCCACACGTGGGCACCTCACC

2221 CTAAGGCGGTGGACTTTATCCCTGTGGAGAACCTAGAGACAACCATGAGGTCCCCGGTGT
     GATTCCGCCACCTGAAATAGGGACACCTCTTGGATCTCTGTTGGTACTCCAGGGGCCACA

2281 TCACGGATAACTCCTCTCCACCAGTAGTGCCCCAGAGCTTCCAGGTGGCTCACCTCCATG
     AGTGCCTATTGAGGAGAGGTGGTCATCACGGGGTCTCGAAGGTCCACCGAGTGGAGGTAC

2341 CTCCCACAGGCAGCGGCAAAAGCACCAAGGTCCCGGCTGCATATGCAGCTCAGGGCTATA
     GAGGGTGTCCGTCGCCGTTTTCGTGGTTCCAGGGCCGACGTATACGTCGAGTCCCGATAT

2401 AGGTGCTAGTACTCAACCCCTCTGTTGCTGCAACACTGGGCTTTGGTGCTTACATGTCCA
     TCCACGATCATGAGTTGGGGAGACAACGACGTTGTGACCCGAAACCACGAATGTACAGGT

2461 AGGCTCATGGGATCGATCCTAACATCAGGACGGGGTGAGAACAATTACCACTGGCAGCC
     TCCGAGTACCCTAGCTAGGATTGTAGTCCTGGCCCCACTCTTGTTAATGGTGACCGTCGG

2521 CCATCACGTACTCCACCTACGGCAAGTTCCTTGCCGACGGCGGGTGCTCGGGGGGCGCTT
     GGTAGTGCATGAGGTGGATGCCGTTCAAGGAACGGCTGCCGCCCACGAGCCCCCCGCGAA

2581 ATGACATAATAATTTGTGACGAGTGCCACTCCACGGATGCCACATCCATCTTGGGCATCG
     TACTGTATTATTAAACACTGCTCACGGTGAGGTGCCTACGGTGTAGGTAGAACCCGTAGC

2641 GCACTGTCCTTGACCAAGCAGAGACTGCGGGGGCGAGACTGGTTGTGCTCGCCACCGCCA
     CGTGACAGGAACTGGTTCGTCTCTGACGCCCCGCTCTGACCAACACGAGCGGTGGCGGT

2701 CCCCTCCGGGCTCCGTCACTGTGCCCCATCCCAACATCGAGGAGGTTGCTCTGTCCACCA
     GGGGAGGCCCGAGGCAGTGACACGGGGTAGGGTTGTAGCTCCTCCAACGAGACAGGTGGT

2761 CCGGAGAGATCCCTTTTTACGGCAAGGCTATCCCCCTCGAAGTAATCAAGGGGGGGAGAC
     GGCCTCTCTAGGGAAAAATGCCGTTCCGATAGGGGAGCTTCATTAGTTCCCCCCCTCTG

2821 ATCTCATCTTCTGTCATTCAAAGAAGAAGTGCGACGAACTCGCCGCAAAGCTGGTCGCAT
     TAGAGTAGAAGACAGTAAGTTTCTTCTTCACGCTGCTTGAGCGGCGTTTCGACCAGCGTA

2881 TGGGCATCAATGCCGTGGCCTACTACCGCGGTCTTGACGTGTCCGTCATCCCGACCAGCG
     ACCCGTAGTTACGGCACCGGATGATGGCGCCAGAACTGCACAGGCAGTAGGGCTGGTCGC
```

Fig 11D

```
2941 GCGATGTTGTCGTCGTGGCAACCGATGCCCTCATGACCGGCTATACCGGCGACTTCGACT
     CGCTACAACAGCAGCACCGTTGGCTACGGGAGTACTGGCCGATATGGCCGCTGAAGCTGA

3001 CGGTGATAGACTGCAATACGTGTGTCACCCAGACAGTCGATTTCAGCCTTGACCCTACCT
     GCCACTATCTGACGTTATGCACACAGTGGGTCTGTCAGCTAAAGTCGGAACTGGGATGGA

3061 TCACCATTGAGACAATCACGCTCCCCAGGATGCTGTCTCCCGCACTCAACGTCGGGGCA
     AGTGGTAACTCTGTTAGTGCGAGGGGGTCCTACGACAGAGGGCGTGAGTTGCAGCCCCGT

3121 GGACTGGCAGGGGGAAGCCAGGCATCTACAGATTTGTGGCACCGGGGGAGCGCCCCTCCG
     CCTGACCGTCCCCCTTCGGTCCGTAGATGTCTAAACACCGTGGCCCCCTCGCGGGGAGGC

3181 GCATGTTCGACTCGTCCGTCCTCTGTGAGTGCTATGACGCAGGCTGTGCTTGGTATGAGC
     CGTACAAGCTGAGCAGGCAGGAGACACTCACGATACTGCGTCCGACACGAACCATACTCG

3241 TCACGCCCGCCGAGACTACAGTTAGGCTACGAGCGTACATGAACACCCCGGGGCTTCCCG
     AGTGCGGGCGGCTCTGATGTCAATCCGATGCTCGCATGTACTTGTGGGGCCCCGAAGGGC

3301 TGTGCCAGGACCATCTTGAATTTTGGGAGGGCGTCTTTACAGGCCTCACTCATATAGATG
     ACACGGTCCTGGTAGAACTTAAAACCCTCCCGCAGAAATGTCCGGAGTGAGTATATCTAC

3361 CCCACTTTCTATCCCAGACAAAGCAGAGTGGGGAGAACCTTCCTTACCTGGTAGCGTACC
     GGGTGAAAGATAGGGTCTGTTTCGTCTCACCCCTCTTGGAAGGAATGGACCATCGCATGG

3421 AAGCCACCGTGTGCGCTAGGGCTCAAGCCCCTCCCCATCGTGGGACCAGATGTGGAAGT
     TTCGGTGGCACACGCGATCCCGAGTTCGGGGAGGGGGTAGCACCCTGGTCTACACCTTCA

3481 GTTTGATTCGCCTCAAGCCCACCCTCCATGGGCCAACACCCCTGCTATACAGACTGGGCG
     CAAACTAAGCGGAGTTCGGGTGGGAGGTACCCGGTTGTGGGACGATATGTCTGACCCGC

3541 CTGTTCAGAATGAAATCACCCTGACGCACCCAGTCACCAAATACATCATGACATGCATGT
     GACAAGTCTTACTTTAGTGGGACTGCGTGGGTCAGTGGTTTATGTAGTACTGTACGTACA

3601 CGGCCGACCTGGAGGTCGTCACGAGCACCTGGGTGCTCGTTGGCGGCGTCCTGGCTGCTT
     GCCGGCTGGACCTCCAGCAGTGCTCGTGGACCCACGAGCAACCGCCGCAGGACCGACGAA

3661 TGGCCGCGTATTGCCTGTCAACAGGCTGCGTGGTCATAGTGGGCAGGGTCGTCTTGTCCG
     ACCGGCGCATAACGGACAGTTGTCCGACGCACCAGTATCACCCGTCCCAGCAGAACAGGC

3721 GGAAGCCGGCAATCATACCTGACAGGGAAGTCCTCTACCGAGAGTTCGATGAGATGGAAG
     CCTTCGGCCGTTAGTATGGACTGTCCCTTCAGGAGATGGCTCTCAAGCTACTCTACCTTC

3781 AGTGCTCTCAGCACTTACCGTACATCGAGCAAGGATGATGCTCGCCGAGCAGTTCAAGC
     TCACGAGAGTCGTGAATGGCATGTAGCTCGTTCCCTACTACGAGCGGCTCGTCAAGTTCG

3841 AGAAGGCCCTCGGCCTCCTGCAGACCGCGTCCCGTCAGGCAGAGGTTATCGCCCCTGCTG
     TCTTCCGGGAGCCGGAGGACGTCTGGCGCAGGGCAGTCCGTCTCCAATAGCGGGGACGAC
```

Fig 11E

```
3901 TCCAGACCAACTGGCAAAAACTCGAGACCTTCTGGGCGAAGCATATGTGGAACTTCATCA
     AGGTCTGGTTGACCGTTTTTGAGCTCTGGAAGACCCGCTTCGTATACACCTTGAAGTAGT

3961 GTGGGATACAATACTTGGCGGGCTTGTCAACGCTGCCTGGTAACCCCGCCATTGCTTCAT
     CACCCTATGTTATGAACCGCCCGAACAGTTGCGACGGACCATTGGGGCGGTAACGAAGTA

4021 TGATGGCTTTTACAGCTGCTGTCACCAGCCCACTAACCACTAGCCAAACCCTCCTCTTCA
     ACTACCGAAAATGTCGACGACAGTGGTCGGGTGATTGGTGATCGGTTTGGGAGGAGAAGT

4081 ACATATTGGGGGGGTGGGTGGCTGCCCAGCTCGCCGCCCCGGTGCCGCTACTGCCTTTG
     TGTATAACCCCCCCACCCACCGACGGGTCGAGCGGCGGGGGCCACGGCGATGACGGAAAC

4141 TGGGCGCTGGCTTAGCTGGCGCCGCCATCGGCAGTGTTGGACTGGGGAAGGTCCTCATAG
     ACCCGCGACCGAATCGACCGCGGCGGTAGCCGTCACAACCTGACCCCTTCCAGGAGTATC

4201 ACATCCTTGCAGGGTATGGCGCGGGCGTGGCGGGAGCTCTTGTGGCATTCAAGATCATGA
     TGTAGGAACGTCCCATACCGCGCCCGCACCGCCCTCGAGAACACCGTAAGTTCTAGTACT

4261 GCGGTGAGGTCCCCTCCACGGAGGACCTGGTCAATCTACTGCCCGCCATCCTCTCGCCCG
     CGCCACTCCAGGGGAGGTGCCTCCTGGACCAGTTAGATGACGGGCGGTAGGAGAGCGGGC

4321 GAGCCCTCGTAGTCGGCGTGGTCTGTGCAGCAATACTGCGCCGGCACGTTGGCCCGGGCG
     CTCGGGAGCATCAGCCGCACCAGACACGTCGTTATGACGCGGCCGTGCAACCGGGCCCGC

4381 AGGGGGCAGTGCAGTGGATGAACCGGCTGATAGCCTTCGCCTCCCGGGGGAACCATGTTT
     TCCCCCGTCACGTCACCTACTTGGCCGACTATCGGAAGCGGAGGGCCCCCTTGGTACAAA

4441 CCCCCACGCACTACGTGCCGGAGAGCGATGCAGCTGCCCGCGTCACTGCCATACTCAGCA
     GGGGGTGCGTGATGCACGGCCTCTCGCTACGTCGACGGGCGCAGTGACGGTATGAGTCGT

4501 GCCTCACTGTAACCCAGCTCCTGAGGCGACTGCACCAGTGGATAAGCTCGGAGTGTACCA
     CGGAGTGACATTGGGTCGAGGACTCCGCTGACGTGGTCACCTATTCGAGCCTCACATGGT

4561 CTCCATGCTCCGGTTCCTGGCTAAGGGACATCTGGGACTGGATATGCGAGGTGTTGAGCG
     GAGGTACGAGGCCAAGGACCGATTCCCTGTAGACCCTGACCTATACGCTCCACAACTCGC

4621 ACTTTAAGACCTGGCTAAAAGCTAAGCTCATGCCACAGCTGCCTGGGATCCCCTTTGTGT
     TGAAATTCTGGACCGATTTTCGATTCGAGTACGGTGTCGACGGACCCTAGGGGAAACACA

4681 CCTGCCAGCGCGGGTATAAGGGGGTCTGGCGAGTGGACGGCATCATGCACACTCGCTGCC
     GGACGGTCGCGCCCATATTCCCCCAGACCGCTCACCTGCCGTAGTACGTGTGAGCGACGG

4741 ACTGTGGAGCTGAGATCACTGGACATGTCAAAAACGGGACGATGAGGATCGTCGGTCCTA
     TGACACCTCGACTCTAGTGACCTGTACAGTTTTTGCCCTGCTACTCCTAGCAGCCAGGAT

4801 GGACCTGCAGGAACATGTGGAGTGGGACCTTCCCCATTAATGCCTACACCACGGGCCCCT
     CCTGGACGTCCTTGTACACCTCACCCTGGAAGGGGTAATTACGGATGTGGTGCCCGGGGA

4861 GTACCCCCCTTCCTGCGCCGAACTACACGTTCGCGCTATGGAGGGTGTCTGCAGAGGAAT
     CATGGGGGGAAGGACGCGGCTTGATGTGCAAGCGCGATACCTCCCACAGACGTCTCCTTA
```

Fig 11F

```
4921 ATGTGGAGATAAGGCAGGTGGGGGACTTCCACTACGTGACGGGTATGACTACTGACAATC
     TACACCTCTATTCCGTCCACCCCCTGAAGGTGATGCACTGCCCATACTGATGACTGTTAG

4981 TCAAATGCCCGTGCCAGGTCCCATCGCCCGAATTTTTCACAGAATTGGACGGGGTGCGCC
     AGTTTACGGGCACGGTCCAGGGTAGCGGGCTTAAAAAGTGTCTTAACCTGCCCCACGCGG

5041 TACATAGGTTTGCGCCCCCCTGCAAGCCCTTGCTGCGGGAGGAGGTATCATTCAGAGTAG
     ATGTATCCAAACGCGGGGGGACGTTCGGGAACGACGCCCTCCTCCATAGTAAGTCTCATC

5101 GACTCCACGAATACCCGGTAGGGTCGCAATTACCTTGCGAGCCCGAACCGGACGTGGCCG
     CTGAGGTGCTTATGGGCCATCCCAGCGTTAATGGAACGCTCGGGCTTGGCCTGCACCGGC

5161 TGTTGACGTCCATGCTCACTGATCCCTCCCATATAACAGCAGAGGCGGCCGGGCGAAGGT
     ACAACTGCAGGTACGAGTGACTAGGGAGGGTATATTGTCGTCTCCGCCGGCCCGCTTCCA

5221 TGGCGAGGGGATCACCCCCCTCTGTGGCCAGCTCCTCGGCTAGCCAGCTATCCGCTCCAT
     ACCGCTCCCCTAGTGGGGGGAGACACCGGTCGAGGAGCCGATCGGTCGATAGGCGAGGTA

5281 CTCTCAAGGCAACTTGCACCGCTAACCATGACTCCCCTGATGCTGAGCTCATAGAGGCCA
     GAGAGTTCCGTTGAACGTGGCGATTGGTACTGAGGGACTACGACTCGAGTATCTCCGGT

5341 ACCTCCTATGGAGGCAGGAGATGGGCGGCAACATCACCAGGGTTGAGTCAGAAAACAAAG
     TGGAGGATACCTCCGTCCTCTACCCGCCGTTGTAGTGGTCCCAACTCAGTCTTTTGTTTC

5401 TGGTGATTCTGGACTCCTTCGATCCGCTTGTGGCGGAGGAGGACGAGCGGGAGATCTCCG
     ACCACTAAGACCTGAGGAAGCTAGGCGAACACCGCCTCCTCCTGCTCGCCCTCTAGAGGC

5461 TACCCGCAGAAATCCTGCGGAAGTCTCGGAGATTCGCCCAGGCCCTGCCCGTTTGGGCGC
     ATGGGCGTCTTTAGGACGCCTTCAGAGCCTCTAAGCGGGTCCGGGACGGGCAAACCCGCG

5521 GGCCGGACTATAACCCCCCGCTAGTGGAGACGTGGAAAAAGCCCGACTACGAACCACCTG
     CCGGCCTGATATTGGGGGGCGATCACCTCTGCACCTTTTTCGGGCTGATGCTTGGTGGAC

5581 TGGTCCATGGCTGTCCGCTTCCACCTCCAAAGTCCCCTCCTGTGCCTCCGCCTCGGAAGA
     ACCAGGTACCGACAGGCGAAGGTGGAGGTTTCAGGGGAGGACACGGAGGCGGAGCCTTCT

5641 AGCGGACGGTGGTCCTCACTGAATCAACCCTATCTACTGCCTTGGCCGAGCTCGCCACCA
     TCGCCTGCCACCAGGAGTGACTTAGTTGGGATAGATGACGGAACCGGCTCGAGCGGTGGT

5701 GAAGCTTTGGCAGCTCCTCAACTTCCGGCATTACGGGCGACAATACGACAACATCCTCTG
     CTTCGAAACCGTCGAGGAGTTGAAGGCCGTAATGCCCGCTGTTATGCTGTTGTAGGAGAC

5761 AGCCCGCCCCTTCTGGCTGCCCCCCCGACTCCGACGCTGAGTCCTATTCCTCCATGCCCC
     TCGGGCGGGGAAGACCGACGGGGGGCTGAGGCTGCGACTCAGGATAAGGAGGTACGGGG

5821 CCCTGGAGGGGGAGCCTGGGGATCCGGATCTTAGCGACGGGTCATGGTCAACGGTCAGTA
     GGGACCTCCCCCTCGGACCCCTAGGCCTAGAATCGCTGCCCAGTACCAGTTGCCAGTCAT
```

Fig 11G

```
5881 GTGAGGCCAACGCGGAGGATGTCGTGTGCTGCTCAATGTCTTACTCTTGGACAGGCGCAC
     CACTCCGGTTGCGCCTCCTACAGCACACGACGAGTTACAGAATGAGAACCTGTCCGCGTG

5941 TCGTCACCCCGTGCGCCGCGGAAGAACAGAAACTGCCCATCAATGCACTAAGCAACTCGT
     AGCAGTGGGGCACGCGGCGCCTTCTTGTCTTTGACGGGTAGTTACGTGATTCGTTGAGCA

6001 TGCTACGTCACCACAATTTGGTGTATTCCACCACCTCACGCAGTGCTTGCCAAAGGCAGA
     ACGATGCAGTGGTGTTAAACCACATAAGGTGGTGGAGTGCGTCACGAACGGTTTCCGTCT

6061 AGAAAGTCACATTTGACAGACTGCAAGTTCTGGACAGCCATTACCAGGACGTACTCAAGG
     TCTTTCAGTGTAAACTGTCTGACGTTCAAGACCTGTCGGTAATGGTCCTGCATGAGTTCC

6121 AGGTTAAAGCAGCGGCGTCAAAAGTGAAGGCTAACTTGCTATCCGTAGAGGAAGCTTGCA
     TCCAATTTCGTCGCCGCAGTTTTCACTTCCGATTGAACGATAGGCATCTCCTTCGAACGT

6181 GCCTGACGCCCCCACACTCAGCCAAATCCAAGTTTGGTTATGGGCAAAAGACGTCCGTT
     CGGACTGCGGGGGTGTGAGTCGGTTTAGGTTCAAACCAATACCCCGTTTTCTGCAGGCAA

6241 GCCATGCCAGAAAGGCCGTAACCCACATCAACTCCGTGTGGAAAGACCTTCTGGAAGACA
     CGGTACGGTCTTTCCGGCATTGGGTGTAGTTGAGGCACACCTTTCTGGAAGACCTTCTGT

6301 ATGTAACACCAATAGACACTACCATCATGGCTAAGAACGAGGTTTTCTGCGTTCAGCCTG
     TACATTGTGGTTATCTGTGATGGTAGTACCGATTCTTGCTCCAAAAGACGCAAGTCGGAC

6361 AGAAGGGGGGTCGTAAGCCAGCTCGTCTCATCGTGTTCCCCGATCTGGGCGTGCGCGTGT
     TCTTCCCCCCAGCATTCGGTCGAGCAGAGTAGCACAAGGGGCTAGACCCGCACGCGCACA

6421 GCGAAAAGATGGCTTTGTACGACGTGGTTACAAAGCTCCCCTTGGCCGTGATGGGAAGCT
     CGCTTTTCTACCGAAACATGCTGCACCAATGTTTCGAGGGGAACCGGCACTACCCTTCGA

6481 CCTACGGATTCCAATACTCACCAGGACAGCGGGTTGAATTCCTCGTGCAAGCGTGGAAGT
     GGATGCCTAAGGTTATGAGTGGTCCTGTCGCCCAACTTAAGGAGCACGTTCGCACCTTCA

6541 CCAAGAAAACCCCAATGGGGTTCTCGTATGATACCCGCTGCTTTGACTCCACAGTCACTG
     GGTTCTTTTGGGGTTACCCCAAGAGCATACTATGGGCGACGAAACTGAGGTGTCAGTGAC

6601 AGAGCGACATCCGTACGGAGGAGGCAATCTACCAATGTTGTGACCTCGACCCCCAAGCCC
     TCTCGCTGTAGGCATGCCTCCTCCGTTAGATGGTTACAACACTGGAGCTGGGGGTTCGGG

6661 GCGTGGCCATCAAGTCCCTCACCGAGAGGCTTTATGTTGGGGGCCCTCTTACCAATTCAA
     CGCACCGGTAGTTCAGGGAGTGGCTCTCCGAAATACAACCCCCGGGAGAATGGTTAAGTT

6721 GGGGGGAGAACTGCGGCTATCGCAGGTGCCGCGCGAGCGGCGTACTGACAACTAGCTGTG
     CCCCCCTCTTGACGCCGATAGCGTCCACGGCGCGCTCGCCGCATGACTGTTGATCGACAC

6781 GTAACACCCTCACTTGCTACATCAAGGCCCGGGCAGCCTGTCGAGCCGCAGGGCTCCAGG
     CATTGTGGGAGTGAACGATGTAGTTCCGGGCCCGTCGGACAGCTCGGCGTCCCGAGGTCC

6841 ACTGCACCATGCTCGTGTGTGGCGACGACTTAGTCGTTATCTGTGAAAGCGCGGGGGTCC
     TGACGTGGTACGAGCACACACCGCTGCTGAATCAGCAATAGACACTTTCGCGCCCCCAGG
```

Fig 11H

```
6901 AGGAGGACGCGGCGAGCCTGAGAGCCTTCACGGAGGCTATGACCAGGTACTCCGCCCCCC
     TCCTCCTGCGCCGCTCGGACTCTCGGAAGTGCCTCCGATACTGGTCCATGAGGCGGGGGG

6961 CTGGGGACCCCCCACAACCAGAATACGACTTGGAGCTCATAACATCATGCTCCTCCAACG
     GACCCCTGGGGGGTGTTGGTCTTATGCTGAACCTCGAGTATTGTAGTACGAGGAGGTTGC

7021 TGTCAGTCGCCCACGACGGCGCTGGAAAGAGGGTCTACTACCTCACCCGTGACCCTACAA
     ACAGTCAGCGGGTGCTGCCGCGACCTTTCTCCCAGATGATGGAGTGGGCACTGGGATGTT

7081 CCCCCCTCGCGAGAGCTGCGTGGGAGACAGCAAGACACACTCCAGTCAATTCCTGGCTAG
     GGGGGGAGCGCTCTCGACGCACCCTCTGTCGTTCTGTGTGAGGTCAGTTAAGGACCGATC

7141 GCAACATAATCATGTTTGCCCCCACACTGTGGGCGAGGATGATACTGATGACCCATTTCT
     CGTTGTATTAGTACAAACGGGGGTGTGACACCCGCTCCTACTATGACTACTGGGTAAAGA

7201 TTAGCGTCCTTATAGCCAGGGACCAGCTTGAACAGGCCCTCGATTGCGAGATCTACGGGG
     AATCGCAGGAATATCGGTCCCTGGTCGAACTTGTCCGGGAGCTAACGCTCTAGATGCCCC

7261 CCTGCTACTCCATAGAACCACTTGATCTACCTCCAATCATTCAAAGACTC
     GGACGATGAGGTATCTTGGTGAACTAGATGGAGGTTAGTAAGTTTCTGAG
```

HEPATITIS C VIRUS EPITOPES

The present application is a division of application Ser. No. 07/681,703, filed Apr. 5, 1991, now U.S. Pat. No. 5,445,965 herein incorporated by reference, now allowed, which is a continuation-in-part of U.S. patent application Ser. No. 07/594,854, filed Oct. 10, 1990, abandoned which is a continuation-in-part of Ser. No. 07/505,611, filed Apr. 6, 1990 abandoned.

1. FIELD OF INVENTION

This invention relates to specific peptide viral antigens which are immunoreactive with sera from patients infected with parenterally transmitted non-A, non-B hepatitis virus (PT-NANBH, now called Hepatitis C Virus), to polynucleotide sequences which encode the peptides, to an expression system capable of producing the peptides, and to methods of using the peptides for detecting PT-NANBH infection in human sera.

2. REFERENCES

Atkins, et al., Cell 62:413–423 (1990).
Ausubel, F. M., et al., *Current Protocols in Molecular Biology*, John Wiley and Sons, Inc., Media PA.
Bradley, D. W., et al., J. Infec. Dis., 148:2 (1983).
Bradley, D. W., et al., J Gen. Virol., 69:1 (1988).
Bradley, D. W. et al., Proc. Nat. Acad. Sci., USA, 84:6277 (1987).
Chomczynski, P., et al., Anal Biochem, 162:156 (1987).
Choo, Q.-L., et al, Science, 244:359 (1989).
*Current Protocols in Molecular Biology*, Wiley Interscience, Chapter 10.
Dienstag, J. L., et al, Sem Liver Disease, 6:67 (1986)
Feramisco, J. R., et al., J. Biol. Chem. 257(18):11024 (1982).
Gubler, U., et al, Gene, 25:263 (1983).
Hunyh, T. V., et al, in *DNA Cloning Techniques: A Practical Approach* (D. Glover, ed.) IRL Press (1985).
Klein, P., et al., Biochem. Biophys. ACTA 815:468 (1985).
Kuo, G., et al., Science, 244:362 (1989).
Kyte, J., et al., J. Mol. Biol. 157:105 (1982).
Maniatis, T., et al. *Molecular Cloning: A Laboratory Manual*, Cold Spring Harbor Laboratory (1982).
Miller, J. H., *Experiments in Molecular Genetics.*, Cold Spring Harbor Laboratories, Cold Spring Harbor, N.Y. (1972).
Mullis, K., U.S. Pat. No. 4,683,202, issued Jul. 28, 1987.
Mullis, K., et al., U.S. Pat. No. 4,683,195, issued Jul. 28, 1987.
Reyes, G., et al, Science, 247:1335 (1990).
Sanger, F., et al., Proc. Natl. Acad. Sci. USA 74:5463 (1977).
Scharf, S. J., et al., Science 233:1076 (1986).
*Selected Method in Cellular Immunology*, (Mishell, B. D., et al. eds) W. H. Freeman and Co., pp416–440 (1980).
Smith. D. B., et al, Gene, 67:31 (1988).
Southern, E., Methods in Enzymology 69:152 (1980).
Tijssen, P., *Practice and Theory of Immunoassays*, Scientific Publishing Co., NY, N.Y., 1985, p. 335.
Wilson, W., et al., Cell 55:1159–1169 (1988).
Woo, S. L. C., Methods in Enzymology 68:389 (1979).
Young, R. A. and R. W. Davis, Proc. Natl. Acad. Sci. USA 80, 1194–1198 (1983).

3. BACKGROUND

Viral hepatitis resulting from a virus other than hepatitis A virus (HAV) and hepatitis B virus (HBV) has been referred to as non-A, non-B hepatitis (NANBH). More recently, it has become clear that NANBH encompasses at least two, and perhaps more, quite distinct viruses. One of these, known as enterically transmitted NANBH or ET-NANBH, is contracted predominantly in poor-sanitation areas where food and drinking water have been contaminated by fecal matter. The molecular cloning of a portion of this virus, referred to as the hepatitis E virus (HEV), has recently been described (Reyes et al.).

The second NANB virus type, known as parenterally transmitted NANBH, or PT-NANBH, is transmitted by parenteral routes, typically by exposure to blood or blood products. Approximately 10% of transfusions cause PT-NANBH infection, and about half of these go on to a chronic disease state (Dienstag).

Human sera documented as having produced post-transfusion NANBH in human recipients has been used successfully to produce PT-NANBH infection in chimpanzees (Bradley). RNA isolated from infected chimpanzee sera has been used to construct cDNA libraries in an expression vector for immunoscreening with chronic-state human PT-NANBH serum. This procedure identified a PT-NANBH specific cDNA clone and the viral sequence was then used as a probe to identify fragments making up 7,300 contiguous basepairs of a PT-NANBH viral agent (EPO patent application 88310922.5, filed Nov. 18, 1988). The same procedure was used by the present inventors to derive two of the PT-NANBH peptide and polynucleotide sequences disclosed herein. The sequenced viral agent has been named HCV (HCV) (above EPO patent application).

Heretofore, one immunogenic peptide encoded by the HCV viral agent has been reported (Choo, Kuo, EPO application 88310922.5). This peptide, designated C-100, has been used in immunoassays of PT-NANBH sera and found to react immunospecifically with up to 80% of chronic NANBH samples, and about 15% of acute NANBH samples (Kuo).

It is desirable to provide one or a collection of peptide antigens which are immunoreactive with a greater percentage of PT-NANBH-infected blood, including both acute and chronic PT-NANBH infection.

4. SUMMARY OF THE INVENTION

It is one general object of the invention to provide recombinant polypeptides immunoreactive with sera from humans infected with hepatitis C virus (HCV), including a peptide which is immunoreactive with a high percentage of sera from chronic HCV-infected individuals, and peptides which are immunoreactive with sera associated with acute HCV infection.

It is another object of the invention to provide an HCV polynucleotide sequence encoding a sequence for recombinant production of the peptide antigens, and a diagnostic method for detecting HCV-infected human sera using the peptide antigens.

The invention includes, in one aspect, a peptide antigen which is immunoreactive with sera from humans infected with HCV. One peptide antigen in the invention includes an immunoreactive portion of an HCV polypeptide which:

a) is encoded by an HCV coding sequence;

b) has 504 amino acid residues; and c) has the carboxy-terminal sequence presented as SEQ ID NO:4.

Other peptide antigens of the invention include an immunoreactive portion of any one of the following sequences:

SEQ ID NO:2, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, and SEQ ID NO:26.

In another aspect, the invention includes diagnostic kits for use in screening human blood containing antibodies specific against HCV infection. The kit includes at least one peptide antigen which is immunoreactive with sera from humans infected with hepatitis C virus (HCV): specific peptide antigens for use in the kit are given above.

One preferred embodiment of the present invention is a diagnostic kit containing the 409-1-1(c-a) (SEQ ID NO:8) and one of the HCV-capsid derived proteins (SEQ ID NOs:12, 14, 16, 18, 20, 22, 24, and 26): two particular embodiments being 409-1-1(c-a) with the C1NC 450 capsid-derived peptide, and 409-1-1(c-a) with the C1NC 360 capsid-derived peptide.

In one embodiment of the present invention, the antigen is immobilized on a solid support. The binding of HCV-specific antibodies to the immobilized antigen is detected by a reporter-labeled anti-human antibody which acts to label the solid support with a detectable reporter.

The kit is used in a method for detecting HCV infection in an individual by: (i) reacting serum from an HCV-infected test individual with the above peptide antigen, and (ii) examining the antigen for the presence of bound antibody.

The peptide antigens are produced, in accordance with another aspect of the invention, using an expression system for expressing a recombinant peptide antigen which is immunoreactive with sera from humans infected with hepatitis C virus (HCV). A selected expression vector containing an open reading frame (ORF) of a polynucleotide which encodes the peptide is introduced into a suitable host, which is cultured under conditions which promote expression of the ORF in the expression vector.

In one embodiment, the polynucleotide is inserted into an expression site in a lambda gt11 phage vector, and the vector is introduced into an *E. coli* host. The following *E. coli* hosts have been deposited which contain vectors including the coding sequences of the antigens shown in parenthesis: ATCC No 40901 (SEQ ID NO:3), ATCC NO. 40893 (SEQ ID NO:1), and ATCC No. 40792 (SEQ ID NO:7), and ATCC No. 40876 (SEQ ID NO:9). pGEX and pET are two other vectors which have been used to express HCV antigens. It will be appreciated that determination of other appropriate vector and host combinations for the expression of the above sequences are within the ability of one of ordinary skill in the art.

Also forming part of the invention are polynucleotides which encode polypeptides immunoreactive with sera from humans infected with hepatitis C virus (HCV). One polynucleotide of the present invention encodes a polypeptide wherein the polypeptide includes an immunoreactive portion of a peptide sequence which:

a) is encoded by an HCV coding sequence;
b) has 504 amino acid residues; and
c) has the carboxy-terminal sequence presented as SEQ ID NO:4; and, where the carboxy-terminal amino acid sequence of said peptide antigen is encoded by the polynucleotide sequence presented as SEQ ID NO:3.

Other polynucleotides of the invention include any one of the following sequences: SEQ ID NO:1, SEQ ID NO:3, SEQ ID NO: 5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:25.

These and other objects and features of the invention will become more fully apparent when the following detailed description is read in conjunction with the accompanying drawings.

5. BRIEF DESCRIPTION OF THE DRAWINGS

FIG. 3 shows the DNA coding sequence of the clone 40 insert. The underlined sequences correspond to an $R_9$ primer region.

FIG. 4 shows the DNA coding sequence of a clone 36 insert. The underlined sequences correspond, respectively, to the $F_7$, $F_8$, and $R_8$ primer regions.

FIG. 5 shows the DNA and protein coding sequences for a 409-1-1(abc) clone insert. The "A" region of this sequence is delineated by boxes, the "B" region by a box and a triangle, and the "C" region by a triangle and an asterisk.

FIGS. 6A and 6B show the DNA and protein coding sequences for a 409-1-1(c-a) clone insert.

FIG. 8A shows the DNA and protein coding sequences for the pGEX-GG1 insert. The three G's above the first line indicate where substitutions were made to generate the clone pGEX-CapA. FIGS. 8B and 8C shows the DNA and protein sequences for the pGEX-CapA insert coding sequence. The primers used in polymerase chain reactions to generate carboxy and amino terminal deletions are indicated below the nucleotide line. The sequences of the primers are indicated in the sense (coding strand). The actual sequence of the NC (non-coding), primers is the reverse complement of the indicated sequence. Coding primers are underlined; reverse (noncoding) primers are double-under-lined. Sequences shown in capital letters are exact matches. Sequences in lowercase letters are "mismatched" sequences used to introduce the terminal restriction sites (NcoI at the 5' ends and BamHI at the 3' ends). The three nucleotides which have been altered to remove the "slippery codons" at positions 24, 27, and 30 are indicated by bold type with the wild type A residues shown above the sequence.

Figure 9:
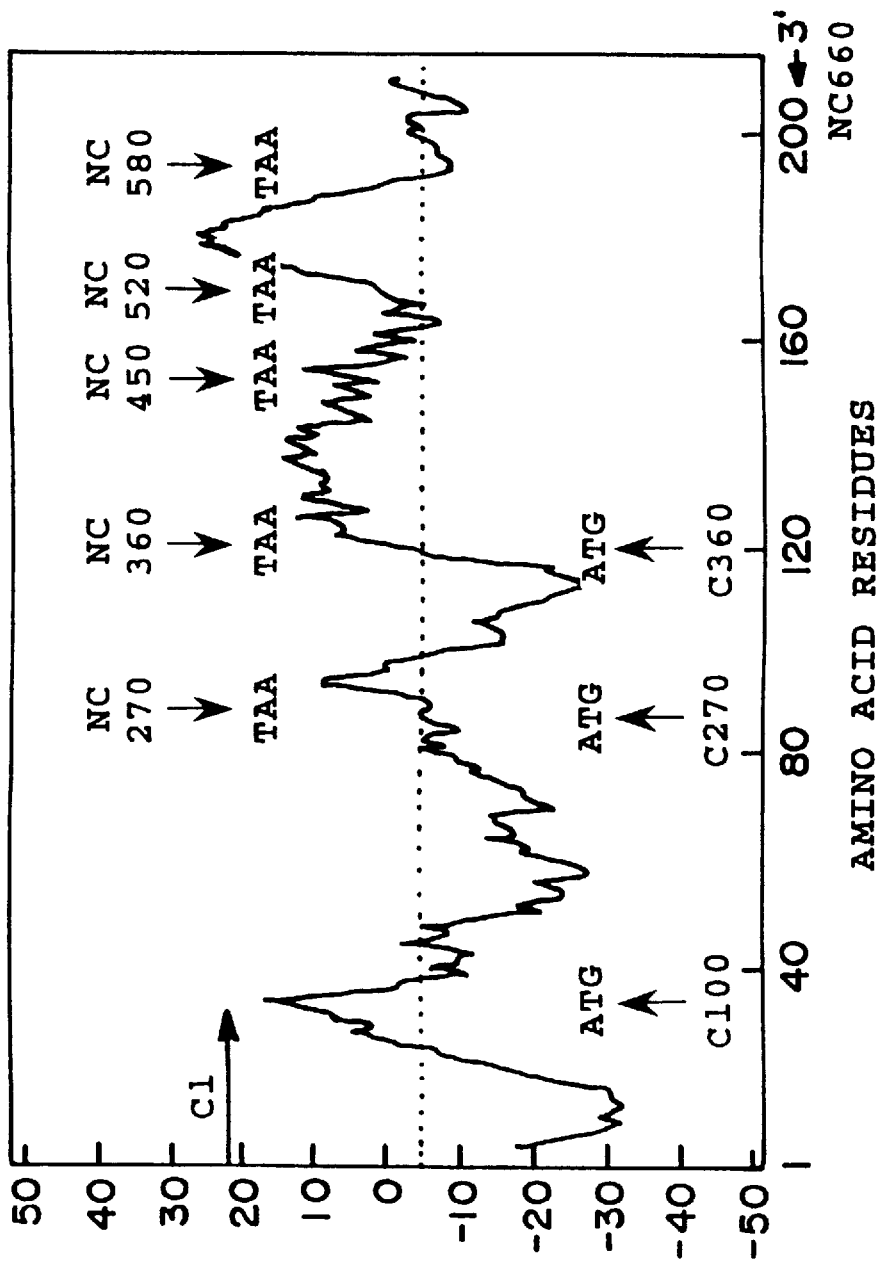

FIG. 9 shows a hydropathicity plot of the HCV-core protein encoded by pGEX-CapA. The relative location of the primers, used to generate carboxy and amino terminal deletions, are indicated relative to the protein coding sequence by arrows.

FIG. 10 shows an epitope map of the HCV capsid protein region.

6. DETAILED DESCRIPTION OF THE INVENTION

I. Definitions

The terms defined below have the following meaning herein:

1. "Parenterally transmitted non-A, non-B hepatitis viral agent (PT-NANBH)" means a virus, virus type, or virus class which (i) causes parenterally transmitted infectious hepatitis, (ii) is transmissible in chimpanzees, (iii) is serologically distinct from hepatitis A virus (HAV), hepatitis B virus (HBV), and hepatitis E virus (HEV).

2. "HCV (HCV)" means a PT-NANBH viral agent whose polynucleotide sequence includes the sequence of the 7,300 basepair region of HCV given in the Appendix, and variations of the sequence, such as degenerate codons, or variations which may be present in different isolates or strains of HCV.

3. Two nucleic acid fragments are "homologous" if they are capable of hybridizing to one another under hybridization conditions described in Maniatis et al., op. cit., pp. 320–323, using the following wash conditions: 2×SCC, 0.1% SDS, room temperature twice, 30 minutes each; then 2×SCC, 0.1% SDS, 50° C. once, 30 minutes; then 2×SCC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash or hybridization conditions for identification of clones from gene libraries (or other sources of genetic material), as is well known in the art.

4. A DNA fragment is "derived from" HCV if it has substantially the same basepair sequence as a region of the HCV viral genome which was defined in (2) above.

5. A protein is "derived from" a PT-NANBH or HCV viral agent if it is encoded by an open reading frame of a cDNA or RNA fragment derived from a PT-NANBH or HCV viral agent, respectively.

II. Molecular Clone Selection by Immunoscreening

As one approach toward identifying a molecular clone of a PT-NANBH agent, cDNA libraries are prepared from infected sera in the expression vector lambda gt11. cDNA sequences are then selected for expression of peptides which are immunoreactive with PT-NANBH-infected sera. Recombinant proteins identified by this approach provide candidates for peptides which can serve as substrates in diagnostic tests. Further, the nucleic acid coding sequences identified by this approach serve as useful hybridization probes for the identification of further PT-NANBH coding sequences.

In order to make immunoscreening a useful approach for identifying clones originating from PT-NANBH coding sequences, a well-defined source of PT-NANBH virus is important. To generate such a source, a chimpanzee (#771; Example 1A) was infected with transmissible PT-NANBH agents using a Factor VIII concentrate as a source (Bradley). The Factor VIII concentrate was known to contain at least two forms of parenterally transmitted NANB hepatitis (PT-NANBH). In addition to a chloroform-sensitive agent, which has subsequently been called HCV (HCV), a chloroform-resistant form of PT-NANBH was also transmitted in the concentrate (Bradley, 1983):

In the method illustrated in Example 1, infected serum was pelleted, without dilution, by centrifugation, and cDNA libraries were generated from the resulting pelleted virus (Example 1B and 1C). Sera from infected human sources were treated in the same fashion. cDNA libraries were generated, e.g., by a random primer method using the RNA extracted from pelleted sera as starting material (Example 1B and 1C). The resulting cDNA molecules were then cloned into a suitable vector, for example, lambda gt11, for expression and screening of peptide antigens, and lambda gt10, for hybridization screening (Example 1C(iv)). Lambda gt11 is a particularly useful expression vector which contains a unique EcoRI insertion site 53 base pairs upstream of the translation termination codon of the beta-galactosidase gene. Thus, an inserted sequence is expressed as a beta-galactosidase fusion protein which contains the N-terminal portion of the beta-galactosidase gene, the heterologous peptide, and optionally the C-terminal region of the beta-galactosidase peptide (the C-terminal portion being expressed when the heterologous peptide coding sequence does not contain a translation termination codon). This vector also produces a temperature-sensitive repressor (cI857) which causes viral lysogeny at permissive temperatures, e.g., 32° C., and leads to viral lysis at elevated temperatures, e.g., 42° C. Advantages of this vector include: (1) highly efficient recombinant clone generation, (2) ability to select lysogenized host cells on the basis of host-cell growth at permissive, but not non-permissive, temperatures, and (3) high levels of recombinant fusion protein production. Further, since phage containing a heterologous insert produces an inactive beta-galactosidase enzyme, phage with inserts are typically identified using a beta-galactosidase colored-substrate reaction.

In the screening procedure reported in Examples 1–3, individual cDNA libraries were prepared from the serum of one PT-NANBH infected chimpanzee (#771) and four PT-NANBH infected humans (designated EGM, BV, WEH, and AG). These five libraries were immunoscreened using PT-NANBH positive human or chimpanzee sera (Example 2): 111 lambda gt11 clones were identified which were immunoreactive with at least one of the sera. Of these 111 clones, 93 were examined for insert hybridization with normal DNA. The inserts were radioactively labelled and used as probes against HindIII/EcoRI doubly-digested human peripheral lymphocyte (PBL) DNA (Example 3). Approximately 46% (43/93) of the inserts hybridized with normal human PBL DNA and were therefore not pursued. Inserts from 11 PT-NANBH-immunopositive clones derived from chimpanzee #771 sera were characterized as exogenous to normal human PBL DNA (Example 3). Of these 11 clones 2 PT-NANBH clones were identified having the following characteristics. One clone (clone 40) was clearly exogenous by repeated hybridization tests against normal human PBL DNA, had a relatively small insert size (approximately 0.5 kilobases), and was quite unreactive with negative control serum. The second clone (clone 36) was shown to be reactive with multiple PT-NANBH antisera, had a relatively large insert size (approximately 1.5 kilobases), and was exogenous by hybridization testing against normal human PBL DNA. The immunoreactive characteristics of clones 36 and 40 are summarized in Table 1 (Example 3). Clone 36 was immunoreactive with chimpanzee #771 sera and two HCV-positive human sera, AG and BV. The clone 36 antigen did not immunoreact with the negative control sera SKF. Clone 40 was immunoreactive with chimpanzee #771 sera and was cleanly nonreactive when the negative control sera was used for screening.

The DNA sequence of clone 36 was determined in part and is shown in FIG. 4. This sequence corresponds to nucleotides 5010 to 6516 of the HCV sequence given in the Appendix. The DNA sequence was also determined for the clone 40 insert (FIG. 3). This sequence is homologous to the HCV sequence (Appendix) in the region of approximately nucleotides 6515 to 7070. The inserts of two other chimpanzee #771 clones, clones 44 and 45, were found to be homologous to clone 40 by hybridization and sequence analysis (Example 4). The sequences for clones 36 and 40 are contiguous sequences, with the clone 36 sequences being located 5' of the clone 40 sequences as presented in the Appendix. Accordingly, these two clones represent isolation of a significant block of the HCV genome by the above-described immunoscreening methods.

The four lambda gt11 clones 36, 40, 44, and 45 were deposited in the Genelabs Culture Collection, Genelabs Incorporated, 505 Penobscot Drive, Redwood City, Calif. 94063. Further, the lambda gt11 clones of clones 36 and 40 were deposited with the American Type Culture Collection, 12301 Parklawn Dr., Rockville Md., 20852, and given the deposit numbers ATCC No. 40901 and ATCC 40893.

III. PT-NANBH Sequence Identification by Hybridization Methods

The polynucleotides identified in Section II can be employed as probes in hybridization methods to identify further HCV sequences, and these can then be used as probes to identify additional sequences. The polynucleotides can be directly cloned or fragmented by partial digestion to generate random fragments. The resulting clones can be immunoscreened as described above to identify HCV antigen coding sequences.

To illustrate how the inserts of clones 36 and 40 can be used to identify clones carrying HCV sequences, the insert of clone 40 was isolated and used as a hybridization probe against the individual cDNA libraries established in lambda gt10 (see above). Using the clone 40 probe approximately 24 independent hybridization-positive clones were plaque purified (Example 5). The positive signals arose with different frequencies in cDNA libraries from the different serum sources, suggesting that the hybridization signals were from the serum sources, rather than resulting from some common contaminant introduced during the cDNA synthesis or cloning (Table 2). One of the clones, 108-2-5, which tested positive by hybridization with the clone 40 insert, had an insert of approximately 3.7 kb (Example 6). Since it had such a large insert, clone 108-2-5 was chosen for further analysis. The serum source of this cDNA clone was EGM human PT-NANBH serum (Example 1).

The insert of 108-2-5 was isolated by EcoRI digestion of the lambda gt10 clone, electrophoretic fractionation, and electroelution (Example 6). The isolated insert was treated with DNase I to generate random fragments (Example 6), and the resulting digest fragments were inserted into lambda gt11 phage vectors for immunoscreening. The lambda gt11 clones of the 108-2-5 fragments were immunoscreened (Example 6) using human (BV and normal) and chimpanzee #771 serum. Twelve positive clones were identified by first round immunoscreening with the human and chimp sera. Seven of the 12 clones were plaque purified and rescreened using chimpanzee #771 serum. Partial DNA sequences of the insert DNA were determined for two of the resulting clones, designated 328-16-1 and 328-16-2. These two clones contained sequences essentially identical to clone 40 (Example 6).

The clone 36 insert can be used in a similar manner to probe the original cDNA library generated in lambda gt10. Specific subfragments of clone 36 may be isolated by Polymerase chain reaction or after cleavage with restriction endonucleases. These fragments can be radioactively labelled and used as probes against the cDNA libraries generated in lambda gt10 (Example 1C). In particular, the 5' terminal sequences of the clone 36 insert are useful as probes to identify clones overlapping this region.

Further, the sequences provided by the terminal clone 36 insert sequences and the terminal clone 40 insert sequences are useful as specific sequence primers in first-strand DNA synthesis reactions (Maniatis et al.; Scharf et al.) using, for example, chimpanzee #771 sera generated RNA as substrate. Synthesis of the second-strand of the cDNA is randomly primed. The above procedures identify or produce cDNA molecules corresponding to nucleic acid regions that are 5' adjacent to the known clone 36 and 40 insert sequences. These newly isolated sequences can in turn be used to identify further flanking sequences, and so on, to identify the sequences composing the HCV genome. As described above, after new HCV sequences are isolated, the polynucleotides can be cloned and immunoscreened to identify specific sequences encoding HCV antigens.

IV. Generating Overlapping Cloned Linking Fragments

This section describes a method for producing and identifying HCV peptides which may be useful as HCV-diagnostic antigens. The present method is used to generate a series of overlapping linking fragments which span a segment of nucleic acid. The application of the method to generating a series of overlapping linking fragments which span a 7,300 basepair segment of the HCV genome, whose sequence is given in the FIGS 11A to 11H, will be described with reference to FIGS. 1 and 2.

Figure 1:
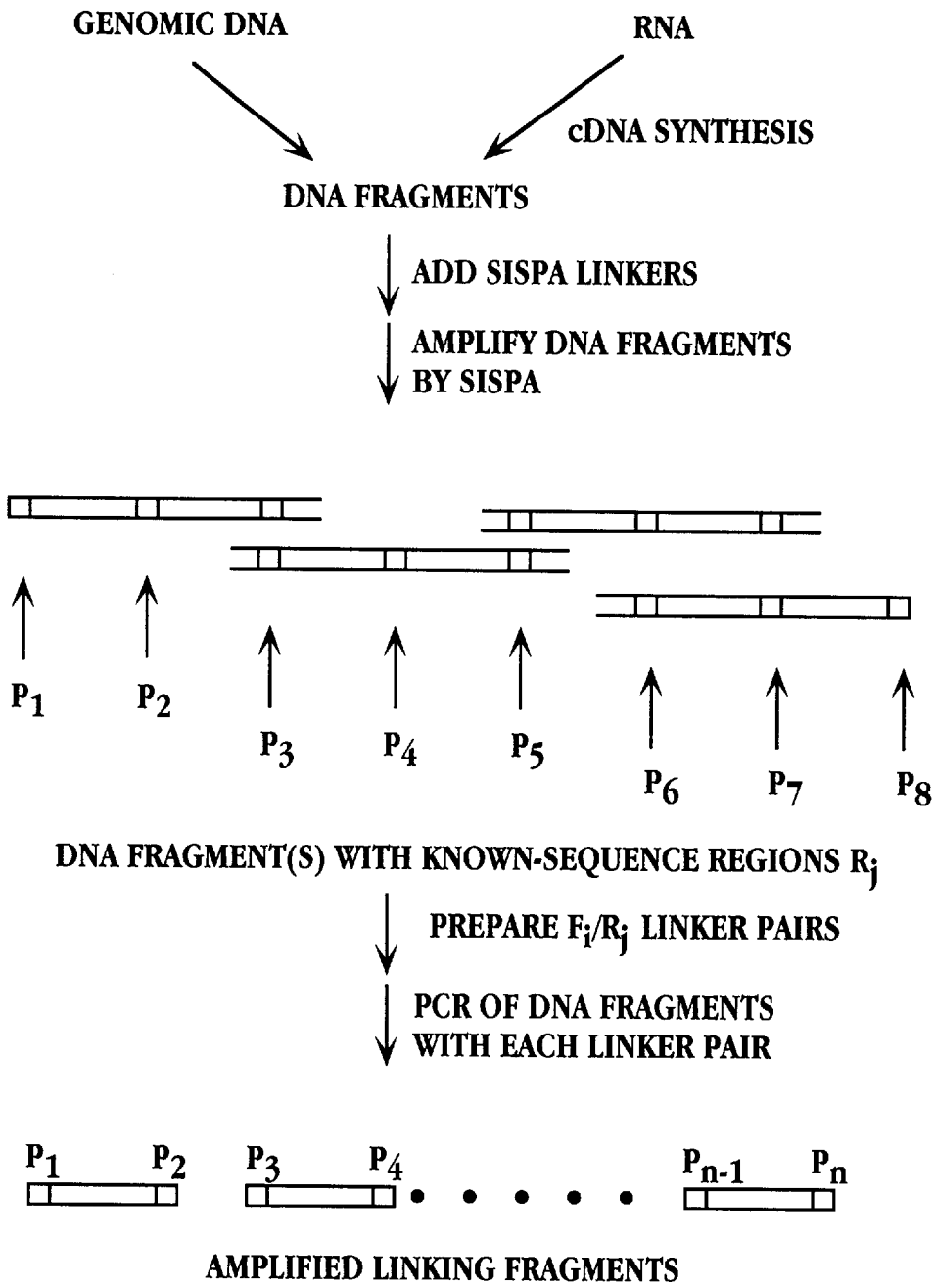
FIG. 1 illustrates the steps in producing overlapping linking fragments of a nucleic acid segment, in accordance with the methods of the present invention.

As a first step in the method, and with reference to FIG. 1, the nucleic acid of interest is obtained in double-strand DNA form. Typically, this is done by isolating genomic DNA fragments or by producing cDNAs from RNA species present in a sample fluid. The latter method is used to generate double-strand DNA from NANBH viral RNA present in serum from chimpanzees or humans with known PT-NANBH infection. Here RNA in the sample is isolated, e.g., by guanidinium thiocyanate extraction of PEG precipitated virions, and reacted with a suitable primer for first strand cDNA synthesis.

First-strand cDNA priming may be by random primers, oligo dT primers, or sequence-specific primer(s). The primer conditions are selected to (a) optimize generation of cDNA fragments which collectively will span the nucleic acid segment of interest, and (b) produce cDNA fragments which are preferably equal to or greater than about 1,000 basepairs in length. In one method applied to HCV RNA, the first-strand synthesis is carried out using sequence-specific primers which are complementary to spaced regions along the length of the known HCV genomic sequence. The primer position are indicated at A, B, C, and D in FIG. 2, which shows a map of the HCV genome segment. The basepair locations of the primers in the HCV genome are given in Example 7 below. Following first strand synthesis, the second cDNA strand is synthesized by standard methods.

The linking fragments in the method are produced by sequence-specific amplification of the double-strand DNA obtained as above, using pairs of overlap-region primers to be described. According to an important advantage of the methods of the present invention, it is possible to generate linking fragments even when the amount of double-strand DNA is too low for direct sequence-specific amplification. This limitation was found, for example, with HCV cDNA's produced from NANBH-infected serum. Here the amount of double-stranded DNA available for amplification is first amplified nonspecifically by a technique known as Sequence-Independent Single-Primer Amplification (SISPA).

The SISPA technique is detailed in co-owned U.S. Patent application for "RNA and DNA Amplification Techniques", Ser. No. 224,961, filed Jul. 26, 1988. The method as applied to amplification of HCV cDNA fragments is also described in Example 7. Briefly, known-sequence linker primers are attached to opposite ends of double-stranded DNA in a DNA sample. These linkers then provide the common end sequences for primer-initiated amplification, using primers complementary to the linker/primer sequences. Typically, the SISPA method is carried out for 20–30 cycles of amplification, using thermal cycling to achieve successive denaturation and primer-initiated polymerization of second strand DNA.

FIG. 1 illustrates the SISPA amplification of duplex DNA, to form amplified fragments which have known-sequence regions $P_i$. As seen, the fragment mixture includes at least some fragments which (a) overlap at regions $P_i$ with other fragments in the mixture and (b) contain complete linking regions between adjacent $P_i$ and $P_{i+1}$ regions. Collectively, each linking region bounded by the associated overlap regions making up the segment is present in at least one DNA fragment.

Figure 2:
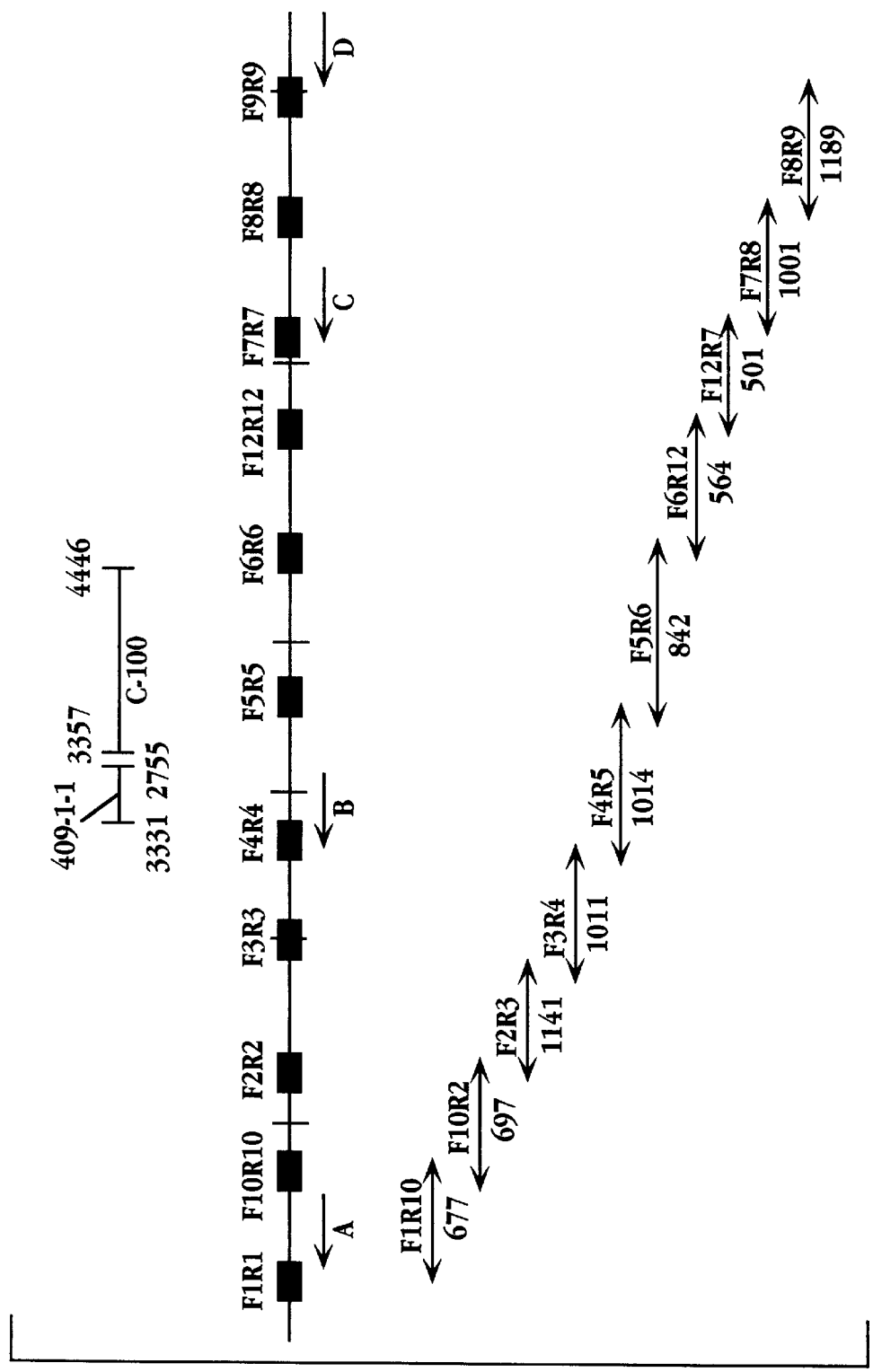
FIG. 2 shows the positions of overlap primer regions and linking regions along a 7,300 basepair portion of the HCV genome.

The production of overlapping linking fragments, in accordance with the methods of the present invention, is carried out using the polymerase chain reaction (PCR) method described in U.S. Pat. No. 4,683,195. In practicing this step of the method, first the total segment of interest is divided into a series of overlapping intervals bounded by regions of known sequence, as just described. In FIG. 2, the 7,300 basepair segment of the HCV genome has been divided into 10 intervals, each about 500–1,000 basepairs in length. The intervals are designated according to the forward $F_i$ and reverse $R_j$ primers used in amplifying the sequence, as will be described. The selection of the intervals is guided by (a) the requirement that the basepair sequence at each end of the interval be known, and (b) a preferred interval length of between about 500 and 2,000 basepairs.

In the method applied to the 7,300 basepair segment of the HCV genome, the regions of overlap between the ten intervals were additionally amplified, to verify that the SISPA-amplified cDNA sample contained sufficient HCV cDNA to observe PCR-amplification of HCV linking fragments, and that HCV regions along the entire length of the genome were available for amplification. Each overlap region in the segment can be defined by a pair of primers which includes a forward primer $F_i$ and a reverse primer $R_i$ which are complementary to opposite strands of opposite ends of the overlap region. The primers are typically about 20 basepairs in length and span an overlap region of about 200 basepairs. The eleven overlap regions in the HCV segment and the regions corresponding to the forward and reverse primers in each region are given in example 8.

The primers $F_i/R_i$ are added to the amplified DNA material in a PCR reaction mix, and the overlap region bounded by the primers is amplified by 20—30 thermal cycles. The reaction material is then fractionated, e.g., by agarose gel electrophoresis, and probed for the presence of the desired sequence, e.g., by Southern blotting (Southern), using a radiolabeled oligonucleotide probe which is specific for an internal portion of the overlap region. As described in Example 8, this method was successful in producing amplified fragments for each of the eleven $F_i/R_i$ overlap regions in the HCV genome segment. The overlap-region fragments may be used as probes for the corresponding (two) linking fragments connected by the overlap region. It is emphasized, however, that this amplification step was employed to confirm the presence of amplifiable cDNA along the length of the HCV genome, and not as an essential step in producing the desired linking fragments. The step is omitted from FIG. 1.

The linking fragments $F_i/R_j$ are produced by a two-primer PCR procedure in which the SISPA-amplified DNA fragments are amplified by a primer pair consisting of the forward primer $F_i$ of one overlap region and the reverse primer $R_j$ of an adjacent overlap region. The ten overlap regions in the HCV segment and the regions corresponding to the forward and reverse primers in each region are given in Example 9. Typical amplification conditions are give in Example 9. The amplified fragments in each reaction mixture are isolated and purified, e.g., by gel electrophoresis, to confirm the expected fragment size. Southern blots may be probed with oligonucleotide probes complementary to internal regions located between the fragment ends, to confirm the expected sequence of the fragments. As shown at the bottom in FIG. 1, the method generates the complete set of linking fragments, where each fragment is bounded by an overlap region $P_i$ and $P_{i+1}$.

The method, as applied to generating ten overlapping linking fragments of the 7,300 basepair HCV genome, is described in Example 9. As demonstrated by size criteria on gel electrophoresis and by sequence criteria by Southern blotting, the method was successful in generating all ten of the overlapping fragments spanning the HCV genome.

It will be appreciated that the above flanking sequence amplification method can be applied to the generation of DNA fragments corresponding to the insert sequences of clones 36 and 40, which have also been obtained by immunoscreening. The linker primers flanking the inserts are easily used to generate sequences corresponding to the clone inserts. For example, two-primer amplification of the SISPA-amplified cDNA fragments (Example 7) using the $F_{12}/R_9$ primer pair (the sequences of which are given in Example 8) is carried out under conditions similar to those described in Example 9. The amplified fragment mixture is fractionated by agarose electrophoresis on 1.0% agarose, and the expected band cut from the gel and eluted.

The purified amplified fragment is treated with the Klenow fragment of DNA polymerase I to assure the molecules are blunt-ended. The fragment is then ligated to EcoRI linkers (Example 10). The mixture is digested with EcoRI and inserted into the lambda gt11 vector. The resulting clones contain the entire coding sequences of either the clone 36 or clone 40 inserts.

Alternatively, the original amplified 36/40 fragment (primers $F_{12}/R_9$) is briefly treated with Exonuclease III (Boehringer Mannheim, as per manufacturer's instructions) to generate a family of fragments with different 5' ends. The digestion products are treated as above and ligated into the lambda gt11 vector. The resulting plaques are then immunoscreened.

Further, different sets of primers, other than the $F_{12}/R_9$ primers described above, can be used to directly generate sequence encoding all, or portions, of clones 36 and 40. For example, primers $F_8/R_9$ can generate a fragment corresponding to a portion of the 3' sequences of the insert of clone 36 (FIG. 4) and all of the insert sequences of clone 40 (FIG. 3). Also, primers $F_7/R_9$ can be used to directly generate a fragment corresponding to a portion of the 5' sequences present in the insert of clone 36 (FIG. 4).

V. PT-MANBH Immunoreactive Peptide Fragments

Several novel peptide antigens which are immunoreactive with sera from human and chimpanzee NANBH-infected sera have been generated from the NANBH linking fragments produced above, in accordance with the methods of the present invention. Further, this method has confirmed antigenic regions previously identified by cDNA library immunoscreening (Section II above). The antigen peptides derived from linking fragments are preferably produced in a method which involves first digesting each of the above linking fragments with DNaseI under partial digestion conditions, yielding DNA digest fragments predominantly in the 100–300 basepair size range, as illustrated in Example 10. The digest fragments may be size fractionated, for example by gel electrophoresis, to select those in the desired size range.

The digest fragments from each linking fragment are then inserted into a suitable expression vector. One exemplary expression vector is lambda gt11, the advantages of which have been described above.

For insertion into the expression vector, the digest fragments may be modified, if needed, to contain selected restriction-site linkers, such as EcoRI linkers, according to conventional procedures. Typically, the digest fragments are blunt-ended, ligated with EcoRI linkers, and introduced into EcoRI-cut lambda gt11. Such recombinant techniques are well known in the art (e.g., Maniatis et al.).

The resulting viral genomic library may be checked to confirm that a relatively large (representative) library has been produced for each linking fragment. This can be done, in the case of the lambda gt11 vector, by infecting a suitable bacterial host, plating the bacteria, and examining the plaques for loss of beta-galactosidase activity, as evidenced by clear plaques.

The presence of a digest-fragment insert in the clear plaques can be confirmed by amplifying the phage DNA, using primers specific for the regions of the gt11 phage flanking the EcoRI insert site, as described in Example 10B. The results in Table 3 show that a large percentage of the plaques tested in each linking fragment library contained a digest-fragment insert.

The linking-fragment libraries may also be screened for peptide antigens which are immunoreactive with human or chimpanzee sera identified with PT-NANBH chronic, convalescent, or acute infection. One preferred immunoscreening method is described in Example 10B. Here recombinant protein produced by the phage-infected bacteria is transferred from the plaques to the filter. After washing, the filter is incubated with test serum, and then reacted with reporter-labeled anti-human IgG antibody. The presence of the peptide antigen on the filter is then assayed for the presence of the reporter. As seen from Table 3, several of the linking-fragment libraries were positive for immunoreactive peptides in the primary screen.

The immunoscreening method just described can be used to identify library plaques from each of the linking libraries which are immunoreactive with sera from human or chimpanzee with known chronic, convalescent, or acute PT-NANBH infection. One exemplary screening procedure is given in Example 11, where the ten HCV linking-fragment libraries are screened with known PT-NANBH (a) human chronic serum, (b) chimpanzee acute pooled sera and (c) chimpanzee chronic pooled sera. Of the ten libraries examined, only the $F_1/R_{10}$ library did not give positive immunoreaction with any of the three sera. Several of the fragment libraries, including $F_3/R4$, $F_6/R_{12}$, $F_{12}/R_7$, and $F_7/R_8$ showed five or more positive reactions with chimpanzee acute sera, indicating that these libraries each express one or more peptide antigens which are useful for detecting chimpanzee or human acute PT-NANBH infection.

The fragment library $F_7/R_8$ corresponds to an internal fragment of clone 36 insert (Section II; FIG. 4). Accordingly, the linking fragment method confirmed that this DNA region encodes a useful antigen. Further, the fragment library $F_8/R_9$ contains the sequences present in the clone 40 insert (Section II: FIGS. 3 and 4). The results in Table 4 indicate that at least one peptide antigen effective to detect the presence of chronic-infection serum was isolated from the $F_8/R_9$ fragment library.

VI. Immunoreactive 409-1-1 Peptides

A. Immunoreactive Screening

Two of the immunoreactive plaques identified by immunoreactive screening, designated 409-1-1(abc) and 409-1-1 (c-a), were tested for immunoreactivity against well-documented PT-NANBH chronic sera which showed strong immunoreactivity to the 5-1-1 HCV peptide antigen (Kuo). The 5-1-1 HCV peptide antigen has previously been identified as immunoreactive against a high percentage of human PT-NANBH chronic sera. The 5-1-1 antigen is encoded by the sequence between basepairs 3731 and 3857 in the HCV genome (Appendix) and is itself contained in a larger peptide antigen C-100 encoded by the sequence between basepairs 3531 and 4442. The latter peptide is employed in a commercial diagnostic kit for detection of human HCV infection (Ortho/Chiron). The kit is reported to react positively with about 80% of human chronic PT-NANBH samples, and about 15% of human acute PT-NANBH sera, as noted above.

The 409-1-1 (c-a) phage was identified by immunoscreening and plaque purified, as outlined above. A related clone, designated 409-1-1(abc), was described in the parent to the present application (U.S. application Ser. No. 07/505,611, herein incorporated by reference). Clone 409-1-1(abc) was designated 409-1-1 in the parent application. The a, b and c designations refer to three regions of the 409-1-1(abc) sequence (see FIG. 5). The 5-1-1 coding sequence was isolated by polymerase chain reaction using oligonucleotide primers complementary to the ends of the 5-1-1 coding region, and cloned into lambda gt11 for expression under induction conditions of a fused beta-galactosidase protein which includes the 5-1-1 antigen peptide region. The 5-1-1 phage was identified and plaque purified by similar methods.

The 409-1-1(c-a) arid 5-1-1 antigens were compared by plaque immunoscreening with a panel of 28 sera from normal (2 donors), human PT-NANBH-chronic (6 donors), chimpanzee normal (7 donors), chimpanzee PT-NANBH-acute (5 donors), and chimpanzee PT-NANBH-chronic (8 donors), with the results shown in Table 5 in Example 12. As can be seen in Table 5, the 5-1-1 and 409-1-1(c-a) peptides reacted with most of the human and chimpanzee chronic sera, although the 409-1-1(c-a) peptide detected a higher percentage of human chronic sera samples (83% vs 66%). The chronic human serum which was detected by the 409-1-1(c-a) peptide, but not by 5-1-1 was from a patient (BV) who died of fulminant NANBH infection. Because the 5-1-1 antigen is contained within the C-100 antigen in the commercially available kit format (Ortho/Chiron), it was of interest to determine whether the C-100 antigen gave a broader range of reactivity with the test sera. The results are shown at the right in Table 5 below. The only human NANBH serum that was tested was the above BV serum which was not detected by 5-1-1. This serum was also not immunoreactive with the C-100 antigen (0/1). Nor was the C-100 antigen reactive with any of the five acute chimp sera which were tested (0/5). It is also noted that the 409-1-1(c-a) antigen is immunoreactive with 3 of the 5 acute chimpanzee sera tested, compared with only 1 out of 5 for the 5-1-1 antigen. The results indicate that the 409-1-1(c-a) antigen has broader immunospecificity with PT-NANBH sera, and thus would provide a superior diagnostic agent. The results obtained with 409-1-1(c-a) are comparable to the results obtained using 409-1-1(abc).

It is noted here that the 409-1-1(abc) coding sequence is contained in the $F_4/R_5$ linking fragment and does not overlap the sequence of the C-100 (and 5-1-1) coding region which is in the $F_4/R_5$ and $F_5/R_6$ linking fragments. The relatively long coding sequence of the 409-1-1(abc) peptide illustrates that larger size digest fragments (substantially greater than 300 basepairs) are generated in the partial digest step used in producing digest fragments for antigen expression.

The 409-1-1(abc) peptide, which forms one aspect of the invention, has the amino acid sequence which is presented as SEQ ID NO:10. The DNA coding sequence corresponding to the insert in the 409-1-1 clone is given in FIG. 5 and is presented as SEQ ID NO:9.

The 409-1-1(c-a) peptide, which forms another aspect of the invention, has the amino acid sequence presented as SEQ ID NO:8. The DNA coding sequence corresponding to the insert in the 409-1-1(c-a) clone is given in FIG. 6 and is presented as SEQ ID NO:7. The relationship between the coding sequence of 409-1-1(c-a) and 409-1-1(abc) is outlined in Example 12. Briefly, 409-1-1(c-a) consists of a carboxy terminal region of 409-1-1(abc) moved to the amino terminus of the 409-1-1 coding sequence, with a truncation of the remaining 3' 409-1-1(abc) coding sequence.

More generally, the invention includes a peptide antigen which is immunoreactive with sera from humans with HCV infection. Such peptide antigens are readily identifiable by the methods of the present invention.

Figure 7:
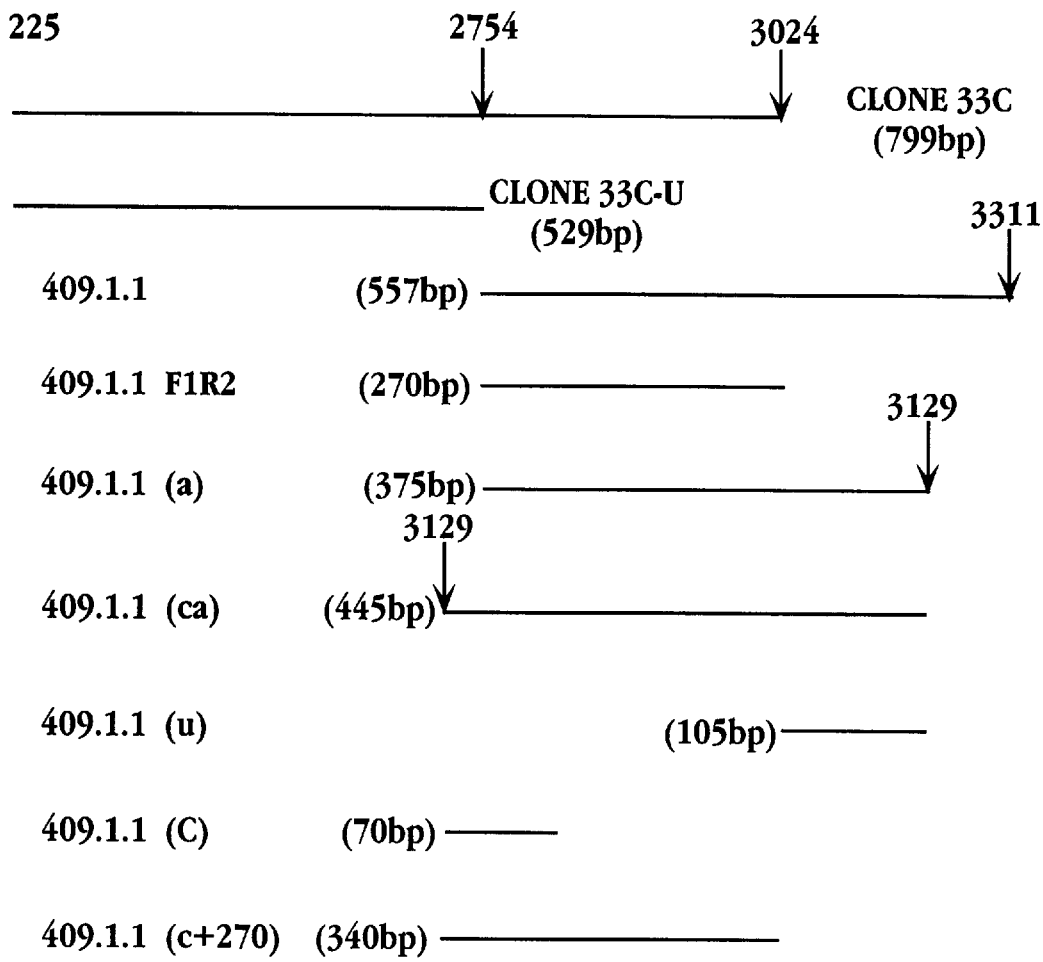
FIG. 7 illustrates the groups of clones which have been obtained from the HCV genome in the region corresponding to the 409-1-1(abc) clone insert.

Antigens obtained from the region corresponding to the HCV sequences encoding the 409-1-1 antigens were further characterized as follows. The primers shown in Table 7 were used to generate a family of overlapping amplified fragments derived from this region. Several templates were used for the DNA amplification reactions (Table 8). The relationships of the coding sequences of the resulting clones to each other are graphically illustrated in FIG. 7. The amplified fragments were then cloned into lambda gt11 vectors (Example 13).

These cloned fragments were then immunoscreened (Example 13). Seven of the nine clones tested positive by preliminary immunoscreening (Table 9). These seven clones were then tested against a more extensive battery of PT-NANBH serum samples, including numerous human clinical samples. The sensitivity of the antigens, in decreasing order, for reactivity with the serum used for screening was as follows: 33cu >33c>409-1-1(c-a)>409-1-1-F1R2>409-1-1(abc)≈409-1-1a>5-1-1>409-1-1(c+270). As can be seen from these results all of the alternative clones, with the exception of 409-1-1(c+270), provided a more sensitive antigen than 5-1-1. However, although 33cu and 33c were very sensitive antigens, in this assay they reacted slightly with serum which was known to be negative for HCV and may therefore be less specific. Accordingly, the 409-1-1 series appears preferable for use as diagnostic antigens since they are more specific to HCV-induced antibodies.

The immunoscreening was extended to include the clone 36 and 45 encoded epitopes: the insert of clone 45 is essentially the same as the insert of clone 40 (Example 4). As can be seen from the results presented in Table 11, the antigens produced by clones 36 and 40, while not as sensitive as 409-1-1(c-a), do yield HCV-specific immunopositive signals with selected samples. Accordingly, the two methods presented in the present invention, (i) immunoscreening of cDNA libraries generated directly from sera-derived RNA, and (ii) immunoscreening of amplified-fragment libraries, can both be seen to be effective methods of identifying cDNA sequences encoding viral antigens. Further, confirmation of the clone 36 and 40 encoded antigens by identification of antigens corresponding to these HCV regions using the amplified-fragment library method validates the usefulness of the amplified-fragment method.

B. Peptide Purification

The recombinant peptides of the present invention can be purified by standard protein purification procedures which may include differential precipitation, molecular sieve chromatography, ion-exchange chromatography, isoelectric focusing, gel electrophoresis and affinity chromatography. In the case of a fused protein, such as the beta-galactosidase fused proteins prepared as above, the fused protein can be isolated readily by affinity chromatography, by passing cell lysis material over a solid support having surface-bound anti-beta-galactosidase antibody. For example, purification of a beta-galactosidase/fusion protein, derived from 409-1-1(c-a) coding sequences, by affinity chromatography is described in Example 14.

A fused protein containing the 409-1-1(a) peptide fused with glutathione-S-transferase (Sj26) protein has also been expressed using the pGEX vector system in E. Coli KM392 cells (Smith). This expression system has the advantage that the fused protein is generally soluble and therefore can be isolated under non-denaturing conditions. The fused Sj26 protein can be isolated readily by glutathione substrate affinity chromatography (Smith). This method of expressing this fusion protein is given in Example 15 and is applicable to any of the other antigen coding sequences described by the present invention.

Also included in the invention is an expression vector, such as the lambda gt11 or pGEX vectors described above, containing the 409-1-1(a) coding sequence and expression control elements which allow expression of the coding region in a suitable host. The coding sequence is contained in the sequence given above corresponding to basepairs 2755–3331 of the HCV genome. The control elements generally include a promoter, translation initiation codon, and translation and transcription termination sequences, and an insertion site for introducing the insert into the vector. In the case of the two vectors illustrated in Example 15, the control elements control the synthesis of the protein which is fused with the heterologous peptide antigen. Such expression vectors can be readily constructed for the other antigen coding sequences described by the present invention.

The lambda gt11 vectors containing the following coding regions have been deposited with The American Type Culture Collection, 12301 Parklawn Dr., Rockville Md., 20852: the 409-1-1(abc) coding region, designated gt11/-409-1-1(abc), ATCC No. 40876; the 409-1-1(c-a) coding region, designated gt11/409-1-1(c-a) ATCC No. 40792; clone 36, designated gt11/36, ATCC No. 40901; and, clone 40, designated gt11/40, ATCC No. 40893. Lambda gt11 clone 409-1-1 (ATCC Designation No. 40792) was accepted by the International Depository authority on Apr. 18, 1990; lambda gt11 clone 409-1-1abc (ATCC Designation No. 40876) was accepted for deposit by the International Depository Authority on Aug. 28, 1990.

VII. Immunoreactive Clones of the HCV-Capsid Antigen

At the 1990 Congress of Hepatology a region of the full-length HCV nucleic acid sequence was presented, nucleotide residues 325–970, containing the HCV non-coding, structural core protein and envelope protein coding sequences as capsid parts of a polyprotein sequence. During the course of experiments performed in support of the present invention, the coding region that corresponds to the capsid protein was more clearly defined.

Polymerase Chain Reaction primers were constructed from selected HCV sequence which would generate amplification products of nucleotides 325–970 of the full length HCV genome (see FIGS. 11A to 11H). These primers, SF2(C) and SR1(C), are presented in Example 16. The primers contained non-complementary sequences which encoded restriction enzyme cleavage sites to facilitate subsequent cloning manipulations. The primers were used in amplification reactions containing SISPA-amplified HCV cDNA molecules (Example 7) as substrate. The resulting amplification products were cloned into the pGEX and pET vectors (Example 16). The pGEX vector allows expression of inserted coding sequences as fusion proteins to the Sj26 protein, glutathione-S-transferase. Insertion into the pET vector allows expression of the inserted coding sequences independent of fusion sequences.

These clones were then immunologically screened using sera known to be reactive with HCV-antigens (Example 17). Several clones in both vectors were identified which were immunoreactive with the anti-HCV sera (in pGEX, clones 14, 15, 56, 60, and 65, Example 17, Table 13). It was observed that the fusion proteins which were produced from the clones in pGEX were smaller than expected.

Clone 15 was selected for scaled up production of the Sj26/HCV-antigen fusion protein. The fusion protein product (approximately 29 kd) was smaller than the expected fusion product (approximately 50 kd, Example 17). Further, the yield of the fusion protein from this preparation was unexpectedly low.

Clones 15 and 56 were chosen for nucleic acid sequencing of the HCV-antigen containing inserts (Example 18). The sequences of the two clones were very similar with the exception that clone 15 had a termination codon starting at nucleotide position 126. This result suggested that the amino terminal 42 amino acids encoded by the HCV insert were immunogenic in regard to the anti-HCV sera used for immunoscreening.

To test the suggestion that the amino terminus of the HCV polyprotein was antigenic, a synthetic oligopeptide was constructed essentially corresponding to amino acid residues 6–24 of FIG. 8A: this peptide had very strong immunoreactivity with anti-HCV sera as tested by ELISA. PCR primers (FIG. 8, C1 and NC105) were designed to generate a clone corresponding to this region (FIG. 10, C1NC 105, SEQ ID NO:25). Three other synthetic peptides were tested, one of which was strongly immunoreactive with anti-HCV sera (amino acid residues 47–74, FIG. 8A) and two which were weakly immunoreactive (amino acid residues 39–60 and 101–121, FIG. 8A). These synthetic peptides confirm the presence of a strong antigenic region at the amino-terminal end of the HCV polyprotein in the capsid protein region.

The sequence of clone 56, designated pGEX-GG1-56, is shown in FIG. 8A and is presented in the sequence listing as SEQ ID NO:11. The sequence shows that the cone has a long open reading frame. When production of the fusion protein was induced, a fusion protein smaller than the expected product was produced, similar in size to the clone 15 product. The nucleotide sequence of the clones revealed a region which is prone to translational frameshifting, AAAAAAAAAA (Atkins et al., Wilson et al.). Such a nucleotide sequence may contribute to the low protein yields when these clones are expressed in *E. coli*. In an effort to improve the level of fusion protein expression the third nucleotide position of several codons through this region was changed to a G resulting in the sequence AGAAGAA-GAA (Example 20): the changes had no effect on the protein coding sequence (amino acid residues 8–10, FIG. 8A). This modified insert was cloned into the pGEX vector and the resulting plasmid named pGEX-CapA.

A hydropathicity plot was generated for the protein coding sequences of the insert of pGEX-GG1 (Example 19, FIG. 9). The results of this analysis indicated that the carboxy-terminal region of the encoded protein, approximately amino acid residues 168–182, had the potential for being a membrane spanning segment. Since it was unlikely that the membrane spanning segment would provide a strong antigen and since overproduction of proteins with these regions can adversely affect the growth of bacterial cells, a series of carboxy terminal deletions were generated from pGEX-CapA (Example 20).

To generate the carboxy terminal deletions PCR primers were designed to be complementary to various regions of the pGEX-CapA insert encoded protein. The primers used to generate the carboxy terminal deletions are given in Table 14 and the location of the primers relative to the insert coding sequence is presented in FIG. 8B and FIG 8C. The carboxy terminal deletion fragments were cloned into the pGEX vector and Sj26/HCV-insert fusion proteins were produced. These fusion proteins were then screened with anti-HCV sera and an epitope map generated for the immunoreactive polypeptides (see FIG. 10). Clones C1NC 270, C1NC 360, and C1NC 450 all expressed high levels of the Sj26/HCV fusion proteins. Further, these fusion proteins all corresponded to the size predicted from their nucleic acid coding sequences. Clones C1NC 520 and C1NC 580 gave poor yields of fusion proteins suggesting that when the hydrophobic region of amino acid residues 168–182 is present it may in part be responsible for the poor protein yields previously obtained.

The deletion analysis was continued to further dissect the antigenic regions of the pGEX-CapA encoded HCV antigen. A series of amino terminal deletions (primers in Table 15) combined with carboxy terminal deletions were generated using PCR primers: the locations of all the primers are illustrated in FIG. 8B.

The results of the deletion analysis are presented in Table 16 and in FIG. 10. These results, combined with the synthetic peptide data presented above, suggest that the capsid protein (which comprises the N-terminus of the HCV polyprotein) has two dominant immunoreactive regions. Both of these immunoreactive regions are useful use as diagnostic antigens. The region comprising the first 35 amino acids spans one of the epitopes and the region spanning residues 34–90 encompasses the other strongly immunoreactive domain.

In summary, all of the pGEX clones containing the N-terminus of the HCV polyprotein and either 34, 90, 120 or 150 residues produced large quantities of fusion protein which was shown to be efficiently recognized by HCV positive sera. Expression of the PCR inserts containing amino acid residues 34–90 was also strongly immunoreactive, whereas inserts encoding residues 90–120 or 90–150 were not immunoreactive, demonstrating that these regions were not recognized by human sera. This result suggests that the regions important for the production of recombinant antigens is contained between residues 1 through 90.

Analyses of the pGEXC1NC 450 protein and the pET360 protein showed that the inclusion of these antigens in Western and ELISA formats permitted the identification of HCV positive sera which had been previously identified as either HCV negative or HCV indeterminate. Accordingly, the inclusion of these epitopes permits the generation of an improved screening system (Example 21).

VIII. Anti-HCV Antigen Antibodies

In another aspect, the invention includes antibodies specific against the recombinant antigens of the present invention. Typically, to prepare antibodies, a host animal, such as a rabbit, is immunized with the purified antigen or fused protein antigen. The host serum or plasma is collected following an appropriate time interval, and this serum is tested for antibodies specific against the antigen. Example 15 describes the production of rabbit serum antibodies which are specific against the 409-1-1 antigens in the Sj26/409-1-1(a) and beta-galactosidase/409-1-1(c-a) fusion protein. These techniques are equally applicable to the other antigens of the present invention.

The gamma globulin fraction or the IgG antibodies of immunized animals can be obtained, for example, by use of saturated ammonium sulfate or DEAE Sephadex, or other techniques known to those skilled in the art for producing polyclonal antibodies.

Alternatively, the purified antigen or fused antigen protein may be used for producing monoclonal antibodies. Here the spleen or lymphocytes from an immunized animal are removed and immortalized or used to prepare hybridomas by methods known to those skilled in the art. To produce a human-human hybridoma, a human lymphocyte donor is selected. A donor known to be infected with an HCV virus (where infection has been shown for example by the presence of anti-virus antibodies in the blood) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary In vitro immunization with peptides can also be used in the generation of human monoclonal antibodies.

Antibodies secreted by the immortalized cells are screened to determine the clones that secrete antibodies of the desired specificity, for example, using the Western blot method described in Example 15.

IX. Utility

A. Diagnostic Method and Kit

The antigens obtained by the methods of the present invention are advantageous for use as diagnostic agents for anti-HCV antibodies present in HCV-infected sera; particularly, the 409-1-1 antigens (409-1-1(abc), 409-1-1(c-a), and related antigens (see Table 9); the clone 36 antigen; and, the clone 40 antigen and the capsid antigen. As noted above, many of the antigens provide the advantage over known HCV antigen reagents 5-1-1 and C-100 in that they are immunoreactive with a wider range of PT-NANBH infected sera, particularly acute-infection sera. This is particularly true of combinations of the 409-1-1 antigens with the HCV-core protein antigens as described in Section VII above. The antigens 409-1-1(c-a) and Cap450 have been combined in an ELISA test kit and tested against HCV test kits produced by Abbott and Ortho. The antigens of the present invention consistently identify more HCV+ samples with a high degree of specificity which is comparable to or better than the Abbott and Ortho test kits.

In one preferred diagnostic configuration, test serum is reacted with a solid phase reagent having a surface-bound HCV antigen (or antigens) obtained by the methods of the present invention, e.g., the 409-1-1(c-a) antigen and the Cap450 antigen. After binding anti-HCV antibody to the reagent and removing unbound serum components by washing, the reagent is reacted with reporter-labeled anti-human antibody to bind reporter to the reagent in proportion to the amount of bound anti-PT-NANBH antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric or calorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigens of the present invention follows conventional methods for preparing homogeneous assay reagents.

In each of the assays described above, the assay method involves reacting the serum from a test individual with the protein antigen and examining the antigen for the presence of bound antibody. The examination may involve attaching a labeled anti-human antibody to the antibody being examined, either IgM (acute phase) or IgG (convalescent or chronic phase), and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound recombinant HCV antigen (e.g., the 409-1-1 antigens, etc., as above), and a reporter-labeled anti-human antibody for detecting surface-bound anti-PT-NANBH-antigen antibody.

As discussed in Section III above, peptide antigens associated with several of the linking-fragment libraries are immunoreactive with acute NANBH sera from chimpanzees, indicating that the peptides would be useful for detecting acute NANBH infection in human serum. In particular, one or more peptide antigens produced by the linking fragment libraries, $F_8/R_9$ (reactive with chronic sera), $F_3R_4$, $F_6B_{12}$, $F_{12}R_7$, $F_7R_8$, or $F_7R_8$ (which are shown in Example 11 to produce one or more peptide antigens which are immunoreactive with acute chimpanzee sera) can be combined with the 409-1-1 antigens to provide a diagnostic composition capable of immunoreacting with a high percentage of both chronic and acute human NANBH serum samples. Further, as discussed in Section VII above inclusion of the HCV-capsid protein antigens of the present invention add an extra level of sensitivity.

A third diagnostic configuration involves use of the anti-HCV antibodies, described in Section VI above, capable of detecting HCV specific antigens. The HCV antigens may be detected, for example, using an antigen capture assay where HCV antigens present in candidate serum samples are reacted with an HCV specific monoclonal antibody. The monoclonal antibody is bound to a solid substrate and the antigen is then detected by a second, different labelled anti-HCV antibody: the monoclonal antibodies of the present invention which are directed against HCV specific antigens are particularly suited to this diagnostic method.

B. Peptide Vaccine

The HCV antigens identified by the methods of the present invention, e.g. 409-1-1(c-a) and HCV-core protein antigens, can be formulated for use in a HCV vaccine. The vaccine can be formulated by standard methods, for example, in a suitable diluent such as water, saline, buffered salines, complete or incomplete adjuvants, and the like. The immunogen is administered using standard techniques for antibody induction, such as by subcutaneous administration of physiologically compatible, sterile solutions containing inactivated or attenuated virus particles or antigens. An immune response producing amount of virus particles is typically administered per vaccinizing injection, typically in a volume of one milliliter or less.

A specific example of a vaccine composition includes, in a pharmacologically acceptable adjuvant, a recombinant 409-1-1(c-a) peptide. The vaccine is administered at periodic intervals until a significant titer of anti-HCV antibody is detected in the serum. Such vaccines can also comprise combinations of the HCV antigens of the present invention.

C. Passive Immunoprophylaxis

The anti-HCV antibodies of the invention can be used as a means of enhancing an anti-HCV immune response since antibody-virus complexes are recognized by macrophages and other effector cells. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with viral entry into cells. Thus, antibodies reactive with, for example, the 409-1-1(c-a) antigen can be passively administered alone in a "cocktail" with other anti-viral antibodies or in conjunction with another anti-viral agent to a host infected with a PT-NANBH virus to enhance the immune response and/or the effectiveness of an antiviral drug.

The following examples illustrate various aspects of the invention, but are in no way intended to limit the scope thereof.

Materials

*E. coli* DNA polymerase I (Klenow fragment) was obtained from Boehringer Mannheim Biochemicals (Indianapolis, Ind.). T4 DNA ligase and T4 DNA polymerase were obtained from New England Biolabs (Beverly, Mass.); Nitrocellulose filters were obtained from Schleicher and Schuell (Keene, N.H.).

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits were obtained from Boehringer-Mannheim Biochemical (BMB, Indianapolis, Ind.).

EXAMPLE 1

Construction of NANB-containing cDNA libraries

A. Infection of a Chimpanzee with HCV

A chimpanzee (#771) was inoculated with a Factor VIII preparation which was known to cause parenterally transmitted non-A non-B hepatitis (PT-NANBH) in human patients treated with the Factor VIII concentrate (Bradley). Post-infection ultrastructural changes in liver tissue were observed by electron microscopy and ALT (alanine amino transferase) elevation was observed in the infected chimpanzee. These observations are consistent with PT-NANBH infection.

B. Isolation of RNA from Sera

Serum was collected from the above described infected chimpanzee (#771) and four human PT-NANBH clinical sources (EGM, BV, CC and WEH). Ten milliliters of each undiluted serum was pelleted by centrifugation at 30K, for 3 hours in an SW40 rotor, at 4° C. RNA was extracted from each resulting serum pellet using the following modifications of the hot phenol method of Feramisco et al. Briefly, for each individual serum sample, the pellet was resuspended in 0.5 ml of 50 mM NaOAc, pH=4.8, containing 1% SDS. An equal volume of 60° C. phenol was added and incubated for 15 minutes at 60° C. with occasional vortexing. This mixture was transferred to a 1.5 ml microfuge tube and spun for two minutes at room temperature in a table top microfuge. The aqueous phase was transferred to a new microfuge tube. To the aqueous phase, 50 $\mu$l of 3M NaOAc, pH=5.2, and two volumes of 100% ethanol were added. This solution was held at −70° C. for approximately 10 minutes and then spun in a microfuge at 4° C. for 10 minutes. The resulting pellet was resuspended in 100 $\mu$l of sterile glass distilled water. To this solution 10 $\mu$l of NaOAc, pH=5.2, and two volumes of 100% ethanol were added. The solution was held at −70° C. for at least 10 minutes. The RNA pellet was recovered by centrifugation in a microfuge at 12,000×g for 15 minutes at 5° C. The pellet was washed in 70% ethanol and dried under vacuum.

C. Synthesis of cDNA (i) First Strand Synthesis

The synthesis of cDNA molecules was accomplished as follows. The above described RNA preparations were each resuspended in 26 $\mu$l of sterile glass distilled water (treated with diethyl pyrocarbonate, Maniatis et al.), 5 $\mu$l of 10×reaction buffer (0.5M Tris HCl, pH=8.5; 0.4M KCl; 0.1M $MgCl_2$; 4 mM DTT), 10 $\mu$l of a nucleotide solution (dGTP, dATP, dTTP, and dCTP, each at a concentration of 5 mM), 5 $\mu$l random primer, 0.25 $\mu$l of $^{32}$P-dCTP, 2 $\mu$l AMV reverse transcriptase, and 2 $\mu$l of RNASIN (Promega), in a total reaction volume of 50 $\mu$l. This mixture was incubated for one hour at 42° C.

(ii) Second Strand cDNA Synthesis

To the first strand synthesis reaction mixture the following components were added: 55 $\mu$l of 2×second strand synthesis buffer (50 mM Tris HCl, pH=7.0; 60 mM KCl); 2 $\mu$l RNase H; 5 $\mu$l DNA polymerase I, and 2 $\mu$l of the above described nucleotide solution. The reaction was incubated for one hour at 12° C., followed by a one hour incubation at room temperature. The reaction mixture was extracted with an equal volume of 1:1 phenol/chloroform, followed by an extraction using 24:1 chloroform/isoamyl alcohol. To each reaction mixture 1 $\mu$l of 10 mg/ml tRNA was added as carrier. The cDNA was precipitated by the addition of two volumes of 100% ethanol and chilling at −70° C. for 15 minutes. The cDNA was collected by centrifugation, the pellet washed with 70% ethanol and dried under vacuum.

(iii) Preparation of the Double Stranded cDNA for cloning

To provide vector compatible ends each of the double stranded cDNA preparations was tailed with EcoRI linkers in the following manner.

The cDNA was treated with EcoRI methylase under the following conditions: The cDNA pellet was resuspended in 20 $\mu$l 1×methylase buffer (50 mM Tris HCl, pH=7.5; 1 mM EDTA; 5 mM DTT), 2 $\mu$l 1 0.1 mM S-adenosyl-methionine (SAM) and 2 $\mu$l EcoRI methylase (New England Biolabs). The reaction was incubated for 30 minutes at 37° C. TE buffer (10 mM Tris-HCl, pH=7.5; 1 mM EDTA, pH=8.0) was added to achieve a final volume of 80 $\mu$l. The reaction mixture was extracted with an equal volume of phenol/chloroform (1:1) and then with an equal volume of chloroform/isoamyl alcohol (24:1). The cDNA was precipitated with two volumes of ethanol.

To maximize the number of blunt ends for the addition of linkers (Maniatis et al, 1982) the cDNA was then treated with the Klenow fragment of DNA polymerase I. The pelleted cDNA was resuspended in 11.5 $\mu$l of distilled water.

The following components were added to the resuspended cDNA: 4 µl of 5×NTB (10×NTB stock solution: 0.5M Tric.Cl pH=7.2; 0.1M MgSO$_4$; 1 mM dithiothreitol (DTT); 500 µg/ml bovine serum albumin (BSA)); 3 µl 0.1M MgCl$_2$, 1.5 µl 10GATC (a solution containing 10 mM of each nucleotide G, A, T, and C), and 1 µl Klenow (Boehringer Mannheim Biochemicals). The reaction mixture was incubated at room temperature for 30 minutes. The reaction mixture was extracted with phenol/chloroform and chloroform isoamyl alcohol as described above, and then precipitated with two volumes of ethanol.

The cDNA pellet was resuspended in 12 µl distilled water. To the resuspended linkers the following components were added: 5 µl EcoRI phosphorylated linkers (New England Biolabs), 2 µl 10×ligation buffer (0.66M Tris.Cl pH=7.6, 50 mM MgCl$_2$, 50 mM DTT, 10 mM ATP) and 1 µl T4 DNA ligase. The reaction was incubated at 14° C. overnight. The following morning the reaction was incubated at 67° C. for three minutes to inactivate the ligase, then momentarily chilled. To the ligation reaction mixture 2.5 µl of 10×high salt restriction digest buffer (Maniatis et al.) and 2.5 µl of EcoRI enzyme were added and the mixture incubated at 37° C. for at least 6 hours to overnight. To remove excess linkers the digestion mixture was loaded onto a 1.2% agarose gel and the reaction components size fractionated by electrophoresis. Size fractions of the 0.3–1.3 Kb and 1.3–7 Kb ranges were electroeluted onto NA45 paper (Schleicher and Schuell). The NA45 paper, with the eluted cDNA bound to it, was placed in a 1.5 ml microfuge tube containing 0.5 ml of elution solution (50 mM arginine, 1M NaCl, pH=9.0). The tube was then placed at 67° C. for approximately one hour to allow the cDNA to be eluted from the paper into the solution. The solution was then phenol/chloroform, chloroform/isoamyl alcohol extracted and precipitated with two volumes of ethanol. The resulting cDNA pellets were resuspended in 20 µl TE (pH=7.5).

(iv) Cloning of the cDNA into Lambda Vectors

The linkers used in the construction of the cDNAs contained an EcoRI site which allowed for direct insertion of the amplified cDNAs into lambda gt10 and gt11 vectors (Promega, Madison Wis.). Lambda vectors were purchased from the manufacturer (Promega) which were already digested with EcoRI and treated with bacterial alkaline phosphatase, to remove the 5' phosphate and prevent self-ligation of the vector.

The EcoRI-linkered cDNA preparations were ligated into both lambda gt10 and gt11 (Promega). The conditions of the ligation reactions were as follows: 1 µl vector DNA (Promega, 0.5 mg/ml); 0.5 or 3 µl of insert cDNA; 0.5 µl 10×ligation buffer (0.5M Tris-HCl, pH=7.8; 0.1M MgCl$_2$; 0.2M DTT; 10 mM ATP; 0.5 g/ml BSA), 0.5 µl T4 DNA ligase (New England Biolabs) and distilled Water to a final reaction volume of 5 µl.

The ligation reaction tubes were placed at 14° C. overnight (12–18 hours). The ligated cDNA was packaged the following morning by standard procedures using a lambda DNA packaging system (GIGAPAK, Stratagene, LaJolla, Calif.), and then plated at various dilutions to determine the titer and recombinant frequency of the libraries. A standard X-gal blue/white assay was used to screen the lambda gt11 libraries (Miller; Maniatis et al.). E. coli HG415 (from Howard Gersenfeld, Dept. of Pathology, Stanford School of Medicine) plating bacteria, which allows only plaque formation by recombinant clones, was used for plating the lambda gt10 libraries. The standard strain, E. coli C600 hF⁻, may be used as an alternative to E. coli HG415.

EXAMPLE 2

Screening the cDNA library for production of PT-NANBH antigens

The five lambda gt11 libraries generated in Example 1 were screened for specific HCV encoded viral antigens by immunoscreening. The phage were plated for plaque formation using the Escherichia coil bacterial plating strain E. coli KM392 (Kevin Moore, DNax, Palo Alto, Calif.). Alternatively, E. coli Y1088 may be used. The fusion proteins expressed by the lambda gt11 clones were screened with serum antibodies (Young et al.) from the following sources: chimpanzee #771 and various human PT-NANBH sera (including EGM, BV, WEH and AG).

From the lambda gt11 libraries (Example 1) approximately 111 independent clones gave a positive immunological reaction with at least one of the chimp or human PT-NANBH sera. These phage clones were plaque purified and the recombinant phage grown for DNA purification (Maniatis et al.).

EXAMPLE 3

Genomic Hybridization Screening of Immunopositive Clones

Out of the 111 plaque purified recombinant phage, obtained as in Example 2, 93 were isolated (Maniatis et al.) and digested with EcoRI as per the manufacturer's instructions (Bethesda Research Laboratories, Gaithersburg, Md.). Approximately 1.0 microgram of each digested phage DNA sample was loaded into sample wells of 1.0% agarose gels prepared using TAE (0.04 m Tris Acetate, 0.001M EDTA). The DNA samples were then electrophoretically separated. DNA bands were visualized by ethidium bromide staining (Maniatis et al.). Inserts were clearly identified for each of the 93 clones, purified by electroelution using NA45, and then radioactively labelled by nick translation (Maniatis et al.).

Human peripheral blood lymphocyte (PBL) DNA was restriction digested with HindlII and EcoRI, loaded on a 0.7% agarose gel (as above, except 10 µg of DNA was loaded per lane) and the fragments separated electrophoretically. The DNA fragments in the agarose gels were transferred to nitrocellulose filters (Southern) and the genomic DNA probed with the nick-translated lambda gt11 inserts which were prepared above.

The filters were washed (Southern; Maniatis et al.) and exposed to X-ray film. Forty-three of the 93 lambda clone inserts displayed a positive hybridization reaction with the human PBL DNA. Among the remaining inserts which clearly did not hybridize with the PBL DNA, were 11 inserts derived from chimp #771 clones which were also clearly immunopositive from Example 2. Of these 11 clones, two of the clones had the immunoreactive characteristics summarized in Table 1. Chimpanzee #771 and humans Ag, BV and WEH were chronimc PT-NANBH sera samples and SKF was a normal human serum sample.

TABLE 1

| | Clone Designation | |
|---|---|---|
| Sera | 36 | 40 |
| #771 | + | + |
| AG | + | − |
| BV | + | − |
| WEH | − | − |
| SKF | − | − |

Clone 40 (original clone screening designation 304-12-1) was clearly exogenous, i.e., not derived from normal human DNA, as evidenced by repeated hybridization tests against normal human PBL DNA, and a second clone, designated clone 36 (original clone screening designation 303-1-4), was not only exogenous but also reactive with multiple PT-NANBH antisera.

EXAMPLE 4

Sequencing of Clones

DNA sequencing was performed on clones 36 and 40 as described in Example 3. Commercially available sequencing primers (New England Biolabs) homologous to flanking lambda sequences at the 5' and 3' ends of the inserts were initially used for sequencing. As sequencing progressed primers were constructed to correspond to newly discovered sequences. Synthetic oligonucleotide primers were prepared using commercially available automated oligonucleotide synthesizers. Alternatively, custom designed synthetic oligonucleotides may be purchased, for example, from Synthetic Genetics (San Diego, Calif.).

DNA sequences were determined for the complete insert of clone 40 (presented as SEQ ID NO:1 and also shown in FIG. 3); this sequence corresponds to nucleotides 6516 to 7070 of the HCV genome (FIGS. 11A to 11H). Subsequently, the inserts present in clones 44 and 45 (2 other clones of the 11 clones identified in Example 3) were found to cross-hybridize to the clone 40 insert. Partial sequencing of clones 44 and 45 showed that the sequences obtained from these two clones matched the sequence of clone 40. A partial sequence of the clone 36 insert was determined and is presented as SEQ ID NO: 3; the complete sequence is presented as SEQ ID NO:5 and is also shown in FIG. 4. The sequence of clone 36 corresponds to nucleotides 5010 to 6515 given in the Appendix.

EXAMPLE 5

Screening of the cDNA library in lambda gt10

The cDNA libraries in lambda gt10, generated in Example 1, were screened for the presence of sequences homologous to the clone 40 insert.

The lambda gt10 libraries were plated at a density of approximately $10^4$ plaques/plate and plaques lifts were prepared according to Maniatis et al. Filters were indexed using india ink to allow alignment of the filters with the parent plate from which the plaque lift was performed. The bacteria and phage particles were lysed, and the nitrocellulose filters were processed and baked as previously described (Maniatis et al.). The prehybridization solution, per filter, consisted of the following: 5.4 ml prehybridization buffer (50 ml of 1M Tris HCl, pH=7.5; 2 ml of 0.5M EDTA, pH=8.0; 50 ml of 10% SDS; 150 ml of 20×SSC (Maniatis et al.); and, 238 ml of glass distilled water); 6.0 ml formamide; 0.4 ml 50×Denhardt solution (5 g FICOLL; 5 g polyvinylpyrrolidone; 5 g bovine serum albumin; brought to a total volume of 500 ml with glass distilled water); and 0.2 ml of single-stranded salmon sperm DNA (10 mg/ml). Each filter was placed in a plastic bag and the prehybridization solution was added. The bag was sealed and incubated at 37° C. overnight with intermittent mixing of contents.

The clone 40 lambda DNA was isolated (Maniatis et al.) and digested with EcoRI. The resulting fragments were fractionated on an agarose gel and visualized by ethidium bromide staining (Maniatis et al.). The DNA fragment corresponding to the clone 40 insert, approximately 500 base pairs, was isolated from the agarose by electroelution onto NA45. The aqueous suspension of the purified fragment was extracted once with a 1:1 phenol/chloroform solution, and once with a 24:1 chloroform/isoamylalcohol solution. The DNA was then precipitated with ethanol and resuspended in sterile water.

The clone 40 insert was radioactively labelled by nick translation and used to probe the lambda gt10 plaque lift filters. The prehybridization solution was removed from the filters. Each filter was hybridized with probe under the following conditions: 5.0 ml of hybridization buffer (5 ml of 1M Tris HCl, pH=7.5; 0.2 ml of 0.5M EDTA, pH=8.0; 5.0 ml of 10% SDS; 14.9 ml of 20×SSC (Maniatis et al.); 10 g of dextran sulfate; and, glass distilled water to a total volume of 50 ml); 5.0 ml formamide; 0.4 ml 50×Denhardt's solution (5 g FICOLL; 5 g polyvinylpyrrolidone; 5 g bovine serum albumin; brought to a total volume of 500 ml with glass distilled water); and 0.2 ml of single-stranded salmon sperm DNA (10 mg/ml). To this hybridization mix was added 50–250 $\mu$l of denatured probe (boiled 5–10 minutes and quick-chilled on ice), resulting in approximately $10^6$ cpm of labelled probe per filter. The hybridization mix containing the labelled probe was then added to the plastic bag containing the filters. The bag was resealed and placed under a glass plate in a 37° C. water bath overnight with intermittent mixing of contents.

The next day the hybridization solution was removed and the filters washed three times, for 5 minutes each, in 2×SSC (Maniatis et al.) containing 0.5% SDS, at room temperature. The filters were then washed for one hour in 2×SSC, containing 0.5% SDS, at 50° C. The filters were then washed for 15–60 minutes in 0.1×SSC, containing 0.1% SDS, at 50° C. and finally 2×SSC, 15 minutes, 2–3×at room temperature. The washed filters were dried and then exposed to X-ray film for detection of positive plaques.

Approximately 24 plaques from the lambda gt10 libraries were plaque purified from the approximately 200 plaques which tested positive by the hybridization screen (Table 2).

TABLE 2

| Library | cDNA Source | Positives/ Plate |
|---------|-------------|------------------|
| EGM     | Human       | ≅ 50             |
| BV      | Human       | ≅ 100            |
| WEH     | Human       | ≅ 25             |
| #771    | Chimp       | ≅ 10–15          |

EXAMPLE 6

Analysis of lambda gt10 cDNA Library Clones Homologous to the Clone 40 insert

The clones identified in Example 5 which have homology to the clone 40 insert were analyzed by standard restriction analysis and the insert sizes were determined. The original frequencies of positive hybridization signals per plate using the clone 40 insert as probe against the different cDNA sources are shown in the last column of Table 2. That these positive signals arose with different frequencies for the different cDNA sources in the lambda gt10 library suggests that the hybridization signals originated from the sera source rather than common contamination introduced during cDNA synthesis or cloning.

One of the clones (108-2-5) from the EGM-generated cDNA library identified by hybridization with the clone 40 insert, had an insert of approximately 3.7 kb and was chosen for further analysis. The insert was isolated by EcoRI digestion of the clone, electrophoretic fractionation, and electroelution (Example 5). The insert was treated with DNase I under conditions resulting in partial digestion (Maniatis et al.) to generate random fragments. The resulting fragments were inserted into lambda gt11 vectors for expression. The lambda gt11 clones were then immunoscreened (Example 2) using human (BV and normal) and chimpanzee #771 sera. Twelve positive clones were identified by first round immunoscreening with the human and chimp sera. Seven of the 12 clones were plaque purified and rescreened using chimp serum (#771). Partial DNA sequences of the insert DNA were determined for two of the resulting clones that had the largest sequences, designated 328-16-1 and 328-16-2. The 2 clones had sequences essentially identical to clone 40.

EXAMPLE 7

Preparing Amplified HCV cDNA Fragments

A. Preparing cDNA fragments

A plasma pool obtained from a chimpanzee with chronic PT-NANBH was obtained from the Centers for Disease Control (CDC) (Atlanta, Ga.). After direct pelleting or PEG precipitation, RNA was extracted from the virions by guanidinium thiocyanate-phenol-chloroform extraction, according to published methods (Chomczynski). The pelleted RNA was used for cDNA synthesis using oligo dT or random primers, or HCV sequence-specific primers and a commercial cDNA kit (Boehringer-Mannheim).

In one method, synthesis of first strand cDNA was achieved by addition of four primers, designated A, B, C, and D, having the sequences shown below. These sequences are complementary to the HCV genomic regions indicated:

A: 5'-GCGGAAGCAATCAGTGGGGC-3',
complementary to basepairs 394–413;
B: 5'-GCCGGTCATGAGGGCATCGG-3',
complementary to basepairs 2960–2980;
C: 5'-CGAGGAGCTGGCCACAGAGG-3',
complementary to basepairs 5239–5258; and
D: 5'-TGGTTCTATGGAGTAGCAGGCCCCG-3',
complementary to basepairs 7256–7280.

Second strand cDNA synthesis was performed by the method of Gubler and Hoffman. The reactions were carried out under standard cDNA synthesis methods given in the commercial kit.

B. Amplifying the cDNA Fragments

The cDNA from above was blunt ended and ligated to the linker/primer having the following sequence:

Linker/primer: 5'-GGA ATT CGC GGC CGC TCG-3' A-strand
3'-TT CCT TAA GCG CCG GCG AGC-5' B-strand The cDNA and linker were mixed at a 1:100 molar ratio in the presence of 0.3 to 0.6 Weiss units of T4 DNA ligase. To 100 µl of 10 mM Tris-Cl buffer, pH 8.3, containing 1.5 mM $MgCl_2$ and 50 mM KCl (Buffer A) was added about 1×10-3 µg of the linker-ended cDNA, 2 µM of linker/primer A (A-strand) having the sequence d(5'-GGAATTCGCGGCCGCTCG-3'), 200 µM each of dATP, dCTP, dGTP, and dTTP, and 2.5 units of *Thermus aquaticus* DNA polymerase (Taq polymerase). The reaction mixture was heated to 94° C. for 30 sec for denaturation, allowed to cool to 50° C. for 30 sec for primer annealing, and then heated to 72° C. for 0.5–3 minutes to allow for primer extension by Taq polymerase. The replication reaction, involved successive heating, cooling, and polymerase reaction, was repeated an additional 25 times with the aid of a Perkin-Elmer Cetus DNA thermal cycler. This results in a pool of SISPA (sequence-independent single primer amplification)-amplified DNA fragments.

EXAMPLE 8

Preparing Primer-Pair Fragments

Amplified cDNA fragments from Example 7 were mixed with 100 µl Buffer A, 1 µM of equal molar amounts of one of the primer pairs given below, 200 µM each of dATP, dCTP, dGTP, and dTTP, and 2.5 units of *Thermus aquaticus* DNA polymerase (Taq polymerase). Each primer pair includes a forward (upstream) primer $F_i$ which is identical to the coding strand at the upstream end of an overlap region $P_i$ of duplex genomic DNA and a reverse primer $R_i$ which is complementary to the coding at the downstream end of the region $P_i$. The sets of primers each define an overlap region of about 200 basepairs, and the spacing between adjacent overlapping primer regions (i.e., between adjacent pairs of $F_i/R_i$ pairs) is about 0.5–1 kilobase. The regions of HCV which are complementary to the primers are given below:

$F_1$, basepairs 183–201; $R_1$, basepairs 361–380

$F_{10}$, basepairs 576–595; $R_{10}$, basepairs 841–860

$F_2$, basepairs 1080–1100; $R_2$, basepairs 1254–1273

$F_3$, basepairs 1929–1948; $R_3$, basepairs 2067–2086

$F_4$, basepairs 2754–2733; $R_4$, basepairs 2920–2940

$F_5$, basepairs 3601–3620; $R_5$, basepairs 3745–3764

$F_6$, basepairs 4301–4320; $R_6$, basepairs 4423–4442

$F_{12}$, basepairs 4847–4865; $R_{12}$, basepairs 4715–4734

$F_7$, basepairs 5047–5066; $R_7$, basepairs 5200–5216

$F_8$, basepairs 5885–5904; $R_8$, basepairs 6028–6047

$F_9$, basepairs 6902–6921; $R_9$, basepairs 7051–7070

Polymerase Chain Reaction (PCR) amplification of the SISPA-amplified cDNA fragments with each $F_i/R_i$ primer pair was carried out under conditions similar to those used above, with about 25 cycles.

The amplified fragment mixtures from above were each fractionated by electrophoresis on 1.5% agarose and transferred to nitrocellulose filters (Southern). Hybridization of the nitrocellulose-bound fragments, each with an internal-sequence oligonucleotide probe confirmed that each fragment contained the expected sequences. Hybridization was carried out with an internal oligonucleotide radiolabeled by polynucleotide kinase, according to standard methods.

EXAMPLE 9

Preparing Linking Fragments

This example describes preparing large overlapping linking fragments of the HCV sequence. SISPA-amplified cDNA fragments from Example 7 were mixed with 100 µl Buffer A, 1 µM of equal molar amounts of forward and reverse primers in each of the primer pairs given below, 200 µM each of dATP, dCTP, dGTP, and dTTP, and 2.5 units of *Thermus aquaticus* DNA polymerase (Taq polymerase), as in Example 8. Each primer pair includes a forward primer Fi and a reverse primer$_j$, where $F_i$ is the forward primer for one overlap region $P_i$, and $R_j$ is the reverse primer of the adjacent overlap region. Thus each linking fragment spans two adjacent overlap regions. The sets of primers each define a linking fragment of about 0.5–1 kilobases. The sequences of the primer pairs are given in Example 8. The overlapping linking fragments of the HCV sequence (FIGS. 11A to 11H) spanned by each primer pair is given below:

$F_1/R_{10}$, basepairs 183–860

$F_{10}/R_2$, basepairs 576–1273

$F_2/R_3$, basepairs 1080–2086

$F_3/R_4$, basepairs 1929–2940

$F_4/R_5$, basepairs 2754–3762

$F_5/R_6$, basepairs 3601–4442

$F_6/R_{12}$, basepairs 4301–4865

$F_{12}/R_7$, basepairs 4715–5216

$F_7/R_8$, basepairs 5047–6047

$F_8/R_9$, basepairs 5885–7070

Two-primer amplification of the SISPA-amplified cDNA fragments with each $F_i/R_j$ primer pair was carried out under conditions similar to those described above, with about 25 cycles.

The amplified fragment mixtures from above were each fractionated by agarose electrophoresis on 1.2 % agarose, and transferred to nitrocellulose filters (Southern) for hybridization with radiolabeled internal oligonucleotide probes as above. The analysis confirmed that each linking fragment contained the two end-primer sequences from adjacent overlap regions. The sequences contained in each of the linking fragments are indicated in FIGS. 11A to 11H.

EXAMPLE 10

Preparing Cloned Peptide Fragments

A. DNA Fragment Digestion

Each of the ten linking fragments from Example 9 was suspended in a standard digest buffer (0.5M Tris HCl, pH 7.5; 1 mg/ml BSA; 10 mM MnC12) to a concentration of about 1 mg/ml and digested with DNAse I at room temperature for various times (1–5 minutes). These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers. The resultant fragments were analyzed by electrophoresis (5–1 OV/cm) on 1.2% agarose gels, using PhiX174/HaeIII and lambda/HindIII size markers. The 100–300 bp fraction was eluted onto NA45 strips (Schleicher and Schuell), which were then placed into 1.5 ml microtubes with eluting solution (1M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 µl TE buffer (0.01M Tris HCl, pH 7.5, 0.001M EDTA).

B. Cloning the Digest Fragments

Lambda gt11 phage vector (Young et al.) was obtained from Promega Biotec (Madison, Wis.). This cloning vector has a unique EcoRI cloning site 53 base pairs upstream from the beta-galactosidase translation termination codon. The partial digest fragments from each linking fragment in Part A were introduced into the EcoRI site by mixing 0.5–1.0 µg EcoRI-cleaved lambda gt11, 0.3–3 µl of the above sized fragments, 0.5 µl 10×ligation buffer (above), 0.5 µl DNA ligase (200 units), and distilled water to 5 µl. The mixture was incubated overnight at 14° C, followed by in vitro packaging, according to standard methods (Maniatis, pp. 256–268).

The packaged phage were used to infect E. coli strain KM392, obtained from Dr. Kevin Moore, DNAX (Palo Alto, Calif.). Alternatively, E. coli strain Y1090, available from the American Type Culture Collection (ATCC No. 37197), could be used. A lawn of KM392 cells infected with about $10^3$–$10^4$ pfu of the phage stock from above was prepared on a 150 mm plate and incubated, inverted, for 5–16 hours at 37° C. The infected bacteria were checked for loss of beta-galactosidase activity (clear plaques) in the presence of X-gal using a standard X-gal substrate plaque assay method (Maniatis).

Identification of single plaques containing a digest-fragment insert was confirmed as follows. Clear single plaques (containing the progeny of a single phage) were removed from the plate and suspended in extraction buffer (Maniatis) to release the phage DNA. The phage extract was added to the above DNA amplification mixture in the presence of primers which are about 70 basepairs away in either direction from the EcoRI site of lambda gt11. Thus phage containing a digest-fragment insert will yield an amplified digest fragment of about 140 basepairs plus insert. Phage DNA amplification was carried out as described above, with 25 cycles of amplification. The reaction material from each plaque tested was fractionated on 1.5% agarose, and examined for the size of amplified digest fragments. Non-recombinant phage gave a 140 basepair band, and recombinant phage, a band which is 140 basepair plus the insert sequence in size. The results are shown in column 2 (REC Freq) of Table 3 below, for the six linking-fragment libraries indicated in the first column in Table 3 below. The denominator in the column-2 entries is the total number of plaques assayed by primer amplification. The numerator is the number of clear plaques containing fragment inserts. Thus, 3/15 means that 3 plaques tested positive by PCR out of a total of 15 clear plaques assayed.

TABLE 3

| Library[1] | REC Freq[2] | 1° Screen[3] | PA/REC[4] |
|---|---|---|---|
| F2R3 #2 | 3/15 | 2 | 0.33 |
| F3R4 #1 | 7/12 | 0 | — |
| F4R5 #3 | 9/10 | 10 | 0.37 |
| F5R6 #5 | 11/12 | 37 | 1.35 |
| F7R8 #7 | 0/12 | 1 | — |
| F8R9 #10 | 3/12 | 58 | 7.73 |

[1]Libraries constructed by partial DNaseI Digestion of indicated linking clone
[2]Recombinant frequency determined by PCR with insert flanking lambda gt11 primers
[3]Primary screening with chronic human PT-NANBH serum (1:100) on 1.5 × 10 phage
[4]PA/REC indicates the number of positive areas detected per actual number of recombinant plated The library of digest fragments constructed for each linking fragment was screened for expression of peptides which are immunoreactive with a human PT-NANBH serum. The lawn of phage-infected bacteria was overlaid with a nitro- cellulose sheet, transferring PT-NANBH recombinant peptides from the plaques to filter paper. The plate and filter were indexed for matching corresponding plate and filter positions.

The filter was removed after 6–12 hours, washed three times in TBS buffer (10 mM Tris, pH 8.0, 150 mM NaCl), blocked with AIB (TBS buffer with 1% gelatin), washed again in TBS, and incubated overnight with of antiserum (diluted to 1:100 in AIB, 12–15 ml/plate). The sheet was washed twice in TBS and then incubated with alkaline-phosphatase-conjugated anti-human IgG to attach the labeled antibody at filter sites containing antigen recognized by the antiserum. After a final washing, the filter was developed in a substrate medium containing 33 µl NBT (50 mg/ml stock solution maintained at 4° C.) mixed with 16 µl BCIP (50 mg/ml stock solution maintained at 4° C.) in 5 ml of alkaline phosphatase buffer (100 mM Tris, 9.5, 100 mM NaCl, 5 mM MgC12). Reacted substrate precipitated at points of antigen production, as recognized by the antiserum.

The total number of plaques which showed antigen-positive reaction (positive areas PA) in the primary screen are given in the third column in Table 3. The fourth column in the table is the frequency of positive areas per total number of recombinant phage screened (×$10^3$). This last column is therefore a measure of the relative immunogenicity of antigen expressed from a particular linking fragment using this particular serum sample.

EXAMPLE 11

Screening Digest Fragments

The digest-fragment libraries of each of the ten linking fragments from Example 9 were screened with sera from a human patient with chronic PT-NANBH and with pooled sera from chimpanzees with acute PT-NANBH infection and chronic PT-NANBH infection. Individual chronic and acute chimpanzee sera from 5 chimpanzees were obtained from the Centers for Disease Control.

The digest-fragment libraries from the linking fragments indicated in Table 4 below were screened with each of the three sera, using the screening procedure described in Example 10. The total number of positive areas observed in each plate (making up one fragment library) is given in the table. The entries in the table which are not in parentheses represent the number of positive areas which were confirmed by plaque purification, i.e., by replating plaques from the positive areas at low dilution and confirming a positive area (secondary screen). Typically about 90–95 percent of the positive areas in the primary screen tested positive by secondary screening. The entries in parentheses indicate positive areas which have not been confirmed in a secondary screen.

As seen from Table 4, all but one of the linking fragment libraries contained sequences encoding peptide antigens which are immunoreactive with either chronic human or chimpanzee infected sera. Five of the libraries contain sequences encoding antigens which are immunoreactive with acute sera, indicating that one or more of the antigens in this group are effective to detect acute-infection serum. Three of these latter libraries—$F_3/R_4$, $F_{12}/R_7$, and $F_7/R_8$—gave over 10 positives in each library. These data are not corrected for the recombinant frequency in a particular library and therefore do not reflect the comparative immunogenicity of the various linking fragments.

TABLE 4

| Human P.P. Clones | Acute Pool P.P. Clones | Chronic Pool P.P. Clones |
|---|---|---|
| F1R10 | 0 | 0 | 0 |
| F10R2 | 4 | 2 | 4 |
| F2R3 | 4 | 0 | 1 |
| F3R4 | 0 | 10 | 10 |
| F4R5 | 5 | 0 | 7 |
| F5R6 | 34 | 0 | (42) |
| F6R12 | (400) | 5 | 10(200) |
| F12R7 | 2 | 17(200) | 9(200) |
| F7R8 | 0 | 20 | 10(130) |
| F8R9 | 60 | 0 | 1 |

( ) = not plaque purified
P.P. = Plaque Pure
Acute Pool = CDC Panel of Chimps
Chronic Pool = CDC Panel of Chimps

EXAMPLE 12

Immunoscreening for 409-1-1-Antigen

A. Plaque Immunoscreening

Several clear plaques identified in the primary screen of the $F_4/R_5$ linking fragment were replated and plaque purified. One of the purified plaques was designated gt11/409-1-1(c-a). The digest fragment contained in clone 409-1-1(c-a) corresponds to two sets of base pairs present in the HCV genome and present in clone 409-1-1(abc). For ease of reference three regions (a, b, and c,) have been designated in the 409-1-1(abc) clone (see below and FIG. 5). The longest homology of base pairs corresponds approximately to nucleotides 2754 to 3129 of FIGS. 11A to 11H (the "a" region, see FIG. 5, region delineated by boxes) and the shorter homology corresponds approximately to nucleotides 3242 to 3311 of FIGS. 11A to 11H (the "c" region, see FIG. 5): normally the "c" region is located approximately 112 nucleotides distal the 3' end of the "a" region (see FIG. 5). The complete sequence of the gt11/409-1-1(c-a) insert is given in FIG. 6 and presented as SEQ ID NO:7. This clone arose through a ligation event between two independent DNaseI fragments generated from the $F_4/R_5$ linking clone and has ATCC No. 40792. A related clone, designated 409-1-1(abc), has been described in co-owned patent application Ser. No. 505,611 and has ATCC No. 40876.

A lambda gt11 clone corresponding to the immunoreactive sequence reported in the EPO application 88310922.5, and designated 5-1-1, was prepared by primer-specific amplification of the amplified cDNA fragments generated in Example 7. The 5-1-1 sequence corresponds to basepairs 3730-3858 of the HCV sequence (FIGS. 11A to 11H), in the linking fragment $F_5/R_6$. The primers used for fragment amplification are 20 basepair oligomers complementary to the forward and reverse sequences of the 3732-3857 basepair 5-1-1 sequence. Both oligomers have EcoRI sites incorporated into their ends and the forward oligomer is designed to ensure a contiguous open reading frame with the beta-galactosidase gene. The amplified 5-1-1 sequence was purified by agarose gel electrophoresis, and cloned into lambda gt11 phage. Amplification and cloning methods were as described above. Phage containing the 5-1-1 sequence were identified and purified by primary and secondary screening, respectively, with human PT-NANBH serum, also as described above.

The purified gt11/409-1-1(c-a) and gt11/5-1-1 clones were each mixed with negative lambda gt11 phage, plated and immunoscreened with a number of different donor sera from normal and NANBH-infected humans and chimpanzees, as indicated in Table 5 below. Each plate was divided into several equal-area sections, and the corresponding sections on the nitrocellulose transfer filter were separately screened with the donor sera indicated, using the immunoscreening method described in Example 11. The number of positives detected for each group of sera by the 5-1-1 and 409-1-1 (c-a) peptides are shown, as well as a comparison with the C-100 test in the ELISA format, in Table 5.

TABLE 5

| | | | # Positive | | |
|---|---|---|---|---|---|
| Source | Diagnosis | # Donors | 5-1-1 | 409-1-1 (c-a) | C-100 |
| Human | Normal | 2 | 0 | 0 | NT |
| Human | ANAB | 6 | 4 | 5 | 0/1* |
| Chimp | Normal | 7 | 0 | 0 | 0/5 |
| Chimp | Acute | 5 | 1 | 3 | 0/5 |
| Chimp | Chronic | 8 | 7 | 7 | 5/5 |

NT, not tested; * only BV serum was tested; N/5 means N positives out of five sera tested.

B. Western Blot Screening

For Western blot screening, gt11/409-1-1(c-a) phage from Example 11 was used to infect E. coli BNN103 temperature-sensitive bacteria. These bacteria were obtained from the American Type Culture Collection. The bacterial host allows expression of a beta-galactosidase/peptide antigen fused protein encoded by the vector under temperature induction conditions (Hunyh).

Infected bacteria were streaked, grown at 32° C. overnight or until colonies were apparent, and individual colonies were replica plated and examined for growth at 32° C. and 42° C. Bacterial colonies which grew at 32° C., but not 42° C., indicating integration of the phage genome, were used to inoculate 1 ml of NZYDT (Maniatis) broth A saturated overnight bacterial culture was used to inoculate a 10 ml culture, which was incubated with aeration to an O.D. of about 0.2 to 0.4, typically requiring 1 hour incubation. The culture was then brought to 43° C. quickly in a 43° C. water bath and shaken for 15 minutes to induce lambda gt11 peptide synthesis, and incubated further at 37° C. for 1 hour.

The cells were pelleted by centrifugation, and 1 ml of the pelleted material was resuspended in 100 μl of lysis buffer (62 mM Tris, pH 7.5 containing 5% mercaptoethanol, 2.4% SDS and 10% glycerol). Aliquots (about 15 μl) were loaded directly onto gels and fractionated by SDS-PAGE. After electrophoresis, the fractionated bands were transferred by electroelution to nitrocellulose filters, according to known methods (Ausubel et al.).

The lysate was treated with DNaseI to digest bacterial DNA, as evidenced by a gradual loss of viscosity in the lysate. An aliquot of the material was diluted with Triton X-100™ and sodium dodecyl sulfate (SDS) to a final concentration of 2% Triton X-100™ and 0.5% SDS. Non-solubilized material was removed by centrifugation and the supernatant was fractionated by SDS polyacrylamide electrophoresis (SDS-PAGE).PAGE, A portion of the gel was stained, to identify the peptide antigen of interest, and the corresponding unstained band was transferred onto a nitrocellulose filter.

The 5-1-1 antigen coding sequence (Example 11) was also expressed as a glutathione-S-transferase fusion protein using the pGEX vector system, according to published methods (Smith). The fusion protein obtained from bacterial lysate and fractionated by SDS-PAGE were transferred to a nitrocellulose filter for Western blotting, as above.

Western blotting was carried out substantially as described in Example 10. Briefly, the filters were blocked with AIB, then reacted with the serum samples identified in Table 5, including human and chimpanzee normal, chronic NANBH, and hepatitis B (HBV) sera sample. The presence of specific antibody binding to the nitrocellulose filters was assayed by further immunobinding of alkaline-phosphatase labelled anti-human IgG. The results of the Western blot analysis with the Sj26/5-1-1 fusion protein and /409-1-1(c-a) fusion proteins are shown in Table 6. The data confirm that 409-1-1(c-a) and 5-1-1 peptide antigens are specifically immunoreactive with human and chimpanzee NANBH antisera.

TABLE 6

| | | | # Positive | |
|---|---|---|---|---|
| Source | Diagnosis | # Donors | Sj26 5-1-1 | β-gal 409-1-1 (c-a) |
| Human | Normal | 2 | 0 | 0 |
| Human | NANB | 7 | 5 | 5 |
| Human | HBV | 1 | 0 | 0 |
| Chimp | Normal | 5 | 0 | 0 |
| Chimp | NANB | 6 | 5 | 5 |
| Chimp | HBV | 1 | 0 | 0 |

EXAMPLE 13

Generation of Alternative Clones

Alternative clones were generated from the region identified in Example 12 as encoding antigen specifically immunoreactive with human and chimpanzee NANBH antisera. The primers shown in Table 7 were selected from the HCV or 409-1-1(abc) coding sequences to generate a variety of overlapping clones.

TABLE 7

| Primer | Sequence |
|---|---|
| 33C-F1 | CCGAATTCGCGGTGGACTTTATCCCTGT |
| 33C-R1 | CCGAATTCCAGAGCAACCTCCTCGATG |
| 409-1-1(c-a)F | CCGAATTCCGCACGCCCGCCGAGACTAC |
| 409-1-1-F1 | CCGAATTCTCCACCACCGGAGAGATCCC |
| 409-1-1-R2 | CCGAATTCCACACGTATTGCAGTCTATC |
| 409-1-1-F3 | CCGAATTCGTCACCCAGACAGTCGAT |
| 409-1-1-R5 | CCGAATTCCCCTCCCAAAATTCAAGATGG |
| 409-1-1(c-a)R | CCGAATTCGCCAGTCCTGCCCCGACGTT |
| 409-1-1CR | CCGAATTCGTCCTGGCACACGGGAAG |

The primers shown in Table 7 were used in DNA amplification reactions as described in Examples 7B and 8: the primers and templates used in each reaction are shown in Table 8. The amplified fragments were then treated with the Klenow fragment of DNA polymerase I, under standard conditions (Maniatis et al.), to fill in the ends of the molecules. The blunt-end amplified fragments were digested with EcoRI under standard conditions and cloned into lambda gt11 expression vectors essentially as described in Example 10B. The resulting inserts are aligned for comparison in FIG. 7.

TABLE 8

| Generated Fragment | Template | Primers |
|---|---|---|
| 33C | cDNA* | 33-C-F1 and 409-1-1-R2 |
| 33CU | cDNA* | 33-C-F1 and 33-C-R1 |
| 4O9-1-1(F1R2) | gt11 409-1-1(c-a) | 409-1-1-F1 and 409-1-1-R2 |
| 4O9-1-1(a) | gt11 409-1-1(c-a) | 409-1-1-F1 and 409-1-1caR |
| 4O9-1-1(c) | gt11 409-1-1(c-a) | 409-1-1caF and 409-1-1CR |
| 4O9-1-1(c + 270) | gt11 409-1-1(c-a) | 409-1-1caF and 409-1-1-R2 |
| 409-1-1u | gt11 409-1-1(c-a) | 409-1-1-F3 and 409-1-1caR |

*Amplified cDNA fragments from Example 7

EXAMPLE 13

Immunoscreening of the Alternative Clones

The alternative clones generated in Example 12 were immunoscreened essentially as described in Example 10B. Clones 409-1-1(abc) and 409-1-1(c-a), generated in Example 12, were also included in the following immunoscreenings. The results of the preliminary immunoscreening are shown in Table 9.

TABLE 9

| | GLI-1 | FEC |
|---|---|---|
| 33C | + | ND* |
| 33cu | + | ND |
| 409-1-1 (abc) | + | ND |
| 409-1-1 (F1R2) | + | ND |
| 409-1-1 (a) | + | ND |
| 409-1-1 (ca) | + | ND |
| 409-1-1 (C) | − | — |
| 409-1-1 (c + 270) | + | ND |
| 409-1-1 u | − | — |

*Not Done

The GLI-1 sera was a human chronic PT-NANBH sera. If a clone tested negative with GLI-1 it was further examined by screening with FEC, a human chronic PT-NANBH sera.

The seven of the 9 alternative clones which tested positive by the above preliminary immunoscreening were more extensively screened against a battery of sera. In addition, clone C100 (see Background) was included in the screening. The results of this more exhaustive screening are presented in Table 10.

tic antigens since they are more specific to HCV induced antibodies.

The immunoscreening was further extended to include the clone 36 and 45 (corresponds to clone 40) encoded epitopes which were identified above. Table 11 shows the results of the immunoscreening.

TABLE 10

| Serum | C100 | 33C | 33Cu | ANTIGEN 409-1-1 abc | 409-1-1 F1R2 | 409-1-1 a | 409-1-1 c + 270 | 409-1-1 ca | 5-1-1 |
|---|---|---|---|---|---|---|---|---|---|
| SKF(−) | − | − | − | − | − | − | − | − | − |
| FEC(+) | + | +3 | +3 | | +1 | +2 | +2 | − | +2+2 |
| BV | − | +2 | +3 | I | +1 | +1 | − | +1 | − |
| Bar | − | +2 | +2 | I | − | − | − | − | − |
| PP(−) | − | − | − | − | − | − | − | − | − |
| AP | − | +1 | +2 | − | I | − | − | I | − |
| CP | + | +2 | +3 | +2 | +3 | +3 | I | +3 | +2 |
| 1 | − | − | − | − | − | − | − | − | − |
| 2 | − | − | − | − | − | − | − | − | − |
| 3 | − | − | − | − | − | − | − | − | I |
| 4 | − | − | − | I | I | − | − | − | I |
| 5 | − | − | +1 | − | − | − | − | − | − |
| 6 | − | +1 | +3 | +1 | +1 | +1 | − | +1 | +1 |
| 7 | − | +2 | +3 | +1 | +2 | +2 | − | +2 | +1 |
| 38 | − | − | I | +1 | I | I | − | − | I |
| 39 | − | − | +1 | I | +1 | − | − | I | I |
| 40 | + | +1 | +2 | +1 | +1 | − | I | +1 | +1 |
| 41 | + | +2 | +3 | +1 | +1 | +1 | − | +2 | +1 |
| 42 | + | +2 | +3 | +1 | +1 | +1 | − | +2 | +1 |
| 43 | − | − | − | − | − | − | − | − | − |
| 44 | − | I | I | − | − | − | − | − | − |
| 45 | − | I | +1 | I | I | − | − | I | I |
| 46 | + | +1 | +2 | +1 | +2 | +1 | − | +1 | I |
| 47 | + | +1 | +2 | +2 | +2 | +3 | ≈ | +3 | +1 |
| B18 | − | +3 | +3 | +1 | +3 | +3 | − | +3 | − |
| A7 | − | +3 | +3 | +1 | +1 | +3 | − | +3 | +3 |
| C7 | − | +2 | +3 | − | − | − | − | − | − |
| A3 | − | +3 | +3 | +1 | +2 | +1 | − | +2 | − |
| B7 | − | +2 | +3 | I | +3 | +3 | − | +3 | I |
| C12 | + | +2 | +3 | − | − | − | − | − | − |

The serum samples used for screening were identified as follows: SKF, PT-NANBH negative; FEC, PT-NANBH positive; BV, community acquired NANBH; Bar, PT-NANBH positive; PP (pre-inoculation pooled chimpanzee serum), PT-NANBH negative; AP (acute HCV pooled chimpanzee serum), PT-NANBH positive; and, CP (chronic HCV pooled chimpanzee serum) PT-NANBH positive. The numbered serum samples correspond to human clinical serum samples which were PT-NANBH positive. The PP, CP, and AP sera were pooled sera samples from 5 different chimpanzees: the chimpanzee serum samples were obtained from the Centers for Disease Control. The scoring system presented in Table 10 is a qualitative scoring system defined as follows: (−), a clear negative; (+), (1+), (2+), (3+), increasing strength of positive signal, with (3+) being the strongest signal; and (I) stands for Indeterminate, where two readings were different and not repeated.

In view of the data presented in Table 10 the sensitivity of the antigens in terms of immunoscreening is 33cu>33c>409-1-1(c-a)>409-1-1-F1R2>409-1-1(abc)≧409-1-1a>5-1-1>409-1-1-(c+270). Although 33cu and 33c were sensitive antigens, they reacted with high background against all sera. Accordingly, the 409-1-1 series are more useful as diagnos-

TABLE 11

PANEL I: SEROCONVERSION SPECIMENS

| SERUM | C-100 | 33C | 5.1.1 | ANTIGEN 409-1-1 (c-a) | 36 | 45 | gt11 |
|---|---|---|---|---|---|---|---|
| GLI-1 | + | 4+ | 2+ | 4+ | − | 3+ | − |
| FEC | + | 4+ | 3+ | 4+ | 3+ | − | − |
| BV | − | 3+ | − | 3+ | − | − | − |
| SKF(norm) | − | − | − | − | − | − | − |
| 1-NO1/D69 | − | I | − | − | − | − | − |
| 2-NO1/D124 | − | + | − | − | − | − | − |
| 3-NO1/D146 | − | I | − | − | − | − | − |
| 4-NO1/D211 | − | + | − | − | − | − | − |
| 5-N00/D22 | − | + | I | I | − | − | − |
| 6-N00/D29 | − | 2+ | + | 2+ | − | − | − |
| 7-N00/D41 | − | 3+ | 2+ | 3+ | − | − | − |
| 8-N00/D60 | − | 4+ | 3+ | 4+ | − | − | − |
| 9-N00/D137 | + | 4+ | 4+ | 4+ | 2+ | − | − |
| 10-N240/D0 | − | I | − | I | − | − | − |
| 11-N240/D45 | − | − | − | − | − | − | − |
| 12-N240/D71 | − | I | − | I | − | − | − |
| 13-N240/D89 | − | I | − | − | − | − | − |
| 14-N240/D106 | − | I | − | − | − | − | − |
| 15-N240/D155 | − | I | − | − | − | − | − |
| 16-N228/D0 | − | I | − | − | − | − | − |
| 17-N228/D31 | − | I | − | − | − | − | − |
| 18-N228/D41 | − | I | − | − | − | − | − |
| 19-N228/D51 | − | I | − | − | − | − | − |

TABLE 11-continued

PANEL I: SEROCONVERSION SPECIMENS

| SERUM | C-100 | 33C | 5.1.1 | ANTIGEN 409-1-1 (c-a) | 36 | 45 | gt11 |
|---|---|---|---|---|---|---|---|
| 20-N228/D73 | – | I | – | – | – | – | – |
| 21-N228/D93 | – | – | – | – | – | – | – |
| 22-N228/D127 | – | – | – | – | – | – | – |
| 23-N192/D114 | – | – | I | – | – | – | – |
| 24-N192/D184 | – | – | – | – | – | – | – |
| 25-N192/D224 | – | – | – | – | – | – | – |
| 26-N192/D280 | – | I | – | – | – | – | – |
| 27-N176/D0 | – | I | – | – | – | – | – |
| 28-N176/D66 | – | – | – | – | – | – | – |
| 29-N176/D77 | – | – | – | – | – | – | – |
| 30-N176/D94 | – | – | – | – | – | – | – |
| 31-N176/D200 | – | – | – | – | – | – | – |
| 32-N170/D0 | – | – | – | – | – | – | – |
| 33-N170/D27 | – | I | – | – | – | – | – |
| 34-N170/D49 | – | – | – | – | – | – | – |
| 35-N170/D64 | – | – | – | – | – | – | – |
| 36-N170/D183 | – | – | – | – | – | – | – |
| 37-N170/D278 | – | – | – | – | – | – | – |
| 38-N144/D63 | – | I | – | – | – | – | – |
| 39-N144/D72 | – | I | – | – | – | – | – |
| 40-N144/D91 | + | 2+ | + | 2+ | – | – | – |
| 41-N144/D289 | + | 4+ | + | 3+ | 2+ | – | – |
| 42-N144/D233 | + | 4+ | 3+ | 4+ | 2+ | – | – |
| 43-N122/D0 | – | I | – | – | – | – | – |
| 44-N122/D51 | – | I | I | I | – | – | – |
| 45-N122/D57 | – | 2+ | I | + | – | – | – |
| 46-N122/D72 | + | 2+ | – | 3+ | I | – | – |
| 47-N122/D94 | + | 3+ | + | 4+ | + | – | – |
| 48-N122/D199 | + | 4+ | 2+ | 4+ | + | – | – |
| 49-N31/D0 | – | I | – | – | – | – | – |
| 50-N31/D140 | – | – | – | – | – | – | – |
| 51-N31/D154 | – | – | – | – | – | – | – |
| 52-N31/D170 | – | – | – | – | – | – | – |
| 53-N31/D210 | – | – | – | – | – | – | – |
| 54-N31/D266 | – | – | – | – | – | – | – |
| 55-N31/D336 | – | – | – | – | – | – | – |
| 56-N31/D394 | – | – | – | – | – | – | – |
| 57-N16/D0 | – | – | – | – | – | – | – |
| 58-N16/D47 | – | – | – | – | – | – | – |
| 59-N16/D62 | – | – | – | – | – | – | – |
| 60-N16/D83 | – | – | – | – | – | – | – |
| 61-N16/D137 | – | – | – | – | – | – | – |
| 61-N16/D167 | – | – | – | – | – | – | – |
| 63-N16/D197 | – | – | – | – | – | – | – |
| 64-N16/D370 | – | – | – | – | – | – | – |

The screening sera GLI-1, FEC, BV, and SKF have been defined above. The numbered sera samples correspond to human clinical serum samples which were PT-NANBH positive: these samples were obtained from Dr. Francoise Fabiani-Lunel, Hospital La Pitie Salpetriere, Paris, France. As can be seen from the results presented in Table 11, the antigens produced by clones 36 and 40, while not as sensitive as 409-1-1(c-a), do yield HCV-specific immunopositive signals.

EXAMPLE 14

Isolation of 409-1-1 Fusion Protein

Sepharose 4B beads conjugated with anti-beta galactosidase were purchased from Promega. The beads were packed in 2 ml column and washed successively with phosphate-buffered saline with 0.02% sodium azide and 10 ml TX buffer (10 mM Tris buffer, pH 7.4, 1% aprotinin).

BNN103 lysogens infected with gt11/409-1-1(c-a) from Example 12 were used to inoculate 500 ml of NZYDT broth. The culture was incubated at 32° C. with aeration to an O.D. of about 0.2 to 0.4, then brought to 43° C. quickly in a 43° C. water bath for 15 minutes to induce gt11 peptide synthesis, and incubated further at 37° C. for 1 hour. The cells were pelleted by centrifugation, suspended in 10 ml of lysis buffer (10 mM Tris, pH 7.4 containing 2% Triton X-100™ and 1% aprotinin added just before use. The resuspended cells were frozen in liquid nitrogen, then thawed, resulting in substantially complete cell lysis. The lysate was treated with DNaseI to digest bacterial and phage DNA, as evidenced by a gradual loss of viscosity in the lysate. Non-solubilized material was removed by centrifugation.

The clarified lysate material was loaded on the Sepharose column, the ends of the column were closed, and the column was placed on a rotary shaker for 2 hrs. at room temperature and 16 hours at 4° C. After the column settled, it was washed with 10 ml of TX buffer. The fused protein was eluted with 0.1M carbonate/bicarbonate buffer, pH10. A total of 14 ml of the elution buffer was passed through the column, and the fusion protein eluted in the first 4–6 ml of eluate.

The first 6 ml of eluate from the affinity column were concentrated in Centricon™-30 cartridges (Amicon, Danvers, Mass.). The final protein concentrate was resuspended in 400 µl PBS buffer. Protein purity was analyzed by SDS-PAGE. A single prominent band was observed.

EXAMPLE 15

Preparation of Anti-409-1-1(c-a) Antibody

The 409-1-1(c-a) digest fragments from lambda gt11 were released by EcoRI digestion of the phage, and the "A" region purified by gel electrophoresis. The purified fragment was introduced into the pGEX expression vector (Smith). Expression of glutathione S-transferase fused protein (Sj26 fused protein) containing the 409-1-1(a) peptide antigen was achieved in E. coli strain KM392 (above). The fusion protein was isolated from lysed bacteria, and isolated by affinity chromatography on a column packed with glutathione-conjugated beads, according to published methods (Smith).

The purified Sj26/409-1-1(a) fused protein was injected subcutaneously in Freund's adjuvant in a rabbit. Approximately 1 mg of fused protein was injected at days 0 and 21, and rabbit serum was collected on days 42 and 56.

A purified Sj26/5-1-1 fused protein was similarly prepared using the an amplified HCV fragment encoding the 5-1-1 fragment. The fused Sj26/5-1-1 protein was used to immunize a second rabbit, following the same immunization schedule. A third rabbit was similarly immunized with purified Sj26 protein obtained from control bacterial lysate.

Minilysates from the following bacterial cultures were prepared as described in Example 12: (1) KM392 cells infected with pGEX, pGEX containing the 5-1-1 insert, and pGEX containing the 409-1-1(a) insert; and (2) BNN103 infected with lambda gt11 containing the 5-1-1 insert and gt11 containing the 409-1-1(c-a) insert. The minilysates were fractionated by SDS-PAGE, and the bands transferred to nitrocellulose filters for Western blotting as described in Example 12. Table 12 shows the pattern of immunoreaction which was observed when the five lysate preparations (containing the antigens shown at the left in the table) were screened with each of the three rabbit immune sera. Summarizing the results, serum from control (Sj26) rabbits was immunoreactive with each of the Sj26 and Sj26 fused protein antigens. Serum from the animal immunized with Sj26/5-1-1 fused protein was reactive with all three Sj-26 antigens and with the beta-gal/5-1-1 fusion protein, indicating the presence of specific immunoreaction with the 5-1-1 antigen. Serum from the animal immunized with Sj26/409-1-1(a) fused protein was reactive with all three Sj-26 antigens and with the beta-gal/409-1-1(c-a) fusion protein, indicating the presence of specific immunoreaction with the 409-1-1(a) antigen. None of the sera were immunoreactive with beta-galactosidase (obtained from a commercial source).

TABLE 12

| Antigens | | Antibody | |
|---|---|---|---|
| Sj26 | Sj26 | 5-1-1/Sj26 | 409-1-1(a)/- |
| Sj26 | + | + | + |
| 5-1-1/ (Sj26) | + | + | + |
| 5-1-1/ (β-bal) | − | + | − |
| 409-1-1(a) (Sj26) | + | + | + |
| 409-1-1(c-a) (β-gal) | − | − | + |

Anti-409-1-1(a) antibody present in the sera from the animal immunized with the Sj26/409-1-1(a) is purified by affinity chromatography, following the general procedures described in Example 12, but where the ligand derivatized to the Sepharose beads is the purified beta-gal/409-1-1(c-a) fusion protein, rather than the anti-beta-galactosidase antibody.

EXAMPLE 16

Cloning the HCV Capsid Protein Coding Sequences

The example describes the cloning of HCV coding sequences which encodes the N-terminal region of the HCV capsid protein.

The protein sequence of the HCV-capsid associated antigen corresponds to the nucleotide residues 325-970 of the full length HCV sequence (see FIGS. 11A to 11H). The following sequences were used as PCR primers to clone this region: SF2(C), 5' end starting at nucleotide 325 of the full length HCV sequence (Appendix), 5'-GCGCCCATGGGCACGATTCCCAAACCTCA; and SR1(C), 3' end starting at nucleotide 969 of the full length HCV sequence (Appendix), 5'-GCCGGATCCCTATTACTC(G/A)TACACAAT(A/G)CT(C/T)GAGTT(A/G)G. The anticipated size of the fragment generated using the SF2(C)/SR1(C) primer pair was 644 base pairs.

SISPA-amplified cDNA fragments from Example 7 were mixed with 100 μl Buffer A, 1 μM of equal molar amounts of each SR2 and SF1 primer given above, 200 μM each of dATP, dCTP, dGTP, and dTTP, and 2.5 units of *Thermus aquaticus* DNA polymerase (Taq polymerase), as in Example 8.

Specific amplification of the SISPA-amplified cDNA fragments with the capsid primer pair given above was carried out under conditions similar to those described in Example 7, with 1 minute at 72° C. and about 30 cycles.

The amplified fragment mixtures from above were each fractionated by agarose gel electrophoresis on duplicate 1.2% agarose gels, and one of the gels transferred to nitrocellulose filters (Southern) for hybridization with with a radioactively labelled oligonucleotide (Southern) having the following sequence: SF3(M/E), 5' end starting at nucleotide 792 of the full length HCV sequence (Appendix), 5'-GCGCCCATGGTTCTGGAAGACGGCGTG. This oligonucleotide corresponds to a sequence internal to the amplification product generated by using the SF2(C) and SR1(C) primers. Eight out of 15 PCR products were identified which gave a positive hybridization signal with the internal probe.

The vectors pGEX (Example 15) and pET (NOVAGEN, 565 Science Drive, Madison, Wis. 53711) were chosen for bacterial expression of protein sequences encoded by the inserts. The pGEX vector provided expression of the inserted coding sequences as fusion proteins to Sj26 (see Examples 12 and 15) and the pET vector provided expression of the cloned sequences alone. To clone the capsid sequences, the amplification product bands were excised from the duplicate gel. The DNA was extracted from the agarose and doubly-digested with NcoI and BamHI. A pGEX vector containing the BamHI/NcoI cloning sites was also doubly digested with BamHI and NcoI. The vector and extracted DNA were then ligated under standard conditions and the ligation mixture transformed into bacterial cells.

The bacterial transformants were cultured under ampicillin selection, and the plasmid DNA isolated by alkaline lysis (Maniatis et al.). The isolated plasmid DNA was digested with NcoI and BamHI. The digestion products were then electrophoretically separated on an agarose gel. The gel was transferred to nitrocellulose and probed with radioactively labelled SF3 as above. Twelve clones were confirmed to have the insert of interest by the Southern blot analysis.

Clones were generated in the pET vector in essentially the same manner.

EXAMPLE 17

Immunological Screening of the Putative HCV Capsid Protein Clones

This example describes the immunological screening of the putative HCV capsid protein clones which were obtained in Example 18.

Of the twelve clones obtained in Example 16, protein mini-lysates of 7 clones (clones # 8, 14, 15, 56, 60, 65, and 66) were prepared as described in Example 12. These mini-lysates were fractionated as described and transferred to nitrocellulose for Western Blot analysis. Table 13 shows the pattern of immunoreaction which was observed when the 7 lysate preparations were screened with the indicated sera.

TABLE 13

| | Sera | | | | |
|---|---|---|---|---|---|
| Clone | SKF | FEL | A6 | B9 | BV |
| 8 | − | − | − | − | − |
| 14 | − | + | + | + | + |
| 15 | − | + | + | + | + |
| 56 | − | + | + | + | + |
| 60 | − | + | + | + | + |
| 65 | − | + | + | + | + |
| SJ26 | − | − | − | − | − |
| 5-1-1 | − | + | + | + | − |
| 409-1-1 | − | − | + | + | − |

The serum samples used for screening were identified as follows: SKF, HCV negative; FEC, HCV positive; BV, community acquired HCV; A6 and B9 correspond to human clinical serum samples which were HCV positive.

Immunoreactive bands identified on the Western blot were all smaller than the expected size of 50 kd (based on the predicted coding sequence of the cloned inserts, see below).

Clone 15 was chosen for scale-up production of the Sj26 fusion protein (Smith et al.). A one liter preparation of clone 15 yielded about 200 μg of purified immunoreactive material. The bulk of the immunoreactive material appeared in a major doublet band which ran at approximately 29 kd. The yield from this preparation was unexpectedly low: typically with the pGEX system a one liter protein preparation yields in the range of 50–100 mg fusion protein.

EXAMPLE 18

Nucleic Acid Sequences of Clones 15 and 56

The inserts of clones 15 and 56 (discussed in Example 17) were sequenced as per the manufacturer's instructions (US Biochemical Corporation, Cleveland Ohio) using the dideoxy chain termination technique (Sanger, 1979). Each of the clones had an open reading frame contiguous with the Sj26 reading frame of the pGEX vector. The sequences of the clone inserts were near identical with only a few minor sequence variations: the sequence of clone 15 had a termination codon starting at nucleotide position 126. The sequence data for clone 56 is presented as SEQ ID NO:11 and in FIG. 8A.

The sequencing of the inserts revealed the unusual feature of a run of adenine residues from nucleotide position 25 to position 34 (FIG. 8A): such sequences are similar to sequences known to promote translation frame-shifting (Wilson et al., Atkins et al.). The open reading frame contiguous with the Sj26 coding sequence predicts a protein of approximately 23.5 kd. Accordingly, given the approximately 26 kd size of the Sj26 protein fragment in this construct (Smith et al.), the complete fusion protein would be predicted to be approximately 50 kd.

EXAMPLE 19

Hydropathicity Plot of the Protein Encoded by Clone 56

The SOAP program from IntelliGenetics PC/GENE™ software package was used to generate the hydropathicity plot of FIG. 9. The SOAP program uses the method of Kyte et al. to plot the hydropathicity of the protein along its sequence. The interval used for the computation was 11 amino acids. In FIG. 9, the hydrophobic side of the plot corresponds to the positive values range and the hydrophilic side to the negative values range.

The hydropathicity plot indicates (i) the hydrophilic nature of the amino terminus of the capsid protein, (ii) the relatively hydrophobic nature of the region of amino acid residues approximately 122 to 162, and (iii) the hydrophobic nature of amino acid residues approximately 168–182.

Further, the region of amino acid residues 168–182 demonstrates potential for being a membrane spanning segment (Klein et al.).

EXAMPLE 20

Deletion Analysis of the Clone 56 Protein Coding Region

This example describes the generation of a series of carboxy and amino terminal deletions of the HCV capsid protein and the effect of these deletions on the immunoreactivity of the resulting proteins.

A. Carboxy Terminal Deletions of Clone 56.

As one step to improve the expression of the HCV capsid protein, the putative region of translational frameshifting was modified to reduce the probability of a frameshift occurring in this region. In each AAA codon, encoding lysine, (nucleotide positions 25 to 33, FIG. 8A) the third nucleotide in each codon (positions 27, 30 and 33, FIG. 8A) was changed from A to G using standard PCR mismatch techniques (Ausubel et al., Mullis, Mullis et al.). The sites of these substitutions are indicated in FIG. 8A by the three G's placed over the corresponding A's. The sequence of the modified pGEX clone was confirmed as in Example 19 and the clone was named pGEX-CapA. The insert sequence of clone pGEX-CapA is shown in FIG. 8B and presented as SEQ ID NO: 13.

The deletion clones were generated using the PCR primers given in Table 14. In Table 14 the BamHI site is italicized and the termination codon is underlined.

TABLE 14

CARBOXY TERMINAL DELETION PRIMERS

| | | | | | | | | | | | |
|---|---|---|---|---|---|---|---|---|---|---|---|
| 1. C1 | 5'-CGA TCC ATG GGC ACG AAT CCT AAA CC | | | | | | | | | | |
| 2. NC580 | 5'-G | GCC | GGA | TCC | TTA | GGC | CGA | AGC | GGG | CAC | AG |
| 3. NC520 | 5'-G | GCC | GGA | TCC | TTA | ACC | AGG | AAG | GTT | CCC | TGT | TGC |
| 4. NC450 | 5'-G | GCC | GGA | TCC | TTA | GGC | CCT | GGC | ACG | GCC | TCC |
| 5. NC360 | 5'-G | GCC | GGA | TCC | TTA | CAA | ATT | GCG | CGA | CCT | ACG | CC |
| 6. NC270 | 5'-G | GCC | GGA | TCC | TTA | GCC | CTC | ATT | GCC | ATA | GAG |

Amplification reactions were carried out essentially as described in Example 16 using primer C1 paired with each of the NC primers and purified plasmid pGEX-CapA as template: the amplification reaction was 1 minute at 95°, annealed 2 minutes at 50° and 3 minutes at 72° for 20 cycles.

The following sequence comparisons are given relative to the nucleic acid sequence presented in FIG. 8B. The C1 primer corresponds to the common 5' end of the pGEX-CapA insert which contains an NcoI site near the initiating methionine. The sequence of the NC primers each start at the nucleotide position indicated, for example, the homologous sequence of the NC580 primer ends at nucleotide position 580. A termination codon is inserted at that position, following a BamHI site. The positions of the primers given in Table 14 are indicated in FIG. 8B. The approximate locations of the primers relative to the protein sequence are indicated in FIG. 9.

The resulting amplification products were electrophoretically size fractionated on a polyacrylamide gel and the DNA products of the appropriate sizes electroeluted from the gel. The amplification products were cloned into both the pGEX and the pET vectors for expression. The sequences of the inserts were confirmed as described in Example 18.

The pGEX vectors containing the carboxy-terminal deletions were transformed into *E. coli* and the fusion proteins purified essentially as follows. Expression of the fusion protein was induced with IPTG for 3–4 hours. The cells were then harvested at 6,000 rpm for 10 minutes. The *E. coli* were then lysed in MTPBS buffer (150 mM NaCl; 16 mM $Na_2HPO_4$; 4 mM $NaH_2PO_4$, pH=8.0 ) after which 1% "TRITON X-100," 3 μg/ml DNase I, and 1 mM PMSF were added. The lysates were centrifuged at 15,000 rpm for 20 minutes. The supernatants were discarded and the pellets resuspended in 8M urea. The components of the resuspenion were separated by HPLC using a "BIO-GEL SP-5-PW" column. Typically, the fusion protein was the predominant peak: the location of the fusion protein was confirmed by Western Blot analysis. Clones C1NC270, C1NC360, and C1NC450 all expressed Sj26 fusion proteins at high levels: the fusion proteins all corresponded to the size predicted from the insert coding sequence fused to the Sj26 protein and were immunoreactive with HCV-positive sera (Western Blots were performed as described in Example 17). Although the supernatants were discarded substantial amounts of the fusion proteins were also present in the supernatants. Clones C1NC520 and C1NC 580 gave poor yields of fusion proteins.

An epitope map of the HCV capsid region is presented in FIG. 10: the location of the immunoreactive protein coding sequences corresponding to inserts C1NC 450, C1NC 360, and C1NC 270 are indicated. The sequences of C1NC 450, C1NC 360, and C1NC 270 are presented in the Sequence Listing as SEQ ID NO:15, SEQ ID NO:17, and SEQ ID NO:19, respectively.

B. Amino Terminal Deletions of Clone 56

Amino terminal deletion clones were generated using the PCR primers given in Table 15.

TABLE 15

AMINO TERMINAL DELETION PRIMERS

1. C100 GAG CCC ATG GGT GGA GTT TAC TTG TTG CC
2. C270 GAG CCC ATG GGC TGC GGG TGG GCG GG
3. C360 GAG CCC ATG GGT AAG GTC ATC GAT ACC

Amplification reactions were carried out essentially as described above using the primer pairs presented in Table 16 and purified plasmid pGEX-CapA as template: the amplification reaction included was 1 minute at 95°, annealed 2 minutes at 50°, and 3 minutes at 72° for 20 cycles.

TABLE 16

| NH₂ Primer | COOH Primer | Protein Produced? | Immunoreactive? |
|---|---|---|---|
| C100 | NC450 | LOW | YES |
|  | NC360 | YES | YES |
|  | NC270 | YES | YES |
| C270 | NC450 | YES | NO |
|  | NC360 | YES | NO |
| C360 | NC450 | YES | NO |

The following sequence comparison are given relative to the nucleic acid sequence presented in FIG. 8B where the above described A to G substitutions have been made for the sequence of pGEX-CapA. The NC660 primer corresponds to the common 3' end of the pGEX-CapA insert which contains a BamHI site near the end of the insert. The sequence of the C primers each start at the nucleotide position indicated, for example, the sequence of the NC100 primer begins at nucleotide position 100. Each of the C primers introduces an in-frame initiation codon in the resulting amplification product. The positions of the primers given in Table 15 are indicated in FIG. 8C.

The resulting amplification products were cloned into the pGEX and pET vector for expression as described above. The sequences of the inserts were confirmed.

The pGEX vectors containing the carboxy-terminal deletions were transformed into *E. coli*, protein minilysates prepared, and the immunoreactivity of the proteins analyzed by Western Blots as described above. The results of the analysis are presented in Table 16. Clones C100NC270 and C100NC360 expressed Sj26 fusion proteins at high levels: the fusion proteins corresponded to the size predicted from the insert coding sequence fused to the Sj26 protein.

An epitope map of the HCV capsid region is presented in FIG. 10: the location of the protein coding sequences corresponding to inserts C100NC 270, C100NC 360, C270NC360, and C270NC450 are indicated. The sequences for C100NC 270 and C100NC 360 are presented in the Sequence Listing as SEQ ID NO:21 and SEQ ID NO:23, respectively.

EXAMPLE 21

Expanded Immunoscreening Using the Capsid Antigen

This example describes three different comparisons of the immunoreactivity of the various HCV antigens of the present invention to several battery of sera.

A. Effectiveness of Cap450 Antigen

Table 17 shows the results of 50 human sera samples from patients suspected of NANB hepatitis infection. The ELISA assays were performed essentially as described by Tijssen using the following 3 antigens: C100, 409-1-1(c-a), C33u, Cap450 (the protein product of the pGEX-C1NC 450 clone), and with 409-1-1(c-a) and cap4150 in one well which was optimized to give the most sensitive results. These ELISA data were compared with the Abbott C100 test.

Patient serum was scored positive for Sj26 fusion proteins (409-1-1 ca, 33u, 5-1-1, and Cap450) if the absorbance was three times the absorbance of that serum on Sj26 native protein. A sample was scored positive on pET antigens (cap360) if the absorbance was three times the mean of the absorbance of negative control sera. A patient serum was scored positive on the combined 409-1-1 ca/cap450 assay if the absorbance was equivalent or greater than that of control positive sera. Samples within 10% of the control positive sera were scored weak positives.

[Samples 1–19: Chronic active hepatitis proven by biopsy. HBS Ag(–).

Samples 20–44: Acute viral hepititis HBsAg(1), ISM Anti-HBC(–), IgM anti-HAV(–).

Samples 45–50: Chronic active hepatitis proven by biopsy. HBsAg(–).

TABLE 17

Korean Panel II

| Sample # | C100 | 409-1-1 (c-a) | C33u | Cap 450 | Combined 409-1-1 (c-a) + CAP450 |
|---|---|---|---|---|---|
| 1 |  | + | + | + | + | + |
| 2 |  | + | + | + | + | + |
| 3 |  | + | + | + | + | + |
| 4 |  | + | + | + | + | + |
| 5 |  | + | + | + | + | + |
| 6 |  | + | + | + | + | + |
| 7 |  | + | + | + | + | + |
| 8 |  | + | + | + | + | + |
| 9 |  | + | – | + | + | + |
| 10 |  | + | – | + | * | + |
| 11 |  | + | + | + | * | + |
| 12 |  | + | + | + | + | + |
| 13 |  | + | + | + | + | + |
| 14 |  | + | + | + | + | + |
| 15 |  | + | + | + | + | + |
| 16 |  | + | + | + | * | + |
| 17 |  | + | + | + | + | + |
| 18 |  | + | + | + | + | + |
| 19 |  | + | – | – | – | – |
| 20 | 945 | – | – | – | – | – |
| 21 | 988 | + | + | + | * | + |

TABLE 17-continued

Korean Panel II

| Sample # | | C100 | 409-1-1 (c-a) | C33u | Cap 450 | Combined 409-1-1 (c-a) + CAP450 |
|---|---|---|---|---|---|---|
| 22 | 3383 | + | – | – | – | – |
| 23 | 4072 | – | – | – | – | – |
| 24 | 4242 | – | – | – | – | – |
| 25 | 4490 | – | – | – | – | – |
| 26 | 4816 | – | – | – | – | – |
| 27 | 5322 | – | – | – | – | – |
| 28 | 6603 | – | – | – | – | – |
| 29 | 7923 | – | – | – | – | – |
| 30 | 9033 | – | – | – | – | – |
| 31 | 9768 | – | – | – | – | – |
| 32 | 9775 | – | – | – | – | – |
| 33 | 10197 | + | – | – | + | w+* |
| 34 | 10200 | – | – | – | – | – |
| 35 | 10409 | – | – | – | – | – |
| 36 | 10811 | – | – | – | – | – |
| 37 | 11209 | – | + | + | + | ND |
| 38 | 12245 | – | – | – | – | – |
| 39 | 12143 | – | – | – | – | – |
| 40 | 12519 | – | – | – | – | – |
| 41 | 13510 | – | – | – | – | – |
| 42 | 14018 | – | – | – | – | – |
| 43 | 14188 | – | – | – | – | – |
| 44 | 13437 | – | – | – | – | – |
| 45 | 863 | – | – | – | – | – |
| 46 | 3354 | – | – | – | – | – |
| 47 | 12640 | – | + | + | + | + |
| 48 | 13095 | – | * | + | – | w+ |
| 49 | 14501 | – | – | – | – | – |
| 50 | 14345 | + | + | + | + | + |

* = positive (low)

The results demonstrate that the Cap450 protein has good sensitivity for detecting the presence of anti-HCV antibodies in sera samples. Three additional samples (6, 37, and 47) were detected. Further, these results indicate that the combination of Cap450 and 409-1-1(c-a) can be used to produce a kit which is very effective for detection of anti-HCV antibodies in human sera samples.

B. Cap450 and Cap360

The results in Table 18 demonstrate the effectiveness of the Cap450 and Cap360 antigen (the protein product encoded by of pET-C1NC 360) to detect HCV antibodies present in human sera. The samples were tested for the presence of HCV by ELISA using each individual antigen shown, or with 409-1-1 (c-a) and Cap450 antigens combined in one well.

TABLE 18

| SERUM | PATIENT DIAGNOSIS | C100 | ELISA 5-1-1 | 409-1-1 (c-a) | C33u | Cap 360 | Combined (409-1-1) + Cap450 |
|---|---|---|---|---|---|---|---|
| G-131 | Acute Hepatitis; Pt "C.O." | – | – | – | – | – | – |
| G-132 | Acute Hepatitis; Pt "C.O." | – | – | – | – | – | – |
| G-143 | Acute Hepatitis; Pt "C.O." | – | – | – | – | – | – |
| G-285 | Acute Hepatitis; Pt "C.O." | ND | ND | ND | ND | ND | – |
| G-150 | Acute P.T. Hepatitis; Pt "G.L." | – | – | I | I | + | + |
| G-151 | Acute P.T. Hepatitis; Pt "G.L." | – | – | I | – | + | + |
| G-152 | Acute P.T. Hepatitis; Pt "G.L." | – | – | – | – | + | + |
| G-153 | Acute P.T. Hepatitis; Pt "G.L." | – | – | I | – | + | + |
| G-286 | Acute P.T. Hepatitis; Pt "G.L." | ND | ND | ND | ND | ND | + |
| G-43 | Fulminant Liver Disease | – | – | – | – | – | – |
| G-1 | Community Acquired Hepatitis | ND | I | + | + | + | + |
| G-109 | Community Acquired Hepatitis | + | – | + | + | + | + |
| G-114 | Community Acquired Hepatitis | ND | – | – | – | – | – |
| G-128 | Community Acquired Hepatitis | + | – | I | + | + | + |
| G-3 | Community Acquired Hepatitis | – | – | – | – | – | – |
| G-126 | Community Acquired Hepatitis | – | – | – | – | – | + |
| G-127 | Community Acquired Hepatitis | + | I | + | + | – | + |
| G-42 | Idiopath. Comm. Ac. Hepatitis | – | – | – | – | – | – |
| G-51 | Community Acquired Hepatitis B | – | – | + | + | + | + |
| G-27 | Community Acquired Hepatitis B | – | – | – | – | – | – |

TABLE 18-continued

| SERUM | PATIENT DIAGNOSIS | C100 | ELISA 5-1-1 | 409-1-1 (c-a) | C33u | Cap 360 | Combined (409-1-1) + Cap450 |
|---|---|---|---|---|---|---|---|
| G-22 | Community Acquired Hepatitis B | − | − | − | − | − | − |
| G-40 | Community Acquired Hepatitis B | − | − | − | − | − | − |
| G-31 | Community Acquired Hepatitis B | + | − | + | + | + | + |
| G-45 | Community Acquired Hepatitis B | − | − | − | − | − | − |
| G-38 | Fulminant Hepatitis B | − | − | − | − | − | − |
| G-41 | Community Acquired Hepatitis C | − | − | I | + | I | + |
| G-13 | Hepatitis C | + | I | + | + | + | + |
| G-12 | Hepatitis C | + | − | + | + | + | + |
| G-6 | Hepatitis C | − | − | − | − | − | − |
| G-49 | EtOH Cirrhosis | − | − | − | − | − | − |
| G-25 | EtOH Cirrhosis | − | − | − | − | − | − |
| G-110 | EtOH Cirrhosis | − | − | + | + | I | + |
| G-46 | EtOH Cirrhosis | − | − | − | − | − | − |
| G-272 | Infant Liver Transplant | ND | − | − | − | − | − |
| G-274 | Infant Liver Transplant | ND | − | + | + | − | − |
| G-16 | PBC | − | − | + | + | − | − |
| G-123 | INC LT | − | − | − | − | − | − |
| G-122 | INC LT | − | + | − | − | − | − |
| G-125 | No Diagnosis | − | I | + | + | I | + |
| G-124 | No Diagnosis | − | − | − | + | + | + |

These results indicate that the combination of antigen 409-1-1(c-a) and Cap360 or Cap450 result in a effective diagnostic tool for detection of HCV infection. Five additional samples (G150, G151, G110, G125, and G124) were detected with these ELISA's compared with C100 test alone.

C. pET360

The results in Table 19 demonstrate the effectiveness of the pET360 to detect HCV antibodies present in human sera. The samples were tested for the presence of HCV by ELISA using each individual antigen shown, or with 409-1-1 (c-a) and pET360 antigens combined in one well.

TABLE 19

|   | C100 | 5-1-1 | 409-1-1 (c-a) | C33u | pET360 | Combined 409-1-1 (c-a) + pET360 |
|---|---|---|---|---|---|---|
| A | + | − | + | + | − | + |
| B | + | + | + | + | − | + |
| C | + | − | − | + | − | + |
| D | + | + | + | − | + | + |
| E | + | − | w+ | + | + | + |
| F | − | − | − | − | − | − |
| G | + | − | w+ | + | + | + |
| H | − | − | + | + | + | + |
| I | − | − | − | − | − | − |

TABLE 19-continued

|   | C100 | 5-1-1 | 409-1-1 (c-a) | C33u | pET360 | Combined 409-1-1 (c-a) + pET360 |
|---|---|---|---|---|---|---|
| J | − | − | − | − | − | − |
| K | − | − | − | + | + | + |
| L | − | − | − | − | − | − |
| M | − | − | − | − | − | − |
| N | − | w+ | − | + | + | + |
| O | + | w+ | + | + | + | + |
| P | + | w+ | + | + | + | + |
| Q | − | − | − | − | − | − |
| R | − | − | − | − | − | − |
| S | − | − | − | − | − | − |

These results indicate that the combination of antigen 409-1-1 (c-a) and pET360 result in a effective diagnostic tool for detection of HCV infection. Three additional samples were detected with these ELISA's compared with C100 test alone.

Although the invention has been described with reference to particular embodiments, methods, construction and use, it will be apparent to those skilled in the art that various changes and modifications can be made without departing from the invention.

It is claimed:

1. A recombinant polypeptide which is specifically immunoreactive with sera from humans infected with hepatitis C virus (HCV), where said polypeptide includes the peptide sequence presented as SEQ ID NO:8.

2. The polypeptide of claim 1 that is encoded by the polynucleotide sequence presented as SEQ ID NO:7.

3. A method of detecting hepatitis C virus (HCV) infection in an individual comprising reacting serum from an HCV-infected test individual with a peptide antigen which is specifically immunoreactive with sera from humans infected with hepatitis C virus (HCV), where said peptide antigen includes the peptide sequence presented as SEQ ID NO:8, and examining the antigen for the presence of bound antibody.

4. The method of claim 3, wherein the peptide antigen is attached to a solid support, said reacting includes reacting the peptide antigen with the support, and subsequently reacting the support with a reporter-labeled anti-human antibody, and said examining includes detecting the presence of reporter-labeled antibody on the solid support.

5. A method of producing a polypeptide which is specifically immunoreactive with sera from humans infected with hepatitis C virus (HCV), comprising introducing into a suitable host, a recombinant expression vector containing an open reading frame (ORF) having a polynucleotide sequence which encodes a polypeptide which is specifically immunoreactive with sera from humans infected with hepatitis C virus (HCV), where said polypeptide includes the peptide sequence presented as SEQ ID NO:8 and where the vector is designed to express the ORF in said host, and culturing said host under conditions resulting in the expression of the ORF sequence.

6. The method of claim 5, wherein the polynucleotide has the sequence presented as SEQ ID NO:7.

7. The method of claim 6, wherein the expression vector is a lambda gt11 phage vector, the host is *E. coli*, and the host containing the introduced vector is identified by ATCC No. 40792.

8. An expression system for expressing a recombinant peptide antigen which is specifically immunoreactive with sera from humans infected with hepatitis C virus (HCV), comprising a host capable of supporting expression of an open reading frame in a selected expression vector, and the selected expression vector containing an open reading frame (ORF) having a polynucleotide sequence which encodes said peptide antigen, where said peptide antigen includes the peptide sequence presented as SEQ ID NO:8.

9. The expression system of claim 8, wherein the polynucleotide has the sequence presented as SEQ ID NO:7.

10. The expression system of claim 9, wherein the expression vector is a lambda gt11 phage vector, the host is *E. coli*, and the host containing the introduced vector is identified by ATCC No. 40792.

11. A polynucleotide which encodes a polypeptide which is specifically immunoreactive with sera from humans infected with hepatitis C virus (HCV), where said polypeptide includes the peptide sequence presented as SEQ ID NO:8.

12. The polynucleotide of claim 11, which includes the polynucleotide sequence presented as SEQ ID NO:7.

\* \* \* \* \*

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:

(A) LENGTH: 561 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Hepatitis C Virus
(B) STRAIN: CDC (vii) IMMEDIATE SOURCE:
(B) CLONE: 304-12-1

(ix) FEATURE:
(A) NAME/KEY: CDS
(B) LOCATION: 1..561

(xi) SEQUENCE DESCRIPTION: SEQ ID NO:1:

```
GAA TTC CTC GTG CAA GCG TGG AAG TCC AAG AAA ACC CCA ATG GGG TTC      48
Glu Phe Leu Val Gln Ala Trp Lys Ser Lys Lys Thr Pro Met Gly Phe
 1               5                  10                  15

TCG TAT GAT ACC CGC TGC TTT GAC TCC ACA GTC ACT GAG AGC GAC ATC      96
Ser Tyr Asp Thr Arg Cys Phe Asp Ser Thr Val Thr Glu Ser Asp Ile
             20                  25                  30

CGT ACG GAG GAG GCA ATC TAC CAA TGT TGT GAC CTC GAC CCC CAA GCC     144
Arg Thr Glu Glu Ala Ile Tyr Gln Cys Cys Asp Leu Asp Pro Gln Ala
         35                  40                  45

CGC GTG GCC ATC AAG TCC CTC ACC GAG AGG CTT TAT GTT GGG GGC CCT     192
Arg Val Ala Ile Lys Ser Leu Thr Glu Arg Leu Tyr Val Gly Gly Pro
     50                  55                  60

CTT ACC AAT TCA AGG GGG GAG AAC TGC GGC TAT CGC AGG TGC CGC GCG     240
Leu Thr Asn Ser Arg Gly Glu Asn Cys Gly Tyr Arg Arg Cys Arg Ala
 65                  70                  75                  80

AGC GGC GTA CTG ACA ACT AGC TGT GGT AAC ACC CTC ACT TGC TAC ATC     288
Ser Gly Val Leu Thr Thr Ser Cys Gly Asn Thr Leu Thr Cys Tyr Ile
             85                  90                  95

AAG GCC CGG GCA GCC TGT CGA GCC GCA GGG CTC CAG GAC TGC ACC ATG     336
Lys Ala Arg Ala Ala Cys Arg Ala Ala Gly Leu Gln Asp Cys Thr Met
         100                 105                 110

CTC GTG TGT GGC GAC GAC TTA GTC GTT ATC TGT GAA AGC GCG GGG GTC     384
Leu Val Cys Gly Asp Asp Leu Val Val Ile Cys Glu Ser Ala Gly Val
     115                 120                 125

CAG GAG GAC GCG GCG AGC CTG AGA GCC TTC ACG GAG GCT ATG ACC AGG     432
Gln Glu Asp Ala Ala Ser Leu Arg Ala Phe Thr Glu Ala Met Thr Arg
 130                 135                 140

TAC TCC GCC CCC CCC GGG GAC CCC CCA CAA CCA GAA TAC GAC TTG GAG     480
Tyr Ser Ala Pro Pro Gly Asp Pro Pro Gln Pro Glu Tyr Asp Leu Glu
145                 150                 155                 160

CTC ATA ACA TCA TGC TCC TCC AAC GTG TCA GTC GCC CAC GAC GGC GCT     528
Leu Ile Thr Ser Cys Ser Ser Asn Val Ser Val Ala His Asp Gly Ala
             165                 170                 175

GGA AAG AGG GTC TAC TAC CTC ACC CGG GAA TTC                         561
Gly Lys Arg Val Tyr Tyr Leu Thr Arg Glu Phe
         180                 185
```

(2) INFORMATION FOR SEQ ID NO:2:

(i) SEQUENCE CHARACTERISTICS:
(A) LENGTH: 187 amino acids
(B) TYPE: amino acid
(D) TOPOLOGY: linear ( i i ) MOLECULE TYPE: protein ( x i ) SEQUENCE DESCRIPTION: SEQ ID NO:2:

| Glu | Phe | Leu | Val | Gln | Ala | Trp | Lys | Ser | Lys | Thr | Pro | Met | Gly | Phe |
|---|---|---|---|---|---|---|---|---|---|---|---|---|---|---|
| 1 | | | | 5 | | | | | 10 | | | | | 15 |

| Ser | Tyr | Asp | Thr | Arg | Cys | Phe | Asp | Ser | Thr | Val | Thr | Glu | Ser | Asp | Ile |
|---|---|---|---|---|---|---|---|---|---|---|---|---|---|---|---|
| | | | 20 | | | | | 25 | | | | | 30 | | |

| Arg | Thr | Glu | Glu | Ala | Ile | Tyr | Gln | Cys | Cys | Asp | Leu | Asp | Pro | Gln | Ala |
|---|---|---|---|---|---|---|---|---|---|---|---|---|---|---|---|
| | | 35 | | | | | 40 | | | | | 45 | | | |

| Arg | Val | Ala | Ile | Lys | Ser | Leu | Thr | Glu | Arg | Leu | Tyr | Val | Gly | Gly | Pro |
|---|---|---|---|---|---|---|---|---|---|---|---|---|---|---|---|
| | 50 | | | | | 55 | | | | | 60 | | | | |

| Leu | Thr | Asn | Ser | Arg | Gly | Glu | Asn | Cys | Gly | Tyr | Arg | Arg | Cys | Arg | Ala |
|---|---|---|---|---|---|---|---|---|---|---|---|---|---|---|---|
| 65 | | | | | 70 | | | | | 75 | | | | | 80 |

| Ser | Gly | Val | Leu | Thr | Thr | Ser | Cys | Gly | Asn | Thr | Leu | Thr | Cys | Tyr | Ile |
|---|---|---|---|---|---|---|---|---|---|---|---|---|---|---|---|
| | | | | 85 | | | | | 90 | | | | | 95 | |

| Lys | Ala | Arg | Ala | Ala | Cys | Arg | Ala | Ala | Gly | Leu | Gln | Asp | Cys | Thr | Met |
|---|---|---|---|---|---|---|---|---|---|---|---|---|---|---|---|
| | | | 100 | | | | | 105 | | | | | 110 | | |

| Leu | Val | Cys | Gly | Asp | Asp | Leu | Val | Val | Ile | Cys | Glu | Ser | Ala | Gly | Val |
|---|---|---|---|---|---|---|---|---|---|---|---|---|---|---|---|
| | | 115 | | | | | 120 | | | | | 125 | | | |

| Gln | Glu | Asp | Ala | Ala | Ser | Leu | Arg | Ala | Phe | Thr | Glu | Ala | Met | Thr | Arg |
|---|---|---|---|---|---|---|---|---|---|---|---|---|---|---|---|
| | 130 | | | | | 135 | | | | | 140 | | | | |

| Tyr | Ser | Ala | Pro | Pro | Gly | Asp | Pro | Pro | Gln | Pro | Glu | Tyr | Asp | Leu | Glu |
|---|---|---|---|---|---|---|---|---|---|---|---|---|---|---|---|
| 145 | | | | | 150 | | | | | 155 | | | | | 160 |

| Leu | Ile | Thr | Ser | Cys | Ser | Ser | Asn | Val | Ser | Val | Ala | His | Asp | Gly | Ala |
|---|---|---|---|---|---|---|---|---|---|---|---|---|---|---|---|
| | | | | 165 | | | | | 170 | | | | | 175 | |

| Gly | Lys | Arg | Val | Tyr | Tyr | Leu | Thr | Arg | Glu | Phe |
|---|---|---|---|---|---|---|---|---|---|---|
| | | | 180 | | | | | 185 | | |

( 2 ) INFORMATION FOR SEQ ID NO:3:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis HCV Virus
        ( B ) STRAIN: CDC &nbs

```
CGC  GTG  TGC  GAA  AAG  ATG  GCT  TTG  TAC  GAC  GTG  GTT  ACC  AAG  CTC  CCC        192
Arg  Val  Cys  Glu  Lys  Met  Ala  Leu  Tyr  Asp  Val  Val  Thr  Lys  Leu  Pro
          50                  55                           60

TTG  GCC  GTG  ATG  GGA  AGC  TCC  TAC  GGA  TTC  CAA  TAC  TCA  CCA  GGA  CAG        240
Leu  Ala  Val  Met  Gly  Ser  Ser  Tyr  Gly  Phe  Gln  Tyr  Ser  Pro  Gly  Gln
65                       70                      75                          80

CGG  GTT  GAA  TTC                                                                    252
Arg  Val  Glu  Phe
```

( 2 ) INFORMATION FOR SEQ ID NO:4:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asn  Ser  Val  Trp  Lys  Asp  Leu  Leu  Glu  Asp  Asn  Val  Thr  Pro  Ile  Asp
 1                    5                      10                          15

Thr  Thr  Ile  Met  Ala  Lys  Asn  Glu  Val  Phe  Cys  Val  Gln  Pro  Glu  Lys
               20                      25                          30

Gly  Gly  Arg  Lys  Pro  Ala  Arg  Leu  Ile  Val  Phe  Pro  Asp  Leu  Gly  Val
          35                       40                      45

Arg  Val  Cys  Glu  Lys  Met  Ala  Leu  Tyr  Asp  Val  Val  Thr  Lys  Leu  Pro
          50                  55                           60

Leu  Ala  Val  Met  Gly  Ser  Ser  Tyr  Gly  Phe  Gln  Tyr  Ser  Pro  Gly  Gln
65                       70                      75                          80

Arg  Val  Glu  Phe
```

( 2 ) INFORMATION FOR SEQ ID NO:5:

( i ) SEQUENCE CHARACTERISTICS:
        ( A ) LENGTH: 1512 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus ( v i i ) IMMEDIATE SOURCE:
        ( B ) CLONE: 303-1-4

( i x ) FEATURE:
        ( A ) NAME/KEY: CDS
        ( B ) LOCATION: 1..1512

( x i ) SEQUENCE DESCRIPTION: SEQ ID NO:5:

```
GAA  TTC  TTC  ACA  GAA  TTG  GAC  GGG  GTG  CGC  CTA  CAT  AGG  TTT  GCG  CCC         48
Glu  Phe  Phe  Thr  Glu  Leu  Asp  Gly  Val  Arg  Leu  His  Arg  Phe  Ala  Pro
 1                    5                      10                          15

CCC  TGC  AAG  CCC  TTG  CTG  CGG  GAG  GAG  GTA  TCA  TTC  AGA  GTA  GGA  CTC         96
Pro  Cys  Lys  Pro  Leu  Leu  Arg  Glu  Glu  Val  Ser  Phe  Arg  Val  Gly  Leu
               20                      25                          30

CAC  GAA  TAC  CCG  GTA  GGG  TCG  CAA  TTA  CCT  TGC  GAG  CCC  GAA  CCG  GAT        144
His  Glu  Tyr  Pro  Val  Gly  Ser  Gln  Leu  Pro  Cys  Glu  Pro  Glu  Pro  Asp
          35                       40                      45

GTG  GCC  GTG  TTG  ACG  TCC  ATG  CTC  ACT  GAT  CCC  TCC  CAT  ATA  ACA  GCA        192
```

-continued

| | | | | | | | | | | | | | | | | |
|---|---|---|---|---|---|---|---|---|---|---|---|---|---|---|---|---|
| | Val | Ala | Val | Leu | Thr | Ser | Met | Leu | Thr | Asp | Pro | Ser | His | Ile | Thr | Ala |
| | | 50 | | | | 55 | | | | | 60 | | | | | |
| GAG | GCG | GCC | GGG | CGA | AGG | TTG | GCG | AGG | GGA | TCA | CCC | CCC | TCT | GTG | GCC | 240 |
| Glu | Ala | Ala | Gly | Arg | Arg | Leu | Ala | Arg | Gly | Ser | Pro | Pro | Ser | Val | Ala | |
| 65 | | | | 70 | | | | | 75 | | | | | 80 | | |
| AGC | TCC | TCG | GCT | AGC | CAG | CTA | TCC | GCT | CCA | TCT | CTC | AAG | GCA | ACT | TGC | 288 |
| Ser | Ser | Ser | Ala | Ser | Gln | Leu | Ser | Ala | Pro | Ser | Leu | Lys | Ala | Thr | Cys | |
| | | | | 85 | | | | | 90 | | | | | 95 | | |
| ACC | GCT | AAC | CAT | GAC | TCC | CCT | GAT | GCT | GAG | CTC | ATA | GAG | GCC | AAC | CTC | 336 |
| Thr | Ala | Asn | His | Asp | Ser | Pro | Asp | Ala | Glu | Leu | Ile | Glu | Ala | Asn | Leu | |
| | | | 100 | | | | | 105 | | | | | 110 | | | |
| CTA | TGG | AGG | CAG | GAG | ATG | GGC | GGC | AAC | ATC | ACC | AGG | GTT | GAG | TCA | GAA | 384 |
| Leu | Trp | Arg | Gln | Glu | Met | Gly | Gly | Asn | Ile | Thr | Arg | Val | Glu | Ser | Glu | |
| | | 115 | | | | | 120 | | | | | 125 | | | | |
| AAC | AAA | GTG | GTG | ATT | CTG | GAC | TCC | TTC | GAT | CCG | CTT | GTG | GCG | GAG | GAG | 432 |
| Asn | Lys | Val | Val | Ile | Leu | Asp | Ser | Phe | Asp | Pro | Leu | Val | Ala | Glu | Glu | |
| | 130 | | | | | 135 | | | | | 140 | | | | | |
| GAC | GAG | CGG | GAG | ATC | TCC | GTA | CCC | GCA | GAA | ATC | CTG | CGG | AAG | TCT | CGG | 480 |
| Asp | Glu | Arg | Glu | Ile | Ser | Val | Pro | Ala | Glu | Ile | Leu | Arg | Lys | Ser | Arg | |
| 145 | | | | | 150 | | | | | 155 | | | | | 160 | |
| AGA | TTC | GCC | CAG | GCC | CTG | CCC | GTT | TGG | GCG | CGG | CCG | GAC | TAT | AAC | CCC | 528 |
| Arg | Phe | Ala | Gln | Ala | Leu | Pro | Val | Trp | Ala | Arg | Pro | Asp | Tyr | Asn | Pro | |
| | | | | 165 | | | | | 170 | | | | | 175 | | |
| CCG | CTA | GTG | GAG | ACG | TGG | AAA | AAG | CCC | GAC | TAC | GAA | CCA | CCT | GTG | GTC | 576 |
| Pro | Leu | Val | Glu | Thr | Trp | Lys | Lys | Pro | Asp | Tyr | Glu | Pro | Pro | Val | Val | |
| | | | 180 | | | | | 185 | | | | | 190 | | | |
| CAT | GGC | TGT | CCG | CTT | CCA | CCT | CCA | AAG | TCC | CCT | CCT | GTG | CCT | CCG | CCT | 624 |
| His | Gly | Cys | Pro | Leu | Pro | Pro | Pro | Lys | Ser | Pro | Pro | Val | Pro | Pro | Pro | |
| | | 195 | | | | | 200 | | | | | 205 | | | | |
| CGG | AAG | AAG | CGG | ACG | GTG | GTC | CTC | ACT | GAA | TCA | ACC | CTA | TCT | ACT | GCC | 672 |
| Arg | Lys | Lys | Arg | Thr | Val | Val | Leu | Thr | Glu | Ser | Thr | Leu | Ser | Thr | Ala | |
| | 210 | | | | | 215 | | | | | 220 | | | | | |
| TTG | GCC | GAG | CTC | GCC | ACC | AGA | AGC | TTT | GGC | AGC | TCC | TCA | ACT | TCC | GGC | 720 |
| Leu | Ala | Glu | Leu | Ala | Thr | Arg | Ser | Phe | Gly | Ser | Ser | Ser | Thr | Ser | Gly | |
| 225 | | | | | 230 | | | | | 235 | | | | | 240 | |
| ATT | ACG | GGC | GAC | AAT | ACG | ACA | ACA | TCC | TCT | GAG | CCC | GCC | CCT | TCT | GGC | 768 |
| Ile | Thr | Gly | Asp | Asn | Thr | Thr | Thr | Ser | Ser | Glu | Pro | Ala | Pro | Ser | Gly | |
| | | | | 245 | | | | | 250 | | | | | 255 | | |
| TGC | CCC | CCC | GAC | TCC | GAC | GCT | GAG | TCC | TAT | TCC | TCC | ATG | CCC | CCC | CTG | 816 |
| Cys | Pro | Pro | Asp | Ser | Asp | Ala | Glu | Ser | Tyr | Ser | Ser | Met | Pro | Pro | Leu | |
| | | | 260 | | | | | 265 | | | | | 270 | | | |
| GAG | GGG | GAG | CCT | GGG | GAT | CCG | GAT | CTT | AGC | GAC | GGG | TCA | TGG | TCA | ACG | 864 |
| Glu | Gly | Glu | Pro | Gly | Asp | Pro | Asp | Leu | Ser | Asp | Gly | Ser | Trp | Ser | Thr | |
| | | 275 | | | | | 280 | | | | | 285 | | | | |
| GTC | AGT | AGT | GAG | GCC | AAC | GCG | GAG | GAT | GTC | GTG | TGC | TGC | TCA | ATG | TCT | 912 |
| Val | Ser | Ser | Glu | Ala | Asn | Ala | Glu | Asp | Val | Val | Cys | Cys | Ser | Met | Ser | |
| | 290 | | | | | 295 | | | | | 300 | | | | | |
| TAC | TCT | TGG | ACA | GGC | GCA | CTC | GTC | ACC | CCG | TGC | GCC | GCG | GAA | GAA | CAG | 960 |
| Tyr | Ser | Trp | Thr | Gly | Ala | Leu | Val | Thr | Pro | Cys | Ala | Ala | Glu | Glu | Gln | |
| 305 | | | | | 310 | | | | | 315 | | | | | 320 | |
| AAA | CTG | CCC | ATC | AAT | GCA | CTA | AGC | AAC | TCG | TTG | CTA | CGT | CAC | CAC | AAT | 1008 |
| Lys | Leu | Pro | Ile | Asn | Ala | Leu | Ser | Asn | Ser | Leu | Leu | Arg | His | His | Asn | |
| | | | | 325 | | | | | 330 | | | | | 335 | | |
| TTG | GTG | TAT | TCC | ACC | ACC | TCA | CGC | AGT | GCT | TGC | CAA | AGG | CAG | AAG | AAA | 1056 |
| Leu | Val | Tyr | Ser | Thr | Thr | Ser | Arg | Ser | Ala | Cys | Gln | Arg | Gln | Lys | Lys | |
| | | | 340 | | | | | 345 | | | | | 350 | | | |
| GTC | ACA | TTT | GAC | AGA | CTG | CAA | GTT | CTG | GAC | AGC | CAT | TAC | CAG | GAC | GTA | 1104 |
| Val | Thr | Phe | Asp | Arg | Leu | Gln | Val | Leu | Asp | Ser | His | Tyr | Gln | Asp | Val | |
| | | 355 | | | | | 360 | | | | | 365 | | | | |
| CTC | AAG | GAG | GTT | AAA | GCA | GCG | GCG | TCA | AAA | GTG | AAG | GCT | AAC | TTG | CTA | 1152 |

| | | | | | | | | | | | | | | |
|---|---|---|---|---|---|---|---|---|---|---|---|---|---|---|
| Leu | Lys | Glu | Val | Lys | Ala | Ala | Ala | Ser | Lys | Val | Lys | Ala | Asn | Leu | Leu |
| | 370 | | | | 375 | | | | | 380 | | | | | |

| TCC | GTA | GAG | GAA | GCT | TGC | AGC | CTG | ACG | CCC | CCA | CAC | TCA | GCC | AAA | TCC | 1200 |
|---|---|---|---|---|---|---|---|---|---|---|---|---|---|---|---|---|
| Ser | Val | Glu | Glu | Ala | Cys | Ser | Leu | Thr | Pro | Pro | His | Ser | Ala | Lys | Ser | |
| 385 | | | | | 390 | | | | | 395 | | | | | 400 | |

| AAG | TTT | GGT | TAT | GGG | GCA | AAA | GAC | GTC | CGT | TGC | CAT | GCC | AGA | AAG | GCC | 1248 |
|---|---|---|---|---|---|---|---|---|---|---|---|---|---|---|---|---|
| Lys | Phe | Gly | Tyr | Gly | Ala | Lys | Asp | Val | Arg | Cys | His | Ala | Arg | Lys | Ala | |
| | | | | 405 | | | | | 410 | | | | | 415 | | |

| GTA | ACC | CAC | ATC | AAC | TCC | GTG | TGG | AAA | GAC | CTT | CTG | GAA | GAC | AAT | GTA | 1296 |
|---|---|---|---|---|---|---|---|---|---|---|---|---|---|---|---|---|
| Val | Thr | His | Ile | Asn | Ser | Val | Trp | Lys | Asp | Leu | Leu | Glu | Asp | Asn | Val | |
| | | | 420 | | | | | 425 | | | | | 430 | | | |

| ACA | CCA | ATA | GAC | ACT | ACC | ATC | ATG | GCT | AAG | AAC | GAG | GTT | TTC | TGC | GTT | 1344 |
|---|---|---|---|---|---|---|---|---|---|---|---|---|---|---|---|---|
| Thr | Pro | Ile | Asp | Thr | Thr | Ile | Met | Ala | Lys | Asn | Glu | Val | Phe | Cys | Val | |
| | | 435 | | | | | 440 | | | | | 445 | | | | |

| CAG | CCT | GAG | AAG | GGG | GGT | CGT | AAG | CCA | GCT | CGT | CTC | ATC | GTG | TTC | CCC | 1392 |
|---|---|---|---|---|---|---|---|---|---|---|---|---|---|---|---|---|
| Gln | Pro | Glu | Lys | Gly | Gly | Arg | Lys | Pro | Ala | Arg | Leu | Ile | Val | Phe | Pro | |
| 450 | | | | | 455 | | | | | 460 | | | | | | |

| GAT | CTG | GGC | GTG | CGC | GTG | TGC | GAA | AAG | ATG | GCT | TTG | TAC | GAC | GTG | GTT | 1440 |
|---|---|---|---|---|---|---|---|---|---|---|---|---|---|---|---|---|
| Asp | Leu | Gly | Val | Arg | Val | Cys | Glu | Lys | Met | Ala | Leu | Tyr | Asp | Val | Val | |
| 465 | | | | | 470 | | | | | 475 | | | | | 480 | |

| ACC | AAG | CTC | CCC | TTG | GCC | GTG | ATG | GGA | AGC | TCC | TAC | GGA | TTC | CAA | TAC | 1488 |
|---|---|---|---|---|---|---|---|---|---|---|---|---|---|---|---|---|
| Thr | Lys | Leu | Pro | Leu | Ala | Val | Met | Gly | Ser | Ser | Tyr | Gly | Phe | Gln | Tyr | |
| | | | | 485 | | | | | 490 | | | | | 495 | | |

| TCA | CCA | GGA | CAG | CGG | GTT | GAA | TTC | | | | | | | | | 1512 |
|---|---|---|---|---|---|---|---|---|---|---|---|---|---|---|---|---|
| Ser | Pro | Gly | Gln | Arg | Val | Glu | Phe | | | | | | | | | |
| | | | 500 | | | | | | | | | | | | | |

( 2 ) INFORMATION FOR SEQ ID NO:6:

( i ) SEQUENCE CHARACTERISTICS:
        ( A ) LENGTH: 504 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Glu | Phe | Phe | Thr | Glu | Leu | Asp | Gly | Val | Arg | Leu | His | Arg | Phe | Ala | Pro |
| 1 | | | | 5 | | | | | 10 | | | | | 15 | |

| Pro | Cys | Lys | Pro | Leu | Leu | Arg | Glu | Glu | Val | Ser | Phe | Arg | Val | Gly | Leu |
|---|---|---|---|---|---|---|---|---|---|---|---|---|---|---|---|
| | | | 20 | | | | | 25 | | | | | 30 | | |

| His | Glu | Tyr | Pro | Val | Gly | Ser | Gln | Leu | Pro | Cys | Glu | Pro | Glu | Pro | Asp |
|---|---|---|---|---|---|---|---|---|---|---|---|---|---|---|---|
| | | | 35 | | | | | 40 | | | | | 45 | | |

| Val | Ala | Val | Leu | Thr | Ser | Met | Leu | Thr | Asp | Pro | Ser | His | Ile | Thr | Ala |
|---|---|---|---|---|---|---|---|---|---|---|---|---|---|---|---|
| | 50 | | | | | 55 | | | | | 60 | | | | |

| Glu | Ala | Ala | Gly | Arg | Arg | Leu | Ala | Arg | Gly | Ser | Pro | Pro | Ser | Val | Ala |
|---|---|---|---|---|---|---|---|---|---|---|---|---|---|---|---|
| 65 | | | | | 70 | | | | | 75 | | | | | 80 |

| Ser | Ser | Ser | Ala | Ser | Gln | Leu | Ser | Ala | Pro | Ser | Leu | Lys | Ala | Thr | Cys |
|---|---|---|---|---|---|---|---|---|---|---|---|---|---|---|---|
| | | | | 85 | | | | | 90 | | | | | 95 | |

| Thr | Ala | Asn | His | Asp | Ser | Pro | Asp | Ala | Glu | Leu | Ile | Glu | Ala | Asn | Leu |
|---|---|---|---|---|---|---|---|---|---|---|---|---|---|---|---|
| | | | 100 | | | | | 105 | | | | | 110 | | |

| Leu | Trp | Arg | Gln | Glu | Met | Gly | Gly | Asn | Ile | Thr | Arg | Val | Glu | Ser | Glu |
|---|---|---|---|---|---|---|---|---|---|---|---|---|---|---|---|
| | | 115 | | | | | 120 | | | | | 125 | | | |

| Asn | Lys | Val | Val | Ile | Leu | Asp | Ser | Phe | Asp | Pro | Leu | Val | Ala | Glu | Glu |
|---|---|---|---|---|---|---|---|---|---|---|---|---|---|---|---|
| | 130 | | | | | 135 | | | | | 140 | | | | |

| Asp | Glu | Arg | Glu | Ile | Ser | Val | Pro | Ala | Glu | Ile | Leu | Arg | Lys | Ser | Arg |
|---|---|---|---|---|---|---|---|---|---|---|---|---|---|---|---|
| 145 | | | | | 150 | | | | | 155 | | | | | 160 |

| Arg | Phe | Ala | Gln | Ala | Leu | Pro | Val | Trp | Ala | Arg | Pro | Asp | Tyr | Asn | Pro |
|---|---|---|---|---|---|---|---|---|---|---|---|---|---|---|---|
| | | | | 165 | | | | | 170 | | | | | 175 | |

| Pro | Leu | Val | Glu | Thr | Trp | Lys | Lys | Pro | Asp | Tyr | Glu | Pro | Val | Val |
|---|---|---|---|---|---|---|---|---|---|---|---|---|---|---|
| | | | 180 | | | | 185 | | | | | 190 | | |
| His | Gly | Cys | Pro | Leu | Pro | Pro | Pro | Lys | Ser | Pro | Pro | Val | Pro | Pro | Pro |
| | | 195 | | | | 200 | | | | | 205 | | | | |
| Arg | Lys | Lys | Arg | Thr | Val | Val | Leu | Thr | Glu | Ser | Thr | Leu | Ser | Thr | Ala |
| | 210 | | | | | 215 | | | | | 220 | | | | |
| Leu | Ala | Glu | Leu | Ala | Thr | Arg | Ser | Phe | Gly | Ser | Ser | Ser | Thr | Ser | Gly |
| 225 | | | | | 230 | | | | | 235 | | | | | 240 |
| Ile | Thr | Gly | Asp | Asn | Thr | Thr | Thr | Ser | Ser | Glu | Pro | Ala | Pro | Ser | Gly |
| | | | | 245 | | | | | 250 | | | | | 255 | |
| Cys | Pro | Pro | Asp | Ser | Asp | Ala | Glu | Ser | Tyr | Ser | Ser | Met | Pro | Pro | Leu |
| | | | 260 | | | | | 265 | | | | | 270 | | |
| Glu | Gly | Glu | Pro | Gly | Asp | Pro | Asp | Leu | Ser | Asp | Gly | Ser | Trp | Ser | Thr |
| | | 275 | | | | | 280 | | | | | 285 | | | |
| Val | Ser | Ser | Glu | Ala | Asn | Ala | Glu | Asp | Val | Val | Cys | Cys | Ser | Met | Ser |
| | 290 | | | | | 295 | | | | | 300 | | | | |
| Tyr | Ser | Trp | Thr | Gly | Ala | Leu | Val | Thr | Pro | Cys | Ala | Ala | Glu | Glu | Gln |
| 305 | | | | | 310 | | | | | 315 | | | | | 320 |
| Lys | Leu | Pro | Ile | Asn | Ala | Leu | Ser | Asn | Ser | Leu | Leu | Arg | His | His | Asn |
| | | | | 325 | | | | | 330 | | | | | 335 | |
| Leu | Val | Tyr | Ser | Thr | Thr | Ser | Arg | Ser | Ala | Cys | Gln | Arg | Gln | Lys | Lys |
| | | | 340 | | | | | 345 | | | | | 350 | | |
| Val | Thr | Phe | Asp | Arg | Leu | Gln | Val | Leu | Asp | Ser | His | Tyr | Gln | Asp | Val |
| | | 355 | | | | | 360 | | | | | 365 | | | |
| Leu | Lys | Glu | Val | Lys | Ala | Ala | Ala | Ser | Lys | Val | Lys | Ala | Asn | Leu | Leu |
| | 370 | | | | 375 | | | | | 380 | | | | | |
| Ser | Val | Glu | Glu | Ala | Cys | Ser | Leu | Thr | Pro | Pro | His | Ser | Ala | Lys | Ser |
| 385 | | | | | 390 | | | | | 395 | | | | | 400 |
| Lys | Phe | Gly | Tyr | Gly | Ala | Lys | Asp | Val | Arg | Cys | His | Ala | Arg | Lys | Ala |
| | | | | 405 | | | | | 410 | | | | | 415 | |
| Val | Thr | His | Ile | Asn | Ser | Val | Trp | Lys | Asp | Leu | Leu | Glu | Asp | Asn | Val |
| | | | 420 | | | | | 425 | | | | | 430 | | |
| Thr | Pro | Ile | Asp | Thr | Thr | Ile | Met | Ala | Lys | Asn | Glu | Val | Phe | Cys | Val |
| | | 435 | | | | | 440 | | | | | 445 | | | |
| Gln | Pro | Glu | Lys | Gly | Gly | Arg | Lys | Pro | Ala | Arg | Leu | Ile | Val | Phe | Pro |
| | 450 | | | | | 455 | | | | | 460 | | | | |
| Asp | Leu | Gly | Val | Arg | Val | Cys | Glu | Lys | Met | Ala | Leu | Tyr | Asp | Val | Val |
| 465 | | | | | 470 | | | | | 475 | | | | | 480 |
| Thr | Lys | Leu | Pro | Leu | Ala | Val | Met | Gly | Ser | Ser | Tyr | Gly | Phe | Gln | Tyr |
| | | | | 485 | | | | | 490 | | | | | 495 | |
| Ser | Pro | Gly | Gln | Arg | Val | Glu | Phe |
| | | | 500 | | | | |

( 2 ) INFORMATION FOR SEQ ID NO:7:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus (B) STRAIN: CDC
(C) INDIVIDUAL ISOLATE: Rodney (vii) IMMEDIATE SOURCE:
(B) CLONE: 409-1-1 (c-a)

(ix) FEATURE:
(A) NAME/KEY: CDS
(B) LOCATION: 1..477

(xi) SEQUENCE DESCRIPTION: SEQ ID NO:7:

| GAA | TTC | CGC | ACG | CCC | GCC | GAG | ACT | ACA | GTT | AGG | CTA | CGG | GCG | TAC | ATG | 48 |
|---|---|---|---|---|---|---|---|---|---|---|---|---|---|---|---|---|
| Glu | Phe | Arg | Thr | Pro | Ala | Glu | Thr | Thr | Val | Arg | Leu | Arg | Ala | Tyr | Met | |
| 1 | | | | 5 | | | | | 10 | | | | | 15 | | |

| AAC | ACT | CCG | GGG | CTT | CCC | GTG | TGC | CAG | GAC | GGA | ATT | CCG | TCC | CCG | TCC | 96 |
|---|---|---|---|---|---|---|---|---|---|---|---|---|---|---|---|---|
| Asn | Thr | Pro | Gly | Leu | Pro | Val | Cys | Gln | Asp | Gly | Ile | Pro | Ser | Pro | Ser | |
| | | | 20 | | | | | 25 | | | | | 30 | | | |

| ACC | ACC | GGA | GAG | ATC | CCT | TTT | TAC | GGC | AAG | GCT | ATC | CCC | CTC | GAA | GTA | 144 |
|---|---|---|---|---|---|---|---|---|---|---|---|---|---|---|---|---|
| Thr | Thr | Gly | Glu | Ile | Pro | Phe | Tyr | Gly | Lys | Ala | Ile | Pro | Leu | Glu | Val | |
| | | 35 | | | | | 40 | | | | | 45 | | | | |

| ATC | AAG | GGG | GGG | AGA | CAT | CTC | ATC | TTC | TGT | CAT | TCA | AAG | AAG | AAG | TGC | 192 |
|---|---|---|---|---|---|---|---|---|---|---|---|---|---|---|---|---|
| Ile | Lys | Gly | Gly | Arg | His | Leu | Ile | Phe | Cys | His | Ser | Lys | Lys | Lys | Cys | |
| | 50 | | | | | 55 | | | | | 60 | | | | | |

| GAC | GAA | CTC | GCC | GCA | AAG | CTG | GTC | GCA | TTG | GGC | ATC | AAT | GCC | GTG | GCC | 240 |
|---|---|---|---|---|---|---|---|---|---|---|---|---|---|---|---|---|
| Asp | Glu | Leu | Ala | Ala | Lys | Leu | Val | Ala | Leu | Gly | Ile | Asn | Ala | Val | Ala | |
| 65 | | | | | 70 | | | | | 75 | | | | | 80 | |

| TAC | TAC | CGC | GGT | CTT | GAC | GTG | TCC | GTC | ATC | CCG | ACC | AGC | GGC | GAT | GTT | 288 |
|---|---|---|---|---|---|---|---|---|---|---|---|---|---|---|---|---|
| Tyr | Tyr | Arg | Gly | Leu | Asp | Val | Ser | Val | Ile | Pro | Thr | Ser | Gly | Asp | Val | |
| | | | | 85 | | | | | 90 | | | | | 95 | | |

| GTC | GTC | GTG | GCA | ACC | GAT | GCC | CTC | ATG | ACC | GGC | TAT | ACC | GGC | GAC | TTC | 336 |
|---|---|---|---|---|---|---|---|---|---|---|---|---|---|---|---|---|
| Val | Val | Val | Ala | Thr | Asp | Ala | Leu | Met | Thr | Gly | Tyr | Thr | Gly | Asp | Phe | |
| | | | 100 | | | | | 105 | | | | | 110 | | | |

| GAC | TCG | GTG | ATA | GAC | TGC | AAT | ACG | TGT | GTC | ACC | CAG | ACA | GTC | GAT | TTC | 384 |
|---|---|---|---|---|---|---|---|---|---|---|---|---|---|---|---|---|
| Asp | Ser | Val | Ile | Asp | Cys | Asn | Thr | Cys | Val | Thr | Gln | Thr | Val | Asp | Phe | |
| | | 115 | | | | | 120 | | | | | 125 | | | | |

| AGC | CTT | GAC | CCT | ACC | TTC | ACC | ATT | GAG | ACA | ATC | ACG | CTC | CCC | CAG | GAT | 432 |
|---|---|---|---|---|---|---|---|---|---|---|---|---|---|---|---|---|
| Ser | Leu | Asp | Pro | Thr | Phe | Thr | Ile | Glu | Thr | Ile | Thr | Leu | Pro | Gln | Asp | |
| | 130 | | | | | 135 | | | | | 140 | | | | | |

| GCT | GTC | TCC | CGC | ACT | CAA | CGT | CGG | GGC | AGG | ACT | GGC | ACG | GAA | TTC | | 477 |
|---|---|---|---|---|---|---|---|---|---|---|---|---|---|---|---|---|
| Ala | Val | Ser | Arg | Thr | Gln | Arg | Arg | Gly | Arg | Thr | Gly | Thr | Glu | Phe | | |
| 145 | | | | | 150 | | | | | 155 | | | | | | |

(2) INFORMATION FOR SEQ ID NO:8:

(i) SEQUENCE CHARACTERISTICS:
(A) LENGTH: 159 amino acids
(B) TYPE: amino acid
(D) TOPOLOGY: linear (ii) MOLECULE TYPE: protein (xi) SEQUENCE DESCRIPTION: SEQ ID NO:8:

| Glu | Phe | Arg | Thr | Pro | Ala | Glu | Thr | Thr | Val | Arg | Leu | Arg | Ala | Tyr | Met |
|---|---|---|---|---|---|---|---|---|---|---|---|---|---|---|---|
| 1 | | | | 5 | | | | | 10 | | | | | 15 | |

| Asn | Thr | Pro | Gly | Leu | Pro | Val | Cys | Gln | Asp | Gly | Ile | Pro | Ser | Pro | Ser |
|---|---|---|---|---|---|---|---|---|---|---|---|---|---|---|---|
| | | | 20 | | | | | 25 | | | | | 30 | | |

| Thr | Thr | Gly | Glu | Ile | Pro | Phe | Tyr | Gly | Lys | Ala | Ile | Pro | Leu | Glu | Val |
|---|---|---|---|---|---|---|---|---|---|---|---|---|---|---|---|
| | | 35 | | | | | 40 | | | | | 45 | | | |

| Ile | Lys | Gly | Gly | Arg | His | Leu | Ile | Phe | Cys | His | Ser | Lys | Lys | Lys | Cys |
|---|---|---|---|---|---|---|---|---|---|---|---|---|---|---|---|
| | 50 | | | | | 55 | | | | | 60 | | | | |

| Asp | Glu | Leu | Ala | Ala | Lys | Leu | Val | Ala | Leu | Gly | Ile | Asn | Ala | Val | Ala |
|---|---|---|---|---|---|---|---|---|---|---|---|---|---|---|---|
| 65 | | | | | 70 | | | | | 75 | | | | | 80 |

| Tyr | Tyr | Arg | Gly | Leu | Asp | Val | Ser | Val | Ile | Pro | Thr | Ser | Gly | Asp | Val |
|---|---|---|---|---|---|---|---|---|---|---|---|---|---|---|---|

|    |    |    | 85 |    |    |    |    | 90 |    |    |    |    | 95 |    |    |
|----|----|----|----|----|----|----|----|----|----|----|----|----|----|----|----|

Val Val Val Ala Thr Asp Ala Leu Met Thr Gly Tyr Thr Gly Asp Phe
              100             105               110

Asp Ser Val Ile Asp Cys Asn Thr Cys Val Thr Gln Thr Val Asp Phe
         115             120             125

Ser Leu Asp Pro Thr Phe Thr Ile Glu Thr Ile Thr Leu Pro Gln Asp
     130             135             140

Ala Val Ser Arg Thr Gln Arg Arg Gly Arg Thr Gly Thr Glu Phe
145              150              155

(2) INFORMATION FOR SEQ ID NO:9:

(i) SEQUENCE CHARACTERISTICS:
        (A) LENGTH: 558 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
        (A) ORGANISM: Hepatitis C Virus
        (B) STRAIN: CDC (vii) IMMEDIATE SOURCE:
        (B)

| | | | | | | | | | | | | | | | |
|---|---|---|---|---|---|---|---|---|---|---|---|---|---|---|---|
| TAT | GAG | CTC | ACG | CCC | GCC | GAG | ACT | ACA | GTT | AGG | CTA | CGA | GCG | TAC | ATG | 528 |
| Tyr | Glu | Leu | Thr | Pro | Ala | Glu | Thr | Thr | Val | Arg | Leu | Arg | Ala | Tyr | Met | |
| | | | | 165 | | | | 170 | | | | | | 175 | | |
| AAC | ACC | CCG | GGG | CTT | CCC | GTG | TGC | CAG | GAC | | | | | | | 558 |
| Asn | Thr | Pro | Gly | Leu | Pro | Val | Cys | Gln | Asp | | | | | | | |
| | | | 180 | | | | | 185 | | | | | | | | |

( 2 ) INFORMATION FOR SEQ ID NO:10:

( i ) SEQUENCE CHARACTERISTICS:
        ( A ) LENGTH: 186 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Ser | Thr | Thr | Gly | Glu | Ile | Pro | Phe | Tyr | Gly | Lys | Ala | Ile | Pro | Leu | Glu |
|---|---|---|---|---|---|---|---|---|---|---|---|---|---|---|---|
| 1 | | | | 5 | | | | | 10 | | | | | 15 | |
| Val | Ile | Lys | Gly | Gly | Arg | His | Leu | Ile | Phe | Cys | His | Ser | Lys | Lys | Lys |
| | | | 20 | | | | | 25 | | | | | 30 | | |
| Cys | Asp | Glu | Leu | Ala | Ala | Lys | Leu | Val | Ala | Leu | Gly | Ile | Asn | Ala | Val |
| | | | 35 | | | | 40 | | | | | 45 | | | |
| Ala | Tyr | Tyr | Arg | Gly | Leu | Asp | Val | Ser | Val | Ile | Pro | Thr | Ser | Gly | Asp |
| | | 50 | | | | 55 | | | | | 60 | | | | |
| Val | Val | Val | Val | Ala | Thr | Asp | Ala | Leu | Met | Thr | Gly | Tyr | Thr | Gly | Asp |
| 65 | | | | | 70 | | | | | 75 | | | | | 80 |
| Phe | Asp | Ser | Val | Ile | Asp | Cys | Asn | Thr | Cys | Val | Thr | Gln | Thr | Val | Asp |
| | | | | 85 | | | | | 90 | | | | | 95 | |
| Phe | Ser | Leu | Asp | Pro | Thr | Phe | Thr | Ile | Glu | Thr | Ile | Thr | Leu | Pro | Gln |
| | | | | 100 | | | | 105 | | | | | 110 | | |
| Asp | Ala | Val | Ser | Arg | Thr | Gln | Arg | Arg | Gly | Arg | Thr | Gly | Arg | Gly | Lys |
| | | | 115 | | | | 120 | | | | | 125 | | | |
| Pro | Gly | Ile | Tyr | Arg | Phe | Val | Ala | Pro | Gly | Glu | Arg | Pro | Ser | Gly | Met |
| | | 130 | | | | 135 | | | | | 140 | | | | |
| Phe | Asp | Ser | Ser | Val | Leu | Cys | Glu | Cys | Tyr | Asp | Ala | Gly | Cys | Ala | Trp |
| 145 | | | | | 150 | | | | | 155 | | | | | 160 |
| Tyr | Glu | Leu | Thr | Pro | Ala | Glu | Thr | Thr | Val | Arg | Leu | Arg | Ala | Tyr | Met |
| | | | | 165 | | | | 170 | | | | | | 175 | |
| Asn | Thr | Pro | Gly | Leu | Pro | Val | Cys | Gln | Asp | | | | | | |
| | | | 180 | | | | | 185 | | | | | | | |

( 2 ) INFORMATION FOR SEQ ID NO:11:

( i ) SEQUENCE CHARACTERISTICS:
        ( A ) LENGTH: 657 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus
        ( B ) STRAIN: CDC ( v i i ) IMMEDIATE SOURCE:
        ( B ) CLONE: GG1

( i x ) FEATURE:
        ( A ) NAME/KEY: CDS ( B ) LOCATION: 1..657

( x i ) SEQUENCE DESCRIPTION: SEQ ID NO:11:

| | | | | | | | | | | | | | | | | |
|---|---|---|---|---|---|---|---|---|---|---|---|---|---|---|---|---|
| ATG | GGC | ACG | AAT | CCT | AAA | CCT | CAA | AAA | AAA | AAC | AAA | CGT | AAC | ACC | AAC | 48 |
| Met | Gly | Thr | Asn | Pro | Lys | Pro | Gln | Lys | Lys | Asn | Lys | Arg | Asn | Thr | Asn | |
| 1 | | | | 5 | | | | | 10 | | | | | | 15 | |
| CGT | CGC | CCA | CAG | GAC | GTC | AAG | TTC | CCG | GGT | GGC | GGT | CAG | ATC | GTT | GGT | 96 |
| Arg | Arg | Pro | Gln | Asp | Val | Lys | Phe | Pro | Gly | Gly | Gly | Gln | Ile | Val | Gly | |
| | | | 20 | | | | | 25 | | | | | 30 | | | |
| GGA | GTT | TAC | TTG | TTG | CCG | CGC | AGG | GGC | CCT | AGA | TTG | GGT | GTG | CGC | GCG | 144 |
| Gly | Val | Tyr | Leu | Leu | Pro | Arg | Arg | Gly | Pro | Arg | Leu | Gly | Val | Arg | Ala | |
| | | 35 | | | | | 40 | | | | | 45 | | | | |
| ACG | AGA | AAG | ACT | TCC | GAG | CGG | TCG | CAA | CCT | CGA | GGT | AGA | CGT | CAG | CCT | 192 |
| Thr | Arg | Lys | Thr | Ser | Glu | Arg | Ser | Gln | Pro | Arg | Gly | Arg | Arg | Gln | Pro | |
| | 50 | | | | | 55 | | | | | 60 | | | | | |
| ATC | CCC | AAG | GCT | CGT | CGG | CCC | GAG | GGC | AGG | ACC | TGG | GCT | CAG | CCC | GGG | 240 |
| Ile | Pro | Lys | Ala | Arg | Arg | Pro | Glu | Gly | Arg | Thr | Trp | Ala | Gln | Pro | Gly | |
| 65 | | | | | 70 | | | | | 75 | | | | | 80 | |
| TAC | CCT | TGG | CCC | CTC | TAT | GGC | AAT | GAG | GGC | TGC | GGG | TGG | GCG | GGA | TGG | 288 |
| Tyr | Pro | Trp | Pro | Leu | Tyr | Gly | Asn | Glu | Gly | Cys | Gly | Trp | Ala | Gly | Trp | |
| | | | | 85 | | | | | 90 | | | | | 95 | | |
| CTC | CTG | TCT | CCC | CGT | GGC | TCT | CGG | CCT | AGC | TGG | GGC | CCC | ACA | GAC | CCC | 336 |
| Leu | Leu | Ser | Pro | Arg | Gly | Ser | Arg | Pro | Ser | Trp | Gly | Pro | Thr | Asp | Pro | |
| | | | 100 | | | | | 105 | | | | | 110 | | | |
| CGG | CGT | AGG | TCG | CGC | AAT | TTG | GGT | AAG | GTC | ATC | GAT | ACC | CTT | ACG | TGC | 384 |
| Arg | Arg | Arg | Ser | Arg | Asn | Leu | Gly | Lys | Val | Ile | Asp | Thr | Leu | Thr | Cys | |
| | | 115 | | | | | 120 | | | | | 125 | | | | |
| GGC | TTC | GCC | GAC | CTC | ATG | GGG | TAC | ATA | CCG | CTC | GTC | GGC | GCC | CCT | CTT | 432 |
| Gly | Phe | Ala | Asp | Leu | Met | Gly | Tyr | Ile | Pro | Leu | Val | Gly | Ala | Pro | Leu | |
| | 130 | | | | | 135 | | | | | 140 | | | | | |
| GGA | GGC | GCT | GCC | AGG | GCC | CTG | GCG | CAT | GGC | GTC | CGG | GTT | CTG | GAA | GAC | 480 |
| Gly | Gly | Ala | Ala | Arg | Ala | Leu | Ala | His | Gly | Val | Arg | Val | Leu | Glu | Asp | |
| 145 | | | | | 150 | | | | | 155 | | | | | 160 | |
| GGC | GTG | AAC | TAT | GCA | ACA | GGG | AAC | CTT | CCT | GGT | TGC | TCT | TTC | TCT | ATC | 528 |
| Gly | Val | Asn | Tyr | Ala | Thr | Gly | Asn | Leu | Pro | Gly | Cys | Ser | Phe | Ser | Ile | |
| | | | | 165 | | | | | 170 | | | | | 175 | | |
| TTC | CTT | CTG | GCC | CTG | CTC | TCT | TGC | TTG | ACT | GTG | CCC | GCT | TCG | GCC | TAC | 576 |
| Phe | Leu | Leu | Ala | Leu | Leu | Ser | Cys | Leu | Thr | Val | Pro | Ala | Ser | Ala | Tyr | |
| | | | 180 | | | | | 185 | | | | | 190 | | | |
| CAA | GTG | CGC | AAC | TCC | ACG | GGG | CTT | TAC | CAC | GTC | ACC | AAT | GAT | TGC | CCT | 624 |
| Gln | Val | Arg | Asn | Ser | Thr | Gly | Leu | Tyr | His | Val | Thr | Asn | Asp | Cys | Pro | |
| | | 195 | | | | | 200 | | | | | 205 | | | | |
| AAC | TCG | AGC | ATT | GTG | TAC | GAG | TAA | TAG | GGA | TCC | | | | | | 657 |
| Asn | Ser | Ser | Ile | Val | Tyr | Glu | | | Gly | Ser | | | | | | |
| | 210 | | | | | 215 | | | | | | | | | | |

( 2 ) INFORMATION FOR SEQ ID NO:12:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | | |
|---|---|---|---|---|---|---|---|---|---|---|---|---|---|---|---|
| Met | Gly | Thr | Asn | Pro | Lys | Pro | Gln | Lys | Lys | Asn | Lys | Arg | Asn | Thr | Asn |
| 1 | | | | 5 | | | | | 10 | | | | | | 15 |
| Arg | Arg | Pro | Gln | Asp | Val | Lys | Phe | Pro | Gly | Gly | Gly | Gln | Ile | Val | Gly |
| | | | 20 | | | | | 25 | | | | | 30 | | |
| Gly | Val | Tyr | Leu | Leu | Pro | Arg | Arg | Gly | Pro | Arg | Leu | Gly | Val | Arg | Ala |
| | | 35 | | | | | 40 | | | | | 45 | | | |

| | | | | | | | | | | | | | | |
|---|---|---|---|---|---|---|---|---|---|---|---|---|---|---|
| Thr | Arg | Lys | Thr | Ser | Glu | Arg | Ser | Gln | Pro | Arg | Gly | Arg | Arg | Gln | Pro |
| | | 50 | | | | 55 | | | | | 60 | | | | |
| Ile | Pro | Lys | Ala | Arg | Arg | Pro | Glu | Gly | Arg | Thr | Trp | Ala | Gln | Pro | Gly |
| 65 | | | | | 70 | | | | | 75 | | | | | 80 |
| Tyr | Pro | Trp | Pro | Leu | Tyr | Gly | Asn | Glu | Gly | Cys | Gly | Trp | Ala | Gly | Trp |
| | | | | 85 | | | | | 90 | | | | | 95 | |
| Leu | Leu | Ser | Pro | Arg | Gly | Ser | Arg | Pro | Ser | Trp | Gly | Pro | Thr | Asp | Pro |
| | | | 100 | | | | | 105 | | | | | 110 | | |
| Arg | Arg | Arg | Ser | Arg | Asn | Leu | Gly | Lys | Val | Ile | Asp | Thr | Leu | Thr | Cys |
| | | 115 | | | | | 120 | | | | | 125 | | | |
| Gly | Phe | Ala | Asp | Leu | Met | Gly | Tyr | Ile | Pro | Leu | Val | Gly | Ala | Pro | Leu |
| | 130 | | | | | 135 | | | | | 140 | | | | |
| Gly | Gly | Ala | Ala | Arg | Ala | Leu | Ala | His | Gly | Val | Arg | Val | Leu | Glu | Asp |
| 145 | | | | | 150 | | | | | 155 | | | | | 160 |
| Gly | Val | Asn | Tyr | Ala | Thr | Gly | Asn | Leu | Pro | Gly | Cys | Ser | Phe | Ser | Ile |
| | | | | 165 | | | | | 170 | | | | | 175 | |
| Phe | Leu | Leu | Ala | Leu | Leu | Ser | Cys | Leu | Thr | Val | Pro | Ala | Ser | Ala | Tyr |
| | | | | 180 | | | | | 185 | | | | | 190 | |
| Gln | Val | Arg | Asn | Ser | Thr | Gly | Leu | Tyr | His | Val | Thr | Asn | Asp | Cys | Pro |
| | | 195 | | | | | 200 | | | | | 205 | | | |
| Asn | Ser | Ser | Ile | Val | Tyr | Glu | Gly | Ser | | | | | | | |
| | 210 | | | | | 215 | | | | | | | | | |

( 2 ) INFORMATION FOR SEQ ID NO:13:

( i ) SEQUENCE CHARACTERISTICS:
        ( A ) LENGTH: 657 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus
        ( B ) STRAIN: CDC ( v i i ) IMMEDIATE SOURCE:
        ( B ) CLONE: CapA ( i x ) FEATURE:
        ( A ) NAME/KEY: CDS
        ( B ) LOCATION: 1..657

( x i ) SEQUENCE DESCRIPTION: SEQ ID NO:13:

| | | | | | | | | | | | | | | | | |
|---|---|---|---|---|---|---|---|---|---|---|---|---|---|---|---|---|
| ATG | GGC | ACG | AAT | CCT | AAA | CCT | CAG | AAG | AAG | AAC | AAA | CGT | AAC | ACC | AAC | 48 |
| Met | Gly | Thr | Asn | Pro | Lys | Pro | Gln | Lys | Lys | Asn | Lys | Arg | Asn | Thr | Asn | |
| 1 | | | | 5 | | | | | 10 | | | | | 15 | | |
| CGT | CGC | CCA | CAG | GAC | GTC | AAG | TTC | CCG | GGT | GGC | GGT | CAG | ATC | GTT | GGT | 96 |
| Arg | Arg | Pro | Gln | Asp | Val | Lys | Phe | Pro | Gly | Gly | Gly | Gln | Ile | Val | Gly | |
| | | | 20 | | | | | 25 | | | | | 30 | | | |
| GGA | GTT | TAC | TTG | TTG | CCG | CGC | AGG | GGC | CCT | AGA | TTG | GGT | GTG | CGC | GCG | 144 |
| Gly | Val | Tyr | Leu | Leu | Pro | Arg | Arg | Gly | Pro | Arg | Leu | Gly | Val | Arg | Ala | |
| | | 35 | | | | | 40 | | | | | 45 | | | | |
| ACG | AGA | AAG | ACT | TCC | GAG | CGG | TCG | CAA | CCT | CGA | GGT | AGA | CGT | CAG | CCT | 192 |
| Thr | Arg | Lys | Thr | Ser | Glu | Arg | Ser | Gln | Pro | Arg | Gly | Arg | Arg | Gln | Pro | |
| | | 50 | | | | 55 | | | | | 60 | | | | | |
| ATC | CCC | AAG | GCT | CGT | CGG | CCC | GAG | GGC | AGG | ACC | TGG | GCT | CAG | CCC | GGG | 240 |
| Ile | Pro | Lys | Ala | Arg | Arg | Pro | Glu | Gly | Arg | Thr | Trp | Ala | Gln | Pro | Gly | |

| | | | | | | | | | | | | | | | | |
|---|---|---|---|---|---|---|---|---|---|---|---|---|---|---|---|---|
| | 65 | | | | | 70 | | | | | 75 | | | | | 80 |
| TAC | CCT | TGG | CCC | CTC | TAT | GGC | AAT | GAG | GGC | TGC | GGG | TGG | GCG | GGA | TGG | 288 |
| Tyr | Pro | Trp | Pro | Leu | Tyr | Gly | Asn | Glu | Gly | Cys | Gly | Trp | Ala | Gly | Trp | |
| | | | | 85 | | | | | 90 | | | | | 95 | | |
| CTC | CTG | TCT | CCC | CGT | GGC | TCT | CGG | CCT | AGC | TGG | GGC | CCC | ACA | GAC | CCC | 336 |
| Leu | Leu | Ser | Pro | Arg | Gly | Ser | Arg | Pro | Ser | Trp | Gly | Pro | Thr | Asp | Pro | |
| | | | 100 | | | | | 105 | | | | | 110 | | | |
| CGG | CGT | AGG | TCG | CGC | AAT | TTG | GGT | AAG | GTC | ATC | GAT | ACC | CTT | ACG | TGC | 384 |
| Arg | Arg | Arg | Ser | Arg | Asn | Leu | Gly | Lys | Val | Ile | Asp | Thr | Leu | Thr | Cys | |
| | | 115 | | | | | 120 | | | | | 125 | | | | |
| GGC | TTC | GCC | GAC | CTC | ATG | GGG | TAC | ATA | CCG | CTC | GTC | GGC | GCC | CCT | CTT | 432 |
| Gly | Phe | Ala | Asp | Leu | Met | Gly | Tyr | Ile | Pro | Leu | Val | Gly | Ala | Pro | Leu | |
| | 130 | | | | | 135 | | | | | 140 | | | | | |
| GGA | GGC | GCT | GCC | AGG | GCC | CTG | GCG | CAT | GGC | GTC | CGG | GTT | CTG | GAA | GAC | 480 |
| Gly | Gly | Ala | Ala | Arg | Ala | Leu | Ala | His | Gly | Val | Arg | Val | Leu | Glu | Asp | |
| 145 | | | | | 150 | | | | | 155 | | | | | 160 | |
| GGC | GTG | AAC | TAT | GCA | ACA | GGG | AAC | CTT | CCT | GGT | TGC | TCT | TTC | TCT | ATC | 528 |
| Gly | Val | Asn | Tyr | Ala | Thr | Gly | Asn | Leu | Pro | Gly | Cys | Ser | Phe | Ser | Ile | |
| | | | | 165 | | | | | 170 | | | | | 175 | | |
| TTC | CTT | CTG | GCC | CTG | CTC | TCT | TGC | TTG | ACT | GTG | CCC | GCT | TCG | GCC | TAC | 576 |
| Phe | Leu | Leu | Ala | Leu | Leu | Ser | Cys | Leu | Thr | Val | Pro | Ala | Ser | Ala | Tyr | |
| | | | 180 | | | | | 185 | | | | | 190 | | | |
| CAA | GTG | CGC | AAC | TCC | ACG | GGG | CTT | TAC | CAC | GTC | ACC | AAT | GAT | TGC | CCT | 624 |
| Gln | Val | Arg | Asn | Ser | Thr | Gly | Leu | Tyr | His | Val | Thr | Asn | Asp | Cys | Pro | |
| | | 195 | | | | | 200 | | | | | 205 | | | | |
| AAC | TCG | AGC | ATT | GTG | TAC | GAG | TAA | TAG | GGA | TCC | | | | | | 657 |
| Asn | Ser | Ser | Ile | Val | Tyr | Glu | | | Gly | Ser | | | | | | |
| 210 | | | | | 215 | | | | | | | | | | | |

(2) INFORMATION FOR SEQ ID NO:14:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:14:

| | | | | | | | | | | | | | | |
|---|---|---|---|---|---|---|---|---|---|---|---|---|---|---|
| Met | Gly | Thr | Asn | Pro | Lys | Pro | Gln | Lys | Lys | Asn | Lys | Arg | Asn | Thr | Asn |
| 1 | | | | 5 | | | | | 10 | | | | | 15 | |
| Arg | Arg | Pro | Gln | Asp | Val | Lys | Phe | Pro | Gly | Gly | Gly | Gln | Ile | Val | Gly |
| | | | 20 | | | | | 25 | | | | | 30 | | |
| Gly | Val | Tyr | Leu | Leu | Pro | Arg | Arg | Gly | Pro | Arg | Leu | Gly | Val | Arg | Ala |
| | | | 35 | | | | | 40 | | | | | 45 | | |
| Thr | Arg | Lys | Thr | Ser | Glu | Arg | Ser | Gln | Pro | Arg | Gly | Arg | Arg | Gln | Pro |
| | 50 | | | | | 55 | | | | | 60 | | | | |
| Ile | Pro | Lys | Ala | Arg | Arg | Pro | Glu | Gly | Arg | Thr | Trp | Ala | Gln | Pro | Gly |
| 65 | | | | | 70 | | | | | 75 | | | | | 80 |
| Tyr | Pro | Trp | Pro | Leu | Tyr | Gly | Asn | Glu | Gly | Cys | Gly | Trp | Ala | Gly | Trp |
| | | | | 85 | | | | | 90 | | | | | 95 | |
| Leu | Leu | Ser | Pro | Arg | Gly | Ser | Arg | Pro | Ser | Trp | Gly | Pro | Thr | Asp | Pro |
| | | | 100 | | | | | 105 | | | | | 110 | | |
| Arg | Arg | Arg | Ser | Arg | Asn | Leu | Gly | Lys | Val | Ile | Asp | Thr | Leu | Thr | Cys |
| | | 115 | | | | | 120 | | | | | 125 | | | |
| Gly | Phe | Ala | Asp | Leu | Met | Gly | Tyr | Ile | Pro | Leu | Val | Gly | Ala | Pro | Leu |
| | 130 | | | | | 135 | | | | | 140 | | | | |
| Gly | Gly | Ala | Ala | Arg | Ala | Leu | Ala | His | Gly | Val | Arg | Val | Leu | Glu | Asp |
| 145 | | | | | 150 | | | | | 155 | | | | | 160 |

| | | | | | | | | | | | | | | |
|---|---|---|---|---|---|---|---|---|---|---|---|---|---|---|
| Gly | Val | Asn | Tyr | Ala | Thr | Gly | Asn | Leu | Pro | Gly | Cys | Ser | Phe | Ser | Ile |
| | | | | 165 | | | | | 170 | | | | | 175 | |
| Phe | Leu | Leu | Ala | Leu | Leu | Ser | Cys | Leu | Thr | Val | Pro | Ala | Ser | Ala | Tyr |
| | | | 180 | | | | | 185 | | | | | 190 | | |
| Gln | Val | Arg | Asn | Ser | Thr | Gly | Leu | Tyr | His | Val | Thr | Asn | Asp | Cys | Pro |
| | | 195 | | | | | 200 | | | | | 205 | | | |
| Asn | Ser | Ser | Ile | Val | Tyr | Glu | Gly | Ser | | | | | | | |
| | 210 | | | | | 215 | | | | | | | | | |

(2) INFORMATION FOR SEQ ID NO:15:

(i) SEQUENCE CHARACTERISTICS:
        (A) LENGTH: 453 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Hepatitis C Virus
        (B) STRAIN: CDC (vii) IMMEDIATE SOURCE:
        (B) CLONE: C1NC450

(ix) FEATURE:
        (A) NAME/KEY: CDS
        (B) LOCATION: 1..453

(xi) SEQUENCE DESCRIPTION: SEQ ID NO:15:

| | | | | | | | | | | | | | | | | |
|---|---|---|---|---|---|---|---|---|---|---|---|---|---|---|---|---|
| ATG | GGC | ACG | AAT | CCT | AAA | CCT | CAG | AAG | AAG | AAC | AAA | CGT | AAC | ACC | AAC | 48 |
| Met | Gly | Thr | Asn | Pro | Lys | Pro | Gln | Lys | Lys | Asn | Lys | Arg | Asn | Thr | Asn | |
| 1 | | | | 5 | | | | | 10 | | | | | 15 | | |
| CGT | CGC | CCA | CAG | GAC | GTC | AAG | TTC | CCG | GGT | GGC | GGT | CAG | ATC | GTT | GGT | 96 |
| Arg | Arg | Pro | Gln | Asp | Val | Lys | Phe | Pro | Gly | Gly | Gly | Gln | Ile | Val | Gly | |
| | | | 20 | | | | 25 | | | | | 30 | | | | |
| GGA | GTT | TAC | TTG | TTG | CCG | CGC | AGG | GGC | CCT | AGA | TTG | GGT | GTG | CGC | GCG | 144 |
| Gly | Val | Tyr | Leu | Leu | Pro | Arg | Arg | Gly | Pro | Arg | Leu | Gly | Val | Arg | Ala | |
| | | 35 | | | | 40 | | | | | 45 | | | | | |
| ACG | AGA | AAG | ACT | TCC | GAG | CGG | TCG | CAA | CCT | CGA | GGT | AGA | CGT | CAG | CCT | 192 |
| Thr | Arg | Lys | Thr | Ser | Glu | Arg | Ser | Gln | Pro | Arg | Gly | Arg | Arg | Gln | Pro | |
| | 50 | | | | 55 | | | | | 60 | | | | | | |
| ATC | CCC | AAG | GCT | CGT | CGG | CCC | GAG | GGC | AGG | ACC | TGG | GCT | CAG | CCC | GGG | 240 |
| Ile | Pro | Lys | Ala | Arg | Arg | Pro | Glu | Gly | Arg | Thr | Trp | Ala | Gln | Pro | Gly | |
| 65 | | | | 70 | | | | 75 | | | | | 80 | | | |
| TAC | CCT | TGG | CCC | CTC | TAT | GGC | AAT | GAG | GGC | TGC | GGG | TGG | GCG | GGA | TGG | 288 |
| Tyr | Pro | Trp | Pro | Leu | Tyr | Gly | Asn | Glu | Gly | Cys | Gly | Trp | Ala | Gly | Trp | |
| | | | | 85 | | | | | 90 | | | | | 95 | | |
| CTC | CTG | TCT | CCC | CGT | GGC | TCT | CGG | CCT | AGC | TGG | GGC | CCC | ACA | GAC | CCC | 336 |
| Leu | Leu | Ser | Pro | Arg | Gly | Ser | Arg | Pro | Ser | Trp | Gly | Pro | Thr | Asp | Pro | |
| | | | 100 | | | | | 105 | | | | | 110 | | | |
| CGG | CGT | AGG | TCG | CGC | AAT | TTG | GGT | AAG | GTC | ATC | GAT | ACC | CTT | ACG | TGC | 384 |
| Arg | Arg | Arg | Ser | Arg | Asn | Leu | Gly | Lys | Val | Ile | Asp | Thr | Leu | Thr | Cys | |
| | | 115 | | | | | 120 | | | | | 125 | | | | |
| GGC | TTC | GCC | GAC | CTC | ATG | GGG | TAC | ATA | CCG | CTC | GTC | GGC | GCC | CCT | CTT | 432 |
| Gly | Phe | Ala | Asp | Leu | Met | Gly | Tyr | Ile | Pro | Leu | Val | Gly | Ala | Pro | Leu | |
| | 130 | | | | | 135 | | | | | 140 | | | | | |
| GGA | GGC | GCT | GCC | AGG | GCC | TAA | | | | | | | | | | 453 |
| Gly | Gly | Ala | Ala | Arg | Ala | | | | | | | | | | | |
| 145 | | | | 150 | | | | | | | | | | | | |

( 2 ) INFORMATION FOR SEQ ID NO:16:

( i ) SEQUENCE CHARACTERISTICS:
        ( A ) LENGTH: 150 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met  Gly  Thr  Asn  Pro  Lys  Pro  Gln  Lys  Lys  Asn  Lys  Arg  Asn  Thr  Asn
 1              5                        10                       15

Arg  Arg  Pro  Gln  Asp  Val  Lys  Phe  Pro  Gly  Gly  Gly  Gln  Ile  Val  Gly
              20                       25                       30

Gly  Val  Tyr  Leu  Leu  Pro  Arg  Arg  Gly  Pro  Arg  Leu  Gly  Val  Arg  Ala
         35                        40                       45

Thr  Arg  Lys  Thr  Ser  Glu  Arg  Ser  Gln  Pro  Arg  Gly  Arg  Arg  Gln  Pro
     50                        55                       60

Ile  Pro  Lys  Ala  Arg  Arg  Pro  Glu  Gly  Arg  Thr  Trp  Ala  Gln  Pro  Gly
 65                       70                       75                       80

Tyr  Pro  Trp  Pro  Leu  Tyr  Gly  Asn  Glu  Gly  Cys  Gly  Trp  Ala  Gly  Trp
                    85                       90                       95

Leu  Leu  Ser  Pro  Arg  Gly  Ser  Arg  Pro  Ser  Trp  Gly  Pro  Thr  Asp  Pro
              100                      105                      110

Arg  Arg  Arg  Ser  Arg  Asn  Leu  Gly  Lys  Val  Ile  Asp  Thr  Leu  Thr  Cys
              115                      120                      125

Gly  Phe  Ala  Asp  Leu  Met  Gly  Tyr  Ile  Pro  Leu  Val  Gly  Ala  Pro  Leu
         130                      135                      140

Gly  Gly  Ala  Ala  Arg  Ala
145                      150
```

( 2 ) INFORMATION FOR SEQ ID NO:17:

( i ) SEQUENCE CHARACTERISTICS:
        ( A ) LENGTH: 360 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus
        ( B ) STRAIN: CDC ( v i i ) IMMEDIATE SOURCE:
        ( B ) CLONE: C1NC360

( i x ) FEATURE:
        ( A ) NAME/KEY: CDS
        ( B ) LOCATION: 1..360

( x i ) SEQUENCE DESCRIPTION: SEQ ID NO:17:

```
ATG  GGC  ACG  AAT  CCT  AAA  CCT  CAG  AAG  AAG  AAC  AAA  CGT  AAC  ACC  AAC    48
Met  Gly  Thr  Asn  Pro  Lys  Pro  Gln  Lys  Lys  Asn  Lys  Arg  Asn  Thr  Asn
 1              5                        10                       15

CGT  CGC  CCA  CAG  GAC  GTC  AAG  TTC  CCG  GGT  GGC  GGT  CAG  ATC  GTT  GGT    96
Arg  Arg  Pro  Gln  Asp  Val  Lys  Phe  Pro  Gly  Gly  Gly  Gln  Ile  Val  Gly
              20                       25                       30

GGA  GTT  TAC  TTG  TTG  CCG  CGC  AGG  GGC  CCT  AGA  TTG  GGT  GTG  CGC  GCG   144
Gly  Val  Tyr  Leu  Leu  Pro  Arg  Arg  Gly  Pro  Arg  Leu  Gly  Val  Arg  Ala
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     | 35  |     |     |     |     | 40  |     |     |     |     |     | 45  |     |     |     |
| ACG | AGA | AAG | ACT | TCC | GAG | CGG | TCG | CAA | CCT | CGA | GGT | AGA | CGT | CAG | CCT | 192 |
| Thr | Arg | Lys | Thr | Ser | Glu | Arg | Ser | Gln | Pro | Arg | Gly | Arg | Arg | Gln | Pro |     |
|     | 50  |     |     |     |     | 55  |     |     |     |     | 60  |     |     |     |     |     |
| ATC | CCC | AAG | GCT | CGT | CGG | CCC | GAG | GGC | AGG | ACC | TGG | GCT | CAG | CCC | GGG | 240 |
| Ile | Pro | Lys | Ala | Arg | Arg | Pro | Glu | Gly | Arg | Thr | Trp | Ala | Gln | Pro | Gly |     |
| 65  |     |     |     |     | 70  |     |     |     |     | 75  |     |     |     |     | 80  |     |
| TAC | CCT | TGG | CCC | CTC | TAT | GGC | AAT | GAG | GGC | TGC | GGG | TGG | GCG | GGA | TGG | 288 |
| Tyr | Pro | Trp | Pro | Leu | Tyr | Gly | Asn | Glu | Gly | Cys | Gly | Trp | Ala | Gly | Trp |     |
|     |     |     |     | 85  |     |     |     |     | 90  |     |     |     |     | 95  |     |     |
| CTC | CTG | TCT | CCC | CGT | GGC | TCT | CGG | CCT | AGC | TGG | GGC | CCC | ACA | GAC | CCC | 336 |
| Leu | Leu | Ser | Pro | Arg | Gly | Ser | Arg | Pro | Ser | Trp | Gly | Pro | Thr | Asp | Pro |     |
|     |     |     | 100 |     |     |     |     | 105 |     |     |     |     | 110 |     |     |     |
| CGG | CGT | AGG | TCG | CGC | AAT | TTG | TAA |     |     |     |     |     |     |     |     | 360 |
| Arg | Arg | Arg | Ser | Arg | Asn | Leu |     |     |     |     |     |     |     |     |     |     |
|     |     | 115 |     |     |     |     | 120 |     |     |     |     |     |     |     |     |     |

( 2 ) INFORMATION FOR SEQ ID NO:18:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

|     |     |     |     |     |     |     |     |     |     |     |     |     |     |     |
|-----|-----|-----|-----|-----|-----|-----|-----|-----|-----|-----|-----|-----|-----|-----|
| Met | Gly | Thr | Asn | Pro | Lys | Pro | Gln | Lys | Lys | Asn | Lys | Arg | Asn | Thr | Asn |
| 1   |     |     |     | 5   |     |     |     |     | 10  |     |     |     |     | 15  |     |
| Arg | Arg | Pro | Gln | Asp | Val | Lys | Phe | Pro | Gly | Gly | Gly | Gln | Ile | Val | Gly |
|     |     |     | 20  |     |     |     |     | 25  |     |     |     |     | 30  |     |     |
| Gly | Val | Tyr | Leu | Leu | Pro | Arg | Arg | Gly | Pro | Arg | Leu | Gly | Val | Arg | Ala |
|     |     |     | 35  |     |     |     |     | 40  |     |     |     |     | 45  |     |     |
| Thr | Arg | Lys | Thr | Ser | Glu | Arg | Ser | Gln | Pro | Arg | Gly | Arg | Arg | Gln | Pro |
|     | 50  |     |     |     |     | 55  |     |     |     |     | 60  |     |     |     |     |
| Ile | Pro | Lys | Ala | Arg | Arg | Pro | Glu | Gly | Arg | Thr | Trp | Ala | Gln | Pro | Gly |
| 65  |     |     |     |     | 70  |     |     |     |     | 75  |     |     |     |     | 80  |
| Tyr | Pro | Trp | Pro | Leu | Tyr | Gly | Asn | Glu | Gly | Cys | Gly | Trp | Ala | Gly | Trp |
|     |     |     |     | 85  |     |     |     |     | 90  |     |     |     |     | 95  |     |
| Leu | Leu | Ser | Pro | Arg | Gly | Ser | Arg | Pro | Ser | Trp | Gly | Pro | Thr | Asp | Pro |
|     |     |     | 100 |     |     |     |     | 105 |     |     |     |     | 110 |     |     |
| Arg | Arg | Arg | Ser | Arg | Asn | Leu |     |     |     |     |     |     |     |     |     |
|     |     | 115 |     |     |     |     |     |     |     |     |     |     |     |     |     |

( 2 ) INFORMATION FOR SEQ ID NO:19:

( i ) SEQUENCE CHARACTERISTICS:
        ( A ) LENGTH: 273 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus
        ( B ) STRAIN: CDC ( v i i ) IMMEDIATE SOURCE:
        ( B ) CLONE: C1NC270

( i x ) FEATURE:
    ( A ) NAME/KEY: CDS
    ( B ) LOCATION: 1..273

( x i ) SEQUENCE DESCRIPTION: SEQ ID NO:19:

```
ATG  GGC  ACG  AAT  CCT  AAA  CCT  CAG  AAG  AAG  AAC  AAA  CGT  AAC  ACC  AAC      48
Met  Gly  Thr  Asn  Pro  Lys  Pro  Gln  Lys  Lys  Asn  Lys  Arg  Asn  Thr  Asn
 1                   5                        10                       15

CGT  CGC  CCA  CAG  GAC  GTC  AAG  TTC  CCG  GGT  GGC  GGT  CAG  ATC  GTT  GGT      96
Arg  Arg  Pro  Gln  Asp  Val  Lys  Phe  Pro  Gly  Gly  Gly  Gln  Ile  Val  Gly
                20                        25                       30

GGA  GTT  TAC  TTG  TTG  CCG  CGC  AGG  GGC  CCT  AGA  TTG  GGT  GTG  CGC  GCG     144
Gly  Val  Tyr  Leu  Leu  Pro  Arg  Arg  Gly  Pro  Arg  Leu  Gly  Val  Arg  Ala
           35                       40                        45

ACG  AGA  AAG  ACT  TCC  GAG  CGG  TCG  CAA  CCT  CGA  GGT  AGA  CGT  CAG  CCT     192
Thr  Arg  Lys  Thr  Ser  Glu  Arg  Ser  Gln  Pro  Arg  Gly  Arg  Arg  Gln  Pro
      50                       55                        60

ATC  CCC  AAG  GCT  CGT  CGG  CCC  GAG  GGC  AGG  ACC  TGG  GCT  CAG  CCC  GGG     240
Ile  Pro  Lys  Ala  Arg  Arg  Pro  Glu  Gly  Arg  Thr  Trp  Ala  Gln  Pro  Gly
65                       70                        75                       80

TAC  CCT  TGG  CCC  CTC  TAT  GGC  AAT  GAG  GGC  TAA                               273
Tyr  Pro  Trp  Pro  Leu  Tyr  Gly  Asn  Glu  Gly
                      85                        90
```

( 2 ) INFORMATION FOR SEQ ID NO:20:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met  Gly  Thr  Asn  Pro  Lys  Pro  Gln  Lys  Lys  Asn  Lys  Arg  Asn  Thr  Asn
 1                   5                        10                       15

Arg  Arg  Pro  Gln  Asp  Val  Lys  Phe  Pro  Gly  Gly  Gly  Gln  Ile  Val  Gly
                20                        25                       30

Gly  Val  Tyr  Leu  Leu  Pro  Arg  Arg  Gly  Pro  Arg  Leu  Gly  Val  Arg  Ala
           35                       40                        45

Thr  Arg  Lys  Thr  Ser  Glu  Arg  Ser  Gln  Pro  Arg  Gly  Arg  Arg  Gln  Pro
      50                       55                        60

Ile  Pro  Lys  Ala  Arg  Arg  Pro  Glu  Gly  Arg  Thr  Trp  Ala  Gln  Pro  Gly
65                       70                        75                       80

Tyr  Pro  Trp  Pro  Leu  Tyr  Gly  Asn  Glu  Gly
                      85                        90
```

( 2 ) INFORMATION FOR SEQ ID NO:21:

( i ) SEQUENCE CHARACTERISTICS:
        ( A ) LENGTH: 183 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus
        ( B ) STRAIN: CDC ( v i i ) IMMEDIATE SOURCE:

( B ) CLONE: C100NC270

( i x ) FEATURE:
    ( A ) NAME/KEY: CDS
    ( B ) LOCATION: 1..183

( x i ) SEQUENCE DESCRIPTION: SEQ ID NO:21:

```
ATG  GGT  GGA  GTT  TAC  TTG  TTG  CCG  CGC  AGG  GGC  CCT  AGA  TTG  GGT  GTG        48
Met  Gly  Gly  Val  Tyr  Leu  Leu  Pro  Arg  Arg  Gly  Pro  Arg  Leu  Gly  Val
 1                  5                        10                       15

CGC  GCG  ACG  AGA  AAG  ACT  TCC  GAG  CGG  TCG  CAA  CCT  CGA  GGT  AGA  CGT        96
Arg  Ala  Thr  Arg  Lys  Thr  Ser  Glu  Arg  Ser  Gln  Pro  Arg  Gly  Arg  Arg
                20                        25                       30

CAG  CCT  ATC  CCC  AAG  GCT  CGT  CGG  CCC  GAG  GGC  AGG  ACC  TGG  GCT  CAG       144
Gln  Pro  Ile  Pro  Lys  Ala  Arg  Arg  Pro  Glu  Gly  Arg  Thr  Trp  Ala  Gln
           35                        40                       45

CCC  GGG  TAC  CCT  TGG  CCC  CTC  TAT  GGC  AAT  GAG  GGC  TAA                      183
Pro  Gly  Tyr  Pro  Trp  Pro  Leu  Tyr  Gly  Asn  Glu  Gly
     50                       55                       60
```

( 2 ) INFORMATION FOR SEQ ID NO:22:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met  Gly  Gly  Val  Tyr  Leu  Leu  Pro  Arg  Arg  Gly  Pro  Arg  Leu  Gly  Val
 1                  5                        10                       15

Arg  Ala  Thr  Arg  Lys  Thr  Ser  Glu  Arg  Ser  Gln  Pro  Arg  Gly  Arg  Arg
                20                        25                       30

Gln  Pro  Ile  Pro  Lys  Ala  Arg  Arg  Pro  Glu  Gly  Arg  Thr  Trp  Ala  Gln
           35                        40                       45

Pro  Gly  Tyr  Pro  Trp  Pro  Leu  Tyr  Gly  Asn  Glu  Gly
     50                       55                       60
```

( 2 ) INFORMATION FOR SEQ ID NO:23:

( i ) SEQUENCE CHARACTERISTICS:
        ( A ) LENGTH: 270 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus
        ( B ) STRAIN: CDC ( v i i ) IMMEDIATE SOURCE:
        ( B ) CLONE: C100NC360

( i x ) FEATURE:
        ( A ) NAME/KEY: CDS
        ( B ) LOCATION: 1..270

( x i ) SEQUENCE DESCRIPTION: SEQ ID NO:23:

```
ATG  GGT  GGA  GTT  TAC  TTG  TTG  CCG  CGC  AGG  GGC  CCT  AGA  TTG  GGT  GTG        48
Met  Gly  Gly  Val  Tyr  Leu  Leu  Pro  Arg  Arg  Gly  Pro  Arg  Leu  Gly  Val
 1                  5                        10                       15
```

| | | | | | | | | | | | | | | | | |
|---|---|---|---|---|---|---|---|---|---|---|---|---|---|---|---|---|
| CGC | GCG | ACG | AGA | AAG | ACT | TCC | GAG | CGG | TCG | CAA | CCT | CGA | GGT | AGA | CGT | 96 |
| Arg | Ala | Thr | Arg | Lys | Thr | Ser | Glu | Arg | Ser | Gln | Pro | Arg | Gly | Arg | Arg | |
| | | | 20 | | | | 25 | | | | | | 30 | | | |
| CAG | CCT | ATC | CCC | AAG | GCT | CGT | CGG | CCC | GAG | GGC | AGG | ACC | TGG | GCT | CAG | 144 |
| Gln | Pro | Ile | Pro | Lys | Ala | Arg | Arg | Pro | Glu | Gly | Arg | Thr | Trp | Ala | Gln | |
| | | 35 | | | | | 40 | | | | | 45 | | | | |
| CCC | GGG | TAC | CCT | TGG | CCC | CTC | TAT | GGC | AAT | GAG | GGC | TGC | GGG | TGG | GCG | 192 |
| Pro | Gly | Tyr | Pro | Trp | Pro | Leu | Tyr | Gly | Asn | Glu | Gly | Cys | Gly | Trp | Ala | |
| | 50 | | | | | 55 | | | | | 60 | | | | | |
| GGA | TGG | CTC | CTG | TCT | CCC | CGT | GGC | TCT | CGG | CCT | AGC | TGG | GGC | CCC | ACA | 240 |
| Gly | Trp | Leu | Leu | Ser | Pro | Arg | Gly | Ser | Arg | Pro | Ser | Trp | Gly | Pro | Thr | |
| 65 | | | | | 70 | | | | | 75 | | | | | 80 | |
| GAC | CCC | CGG | CGT | AGG | TCG | CGC | AAT | TTG | TAA | | | | | | | 270 |
| Asp | Pro | Arg | Arg | Arg | Ser | Arg | Asn | Leu | | | | | | | | |
| | | | | 85 | | | | | | | | | | | | |

( 2 ) INFORMATION FOR SEQ ID NO:24:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| | | | | | | | | | | | | | | | |
|---|---|---|---|---|---|---|---|---|---|---|---|---|---|---|---|
| Met | Gly | Gly | Val | Tyr | Leu | Leu | Pro | Arg | Arg | Gly | Pro | Arg | Leu | Gly | Val |
| 1 | | | | 5 | | | | | 10 | | | | | 15 | |
| Arg | Ala | Thr | Arg | Lys | Thr | Ser | Glu | Arg | Ser | Gln | Pro | Arg | Gly | Arg | Arg |
| | | | 20 | | | | 25 | | | | | | 30 | | |
| Gln | Pro | Ile | Pro | Lys | Ala | Arg | Arg | Pro | Glu | Gly | Arg | Thr | Trp | Ala | Gln |
| | | 35 | | | | | 40 | | | | | 45 | | | |
| Pro | Gly | Tyr | Pro | Trp | Pro | Leu | Tyr | Gly | Asn | Glu | Gly | Cys | Gly | Trp | Ala |
| | 50 | | | | | 55 | | | | | 60 | | | | |
| Gly | Trp | Leu | Leu | Ser | Pro | Arg | Gly | Ser | Arg | Pro | Ser | Trp | Gly | Pro | Thr |
| 65 | | | | | 70 | | | | | 75 | | | | | 80 |
| Asp | Pro | Arg | Arg | Arg | Ser | Arg | Asn | Leu | | | | | | | |
| | | | | 85 | | | | | | | | | | | |

( 2 ) INFORMATION FOR SEQ ID NO:25:

( i ) SEQUENCE CHARACTERISTICS:
        ( A ) LENGTH: 106 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Hepatitis C Virus
        ( B ) STRAIN: CDC ( v i i ) IMMEDIATE SOURCE:
        ( B ) CLONE: C1NC105

( i x ) FEATURE:
( A ) NAME/KEY: CDS
( B ) LOCATION: 1..106

( x i ) SEQUENCE DESCRIPTION: SEQ ID NO:25:

```
ATG GGC ACG AAT CCT AAA CCT CAG AAG AAG AAC AAA CGT AAC ACC AAC     48
Met Gly Thr Asn Pro Lys Pro Gln Lys Lys Asn Lys Arg Asn Thr Asn
```

-continued

```
              1                   5                       10                      15
            CGT  CGC  CCA  CAG  GAC  GTC  AAG  TTC  CCG  GGT  GGC  GGT  CAG  ATC  GTT  GGT        96
            Arg  Arg  Pro  Gln  Asp  Val  Lys  Phe  Pro  Gly  Gly  Gly  Gln  Ile  Val  Gly
                           20                       25                      30

GGA  GTT  TTA  A                                                                     106
            Gly  Val  Leu
                      35
```

( 2 ) INFORMATION FOR SEQ ID NO:26:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met  Gly  Thr  Asn  Pro  Lys  Pro  Gln  Lys  Lys  Asn  Lys  Arg  Asn  Thr  Asn
 1                   5                       10                      15

Arg  Arg  Pro  Gln  Asp  Val  Lys  Phe  Pro  Gly  Gly  Gly  Gln  Ile  Val  Gly
               20                       25                      30

Gly  Val  Leu
          35
```